US008034575B2

(12) United States Patent
Wechsler et al.

(10) Patent No.: US 8,034,575 B2
(45) Date of Patent: *Oct. 11, 2011

(54) SCREENING SYSTEMS UTILIZING RTP801

(75) Inventors: Roni Wechsler, Shoham (IL); Igor Mett, Rehovot (IL); Elena Feinstein, Rehovot (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/800,738

(22) Filed: May 21, 2010

(65) Prior Publication Data

US 2011/0045499 A1 Feb. 24, 2011

Related U.S. Application Data

(63) Continuation of application No. 11/803,130, filed on May 11, 2007, now Pat. No. 7,723,052.

(60) Provisional application No. 60/799,827, filed on May 11, 2006, provisional application No. 60/817,257, filed on Jun. 28, 2006, provisional application No. 60/855,101, filed on Oct. 26, 2006.

(51) Int. Cl.
*G01N 33/53* (2006.01)
*G01N 33/566* (2006.01)
*G01N 33/567* (2006.01)

(52) U.S. Cl. ......... 435/7.2; 435/7.1; 435/7.21; 436/501; 530/300; 530/350

(58) Field of Classification Search .................. None
See application file for complete search history.

(56) References Cited

U.S. PATENT DOCUMENTS

| | | | |
|---|---|---|---|
| 6,455,674 B1 | 9/2002 | Einat et al. | |
| 6,555,667 B1 | 4/2003 | Einat et al. | |
| 6,673,549 B1 | 1/2004 | Furness et al. | |
| 6,740,738 B2 | 5/2004 | Einat et al. | |
| 2002/0119463 A1 | 8/2002 | Faris | |
| 2002/0137077 A1 | 9/2002 | Hopkins et al. | |
| 2003/0104973 A1 | 6/2003 | Einat et al. | |
| 2003/0108871 A1 | 6/2003 | Kaser | |
| 2003/0165864 A1 | 9/2003 | Lasek et al. | |
| 2006/0240022 A1 | 10/2006 | Klippel-Giese et al. | |
| 2007/0149467 A1 | 6/2007 | Lee | |
| 2007/0178090 A1 | 8/2007 | Sukumar et al. | |
| 2007/0185017 A1 | 8/2007 | Aggarwal et al. | |
| 2007/0224201 A1 | 9/2007 | Wu et al. | |
| 2007/0281326 A1 | 12/2007 | Wechsler et al. | |
| 2008/0014599 A1 | 1/2008 | Wechsler et al. | |
| 2008/0064650 A1 | 3/2008 | Feinstein et al. | |
| 2008/0269156 A1 | 10/2008 | Feinstein et al. | |

FOREIGN PATENT DOCUMENTS

| | | |
|---|---|---|
| CA | 234602 | 4/2001 |
| DE | 19816395 | 10/1999 |
| EP | 1 394 274 A2 | 3/2004 |
| EP | 1 104 808 A1 | 9/2005 |
| EP | 1 580 263 A1 | 9/2005 |
| JP | 2003-259877 | 9/2003 |
| WO | WO 00/14283 | 3/2000 |
| WO | WO 00/61620 | 10/2000 |
| WO | WO 00/77022 A1 | 12/2000 |
| WO | WO 01/70979 A2 | 9/2001 |
| WO | WO 01/77289 A2 | 10/2001 |
| WO | WO 01/12659 A2 | 12/2001 |
| WO | WO 01/96391 A2 | 12/2001 |
| WO | WO 02/31111 A2 | 4/2002 |
| WO | WO 02/46465 A2 | 6/2002 |
| WO | WO 02/068579 A2 | 9/2002 |
| WO | WO 02/101075 A2 | 12/2002 |
| WO | WO 03/010205 A1 | 2/2003 |
| WO | WO 03/025138 A2 | 3/2003 |
| WO | WO 03/029271 A2 | 4/2003 |
| WO | WO 03/087768 A2 | 10/2003 |
| WO | WO 03/101283 | 12/2003 |
| WO | WO 2004/018999 A2 | 3/2004 |
| WO | WO 2004/045545 A2 | 6/2004 |
| WO | WO 2004/048520 A3 | 6/2004 |
| WO | WO 2004/048938 A2 | 6/2004 |
| WO | WO 2004/060270 A2 | 7/2004 |
| WO | WO 2005/016000 A1 | 2/2005 |
| WO | WO 2005/044981 A2 | 5/2005 |

OTHER PUBLICATIONS

Elena Feinstein and Rami Skaliter, U.S. Appl. No. 11/655,636, filed Jan. 18, 2007 pending claims.
Birukova AA, et al. (2004) "Novel role of microtubules in thrombin induced endothelial barrier dysfunction," *FASEB J.* December;18(15):1879-90.
Brafman, A. et al., (2004) "Inhibition of Oxygen-Induced Retinopathy In RTP801-Deficient Mice," *Investigative Opthalmology & Visual Science*, 45(10): 3796-3805.
Brugarolas, J. et al., (2004) "Regulation of mTOR Function In Response to Hypoxia By REDD1 And The TSC1/TSC2 Tumor Suppressor Complex," *Genes & Development*, 18: 2893-2904.
Bulinski JC, et al. (1991) "Stabilization of post-translational modification of microtubules during cellular morphogenesis," *Bioessays*. June;13(6):285-93.
Cai SL, et al. (2006) "Activity of TSC2 is inhibited by AKT-mediated phosphorylation and membrane partitioning," *J Cell Biol*. Apr. 24;173(2):279-89.
Choi JH, (2000) "TOR signaling regulates microtubule structure and function," *Curr Biol*. Jul. 13;10(14):861-4.
Corradetti MN, (2005)The stress-inducted proteins RTP801 and RTP801L are negative regulators of the mammalian target of rapamycin pathway. J Biol Chem. Mar. 18;280(11):9769-72.

(Continued)

*Primary Examiner* — Christine J Saoud
*Assistant Examiner* — Jon M Lockard
(74) *Attorney, Agent, or Firm* — John P. White; Cooper & Dunham LLP

(57) ABSTRACT

RTP801 represents a unique gene target for hypoxia-inducible factor-1 (HIF-1). Down-regulation of the mTOR pathway activity by hypoxia requires de novo mRNA synthesis and correlates with increased expression of RTP801.
The present invention relates to screening systems utilizing RTP801 and/or RTP801 interactors to and/or RTP801 biological activity, to drug candidates identified by such screening systems, and to the use of such drug candidates in the treatment of various disorders.

18 Claims, 37 Drawing Sheets

OTHER PUBLICATIONS

Cuaz-perolin et al., (2004) REDD2 gene is upregulated by modified LDL or hypoxia and mediates human macrophage cell death. Arterioscler Thromb Vasc Biol. October;24(10):1830-5. Epub Aug. 12, 2004.

Ellisen LW. (2005) Growth control under stress: mTOR regulation through the REDD1-TSC pathway. Cell Cycle. November;4(11):1500-02.

Ellisen, L. et al., (2002) "REDD1, A Developmentally Regulated Transcriptional Target of p63 and p53, Links p63 To Regulation of Reactive Oxygen Species," *Molecular Cell*, 10: 995-1005.

Frolov, A. et al., (2003) "Response Markers and the Molecular Mechanisms of Action of Gleevec in Gastrointestinal Stromal Tumors," *Molecular Cancer Therapeutics*, 2: 699-709.

Gau CL, et al. (2005) "Farnesyltransferase inhibitors reverse altered growth and distribution of actin filaments in Tsc-deficient cells via inhibition of both rapamycin-sensitive and -insensitive pathways," *Mol Cancer Ther*. June;4(6):918-26.

Honore S, et al. (2005): Understanding microtubule dynamics for improved cancer therapy. Cell Mol Life Sci. December;62(24):3039-56. Review.

Jiang X, Yeung RS (2006) "Regulation of microtubule-dependent protein transport by the TSC2/mammalian target of rapamycin pathway," *Cancer Res*. May 15;66(10):5258-69.

Jozwiak J, et al. (2005): Positive and negative regulation of TSC2 activity and its effects on downstream effectors of the mTOR pathway. Neuromolecular Med. 7(4):287-96.

Kim, J. et al., (2003) "Identification of Amyloid β-peptide Responsive Genes by cDNA Microarray Technology: Involvement of *RTP801* In Amyloid β-peptide Toxicity," *Experimental and Molecular Medicine*, 35(5): 403-411.

Lal, A. et al., (2001) "Transcriptional Response to Hypoxia in Human Tumors," *Journal of the National Cancer Institute*, 93(17): 1337-1343.

Lee, M. et al., (2004) "Sp1-Dependant Regulation of the RTP801 Promoter and Its Application To Hypoxia-Inducible VEGF Plasmid For Ischemic Disease," *Pharmaceutical Research*, 21(5) : 736-741.

Li Y, et all. (2005) "Measurements of TSC2 GAP Activity Toward Rheb," *Methods Enzymol*. 407:46-54.

Liu H, et al. (2006):. Mechanism of Akt1 inhibition of breast cancer cell invasion reveals a protumorigenic role for TSC2. Proc Natl Acad Sci U S A. Mar. 14;103(11):4134-9.

Peris L, et al. (2006) "Job D. Tubulin tyrosination is a major factor affecting the recruitment of CAP-Gly proteins at microtubule plus ends," *J Cell Biol*. Sep. 11;174(6):839-49.

Pisani et al., (2005) SMHS1 is involved in oxidative/glycolytic-energy metabolism balance of muscle fibers. Biochem Biophys Res Commun Jan. 28;326(4):788-93.

Rangasamy, R. et al., (2004) "Genetic Ablation of Nrf2 Enhances Susceptibility To Cigarrette Smoke-Induced Emphysema in Mice," *The Journal of Clinical Investigation*, 114(9): 1248-1259.

Reiling, J. and Hafen, E., (2004) "The Hypoxia-Induced Paralogs Scylla and Charybdis Inhibit Growth by Down-Regulating S6K Activity Upstream of TSC In Drosophila," *Genes & Development*, 18:2879-2892.

Richard, D. et al., (2000) "Nonhypoxic Pathway Mediates the Induction of Hypoxia-Inducible Factor 1α in Vascular Smooth Muscle Cells," *The Journal of Biological Chemistry*, 275(35):26765-26771.

Sarbassov DD, et al. (2006): Prolonged rapamycin treatment inhibits mTORC2 assembly and Akt/PKB.Mol Cell. Apr. 21;22(2):159-68.

Schwarzer, R. et al., (2005) "REDD1 Integrates Hypoxia-Mediated Survival Signaling Downstream of Phosphatidylinositol 3-kinase," *Oncogene*, 24: 1138-1149.

Shoshani, T. et al., (2002) "Identification of a Novel Hypoxia-Inducible Factor 1-Responsive Gene, *RTP801*, Involved in Apoptosis," *Molecular and Cell Biology*, 22(7): 2283-2293.

Sofer A, et al. (2005): Regulation of mTOR and cell growth in response to energy stress by REDD1. Mol Cell Biol. July;25(14):5834-45.

Strausberg, R. et al., (2002) "Generation and Initial Analysis of More Than 15,000 Full-Length Human and Mouse cDNA Sequences," *Proceedings of the National Academy of Sciences of the United States of America*, 99(26): 16899-16903.

Tee AR, et al. (2003): Tuberous sclerosis complex gene products, Tuberin and Hamartin, control mTOR signaling by acting as a GTPase-activating protein complex toward Rheb. Curr Biol. Aug. 5;13(15):1259-68.

Wang, J. and Ortiz de Montellano, P., (2003) "The Binding Sites on Human Heme Oxygenase-1 for Cytochrome P450 Reductase and Biliverdin Reductase," *The American Society for Biochemistry and Molecular Biology*, Inc., p. 1-38.

Zhang Y, et al. (2003) "Rheb is a direct target of the tuberous sclerosis tumor suppressor proteins," *Nat Cell Biol*. June;5(6):578-81.

International Search Report issued by the International Searching Authority (ISA/US) on May 23, 2007 in connection with International Application No. PCT/IL04/00924.

Written Opinion of the International Searching Authority (ISA/US) issued on May 23, 2007 in connection with International Application No. PCT/IL04/00924.

Corradetti, MN, et al., (2005), "The Stress-inducted Proteins RTP801 and RTP801L Are Negative Regulators of the Mammalian Target of Rapamycin Pathway", J. of Biol. Chem., vol. 280, pp. 9769-9772.

Malagelada, C., et al., (2006), "RTP801 is Elevated in Parkinson Brain Substantia Nigral Neurons and Mediates Death in Cellular Models of Parkinson's Disease by a Mechanism Involving Mammalian Target of Rapamycin Inactivation", J. of Neuroscience, 26(39):9996-10005.

Gery, S., et al., (2007), "RTP801 is a novel retinoic acid-responsive gene associated with myeloid differentiation", Experimental Hematology, 35, pp. 572-578.

May 28, 2010 Official Action issued in connection with United Kingdom Patent Application No. GB0820038.8.

Figure 1

```
TTTGGCCCTC GAGGCCAAGA ATTCGGCACG AGGGGGGGAG GTGCGAGCGT GGACCTGGGA   60
CGGGTCTGGG CGGCTCTCGG TGGTTGGCAC GGGTTCGCAC ACCCATTCAA GCGGCAGGAC  120
GCACTTGTCT TAGCAGTTCT CGCTGACCGC GCTAGCTGCG GCTTCTACGC TCCGGCACTC  180
TGAGTTCATC AGCAAACGCC CTGGCGTCTG TCCTCACCATGGCCTAGCCTT TGGGACCGCT  240
TCTCGTCGTC GTCCACCTCC TCTTCGCCCT CGTCCTTGCC CCGAACTCCC ACCCCAGATC  300
GGCCGCCGCG CTCAGCCTGG GGGTCGGCGA CCCGGGAGGA GGGGTTTGAC CGCTCCACGA  360
GCCTGGAGAG CTCGGACTGC GAGTCCCTGG ACAGCAGCAA CAGTGGCTTC GGGCCGGAGG  420
AAGACACGGC TTACCTGGAT GGGGTGTCGT TGCCCGACTT CGAGCTGCTC AGTGACCCTG  480
AGGATGAACA CTTGTGTGCC AACCTGATGC AGCTGCTGCA GGAGAGCCTG GCCCAGGCGC  540
GGCTGGGCTC TCGACGCCCT GCGCGCCTGC TGATGCCTAG CCAGTTGGTA AGCCAGGTGG  600
GCAAAGAACT ACTGCGCCTG GCCTACAGCG AGCCGTGCGG CCTGCGGGGG GCGCTGCTGG  660
ACGTCTGCGT GGAGCAGGGC AAGAGCTGCC ACAGCGTGGG CCAGCTGGCA CTCGACCCCA  720
GCCTGGTGCC CACCTTCCAG CTGACCCTCG TGCTGCGCCT GGACTCACGA CTCTGGCCCA  780
AGATCCAGGG GCTGTTTAGC TCCGCCAACT CTCCCTTCCT CCCTGGCTTC AGCCAGTCCC  840
TGACGCTGAG CACTGGCTTC CGAGTCATCA AGAAGAAGCT GTACAGCTCG GAACAGCTGC  900
TCATTGAGGA GTGTTGAACT TCAACCTGAG GGGCCGACA GTGCCCTCCA AGACAGAGAC  960
GACTGAACTT TTGGGGTGGA GACTAGAGGC AGGAGCTGAG GGACTGATTC CTGTGGTTGG 1020
AAAACTGAGG CAGCCACCTA AGGTGGAGGT GGGGAATAG TGTTTCCCAG GAAGCTCATT 1080
GAGTTGTGTG CGGGTGGCTG TGCATTGGGG ACACATACCC CTCAGTACTG TAGCATGAAA 1140
CAAAGGCTTA GGGGCCAACA AGGCTTCCAG CTGGATGTGT GTGTAGCATG TACCTTATTA 1200
TTTTTGTTAC TGACAGTTAA CAGTGGTGTG ACATCCAGAG AGCAGCTGGG CTGCTCCCGC 1260
CCCAGCCCGG CCCAGGGTGA AGGAAGAGGC ACGTGCTCCT CAGAGCAGCC GGAGGGAGGG 1320
GGGAGGTCGG AGGTCGTGGA GGTGGTTTGT GTATCTTACT GGTCTGAAGG GACCAAGTGT 1380
GTTTGTTGTT TGTTTTGTAT CTTGTTTTTC TGATCGGAGC ATCACTACTG ACCTGTTGTA 1440
GGCAGCTATC TTACAGACGC ATGAATGTAA GAGTAGGAAG GGGTGGGTGT CAGGGATCAC 1500
TTGGGATCTT TGACACTTGA AAAATTACAC CTGGCAGCTG CGTTTAAGCC TTCCCCCATC 1560
CTGTACTGCA GAGTTGAGCT GGCAGGGGAG GGGCTGAGAG GGTGGGGGCT GGAACCCCTC 1620
CCCGGGAGGA GTGCCATCTG GGTCTTCCAT CTAGAACTGT TTACATGAAG ATAAGATACT 1680
CACTGTTCAT GAATACACTT GATGTTCAAG TATTAAGACC TATGCAATAT TTTTTACTTT 1740
TCTAATAAAC ATGTTTGTTA AAACAAAAAA AAAAAAAAAA AA                    1782
```

Figure 2

MPSLWDRFSS SSTSSSPSSL PRTPTPDRPP RSAWGSATRE EGFDRSTSLE 50
SSDCESLDSS NSGFGPEEDT AYLDGVSLPD FELLSDPEDE HLCANLMQLL 100
QESLAQARLG SRRPARLLMP SQLVSQVGKE LLRLAYSEPC GLRGALLDVC 150
VEQGKSCHSV GQLALDPSLV PTFQLTLVLR LDSRLWPKIQ GLFSSANSPF 200
LPGFSQSLTL STGFRVIKKK LYSSEQLLIE EC  232

Figure 3A

```
   1 atggcccaac aagcaaatgt cggggagctt cttgccatgc tggactcccc catgctgggt
  61 gtgcgggacg acgtgacagc tgtctttaaa gagaacctca attctgaccg tggccctatg
 121 cttgtaaaca ccttggtgga ttattacctg gaaaccagct ctcagccggc attgcacatc
 181 ctgaccacct tgcaagagcc acatgacaag cacctcttgg acaggattaa cgaatatgtg
 241 ggcaaagccg ccactcgttt atccatcctc tcgttactgg gtcatgtcat aagactgcag
 301 ccatcttgga agcataagct ctctcaagca cctcttttgc cttctttact aaaatgtctc
 361 aagatggaca ctgacgtcgt tgtcctcaca acaggcgtct tggtgttgat aaccatgcta
 421 ccaatgattc cacagtctgg gaaacagcat cttcttgatt tctttgacat ttttggccgt
 481 ctgtcatcat ggtgcctgaa gaaaccaggc cacgtggcgg aagtctatct cgtccatctc
 541 catgccagtg tgtacgcact ctttcatcgc ctttatggaa tgtacccttg caacttcgtc
 601 tccttttgc gttctcatta cagtatgaaa gaaacctgg agactttga agaagtggtc
 661 aagccaatga tggagcatgt gcgaattcat ccggaattag tgactggatc caaggaccat
 721 gaactggacc ctcgaaggtg gaagagatta gaaactcatg atgttgtgat cgagtgtgcc
 781 aaaatctctc tggatcccac agaagcctca tatgaagatg ctattctgt gtctcaccaa
 841 atctcagccc gctttcctca tcgttcagcc gatgtcacca ccagcccta tgctgacaca
 901 cagaatagct atgggtgtgc tacttctacc ccttactcca cgtctcggct gatgttgtta
 961 aatatgccag gcagctacc tcagactctg agttccccat cgacacggct gataactgaa
1021 ccaccacaag ctactctttg gagcccatct atggtttgtg tatgaccac tcctccaact
1081 tctcctggaa atgtcccacc tgatctgtca cacccttaca gtaaagtctt tggtacaact
1141 gcaggtggaa aaggaactcc tctgggaacc ccagcaacct ctcctcctcc agccccactc
1201 tgtcattcgg atgactacgt gcacattca ctcccccagg ccacagtcac acccccagg
1261 aaggaagaga gaatggattc tgcaagacca tgtctacaca gacaaccaca tcttctgaat
1321 gacagaggat cagaagagcc acctggcagc aaaggttctg tcactctaag tgatcttcca
1381 gggtttttag gtgatctggc ctctgaagaa gatagtattg aaaaagataa agaagaagct
1441 gcaatatcta gagaactttc tgagatcacc acagcagagg cagagcctgt ggttcctcga
1501 ggaggctttg actctccctt ttaccgagac agtctcccag gttctcagcg gaagacccac
1561 tcggcagcct ccagttctca gggcgccagc gtgaacctg agcctttaca ctcctccctg
1621 gacaagcttg ggcctgacac accaaagcaa gcctttactc ccatagacct gccctgcggc
1681 agtgctgatg aaagccctgc gggagacagg gaatgccaga cttctttgga gaccagtatc
1741 ttcactccca gtccttgtaa aattccacct ccgacgagag tgggctttgg aagcgggcag
1801 cctcccccgt atgatcatct ttttgaggtg gcattgccaa agacagccca tcatttgtc
1861 atcaggaaga ctgaggagct gttaaagaaa gcaaaggaa acacagagga gatggtgtg
1921 ccctctacct ccccaatgga agtgctggac agactgatac agcagggagc agacgcgcac
1981 agcaaggagc tgaacaagtt gcctttaccc agcaagtctg tcgactggac ccactttgga
2041 ggctctcctc cttcagatga gatccgcacc ctccgagacc agttgctttt actgcacaac
2101 cagttactct atgagcgttt taagaggcag cagcatgccc tccggaacag gcggctcctc
2161 cgcaaggtga tcaaagcagc agctctggag aacataatg ctgccatgaa agatcagttg
2221 aagttacaag agaaggacat ccagatgtgg aaggttagtc tgcagaaaga acaagctaga
2281 tacaatcagc tccaggagca gcgtgacact atggtaacca agctccacag ccagatcaga
2341 cagctgcagc atgaccgaga ggaattctac aaccagagcc aggaattaca gacgaagctg
2401 gaggactgca ggaacatgat tgcggagctg cggatagaac tgaagaaggc caacaacaag
2461 gtgtgtcaca ctgagctgct gctcagtcag gtttcccaaa agctctcaaa cagtgagtcg
2521 gtccagcagc agatggagtt cttgaacagg cagctgttgg ttcttgggga ggtcaacgag
2581 ctctatttgg aacaactgca gaacaagcac tcagatacca aaggaagt agaaatgatg
2641 aaagccgcct atcggaaaga gctagaaaaa acagaagcc atgttctcca gcagactcag
2701 aggcttgata cctcccaaaa acggattttg gaactggaat ctcacctggc caagaaagac
2761 caccttcttt tggaacagaa gaaatatcta gaggatgtca aactccaggc aagaggacag
2821 ctgcaggccg cagagagcag gtatgaggct cagaaaagga taacccaggt gtttgaattg
2881 gagatcttag atttatatgg caggttggag aaagatggcc tcctgaaaaa acttgaagaa
2941 gaaaaagcag aagcagctga agcagcagaa gaaaggcttg actgttgtaa tgacgggtgc
3001 tcagattcca tggtagggca caatgaagag gcatctggcc acaacggtga gaccaagacc
```

Figure 3B

```
3061 cccaggccca gcagcgcccg gggcagtagt ggaagcagag gtggtggagg cagcagcagc
3121 agcagcagcg agctttctac cccagagaaa cccccacacc agagggcagg cccattcagc
3181 agtcggtggg agacgactat gggagaagcg tctgccagca tccccaccac tgtgggctca
3241 cttcccagtt caaaaagctt cctgggtatg aaggctcgag agttatttcg taataagagc
3301 gagagccagt gtgatgagga cggcatgacc agtagccttt ctgagagcct aaagacagaa
3361 ctgggcaaag acttgggtgt ggaagccaag attcccctga acctagatgg ccctcacccg
3421 tctcccccga ccccggacag tgttggacag ctacatatca tggactacaa tgagactcat
3481 catgaacaca gctaa
```

Figure 4

```
   1 maqqanvgel lamldspmlg vrddvtavfk enlnsdrgpm lvntlvdyyl etssqpalhi
  61 ltlqephdk hlldrineyv gkaatrlsil sllghvirlq pswkhklsqa pllpsllkcl
 121 kmdtdvvvlt tgvlvlitml pmipqsgkqh lldffdifgr lsswclkkpg hvaevylvhl
 181 hasvyalfhr lygmypcnfv sflrshysmk enletfeevv kpmmehvrih pelvtgskdh
 241 eldprrwkrl ethdvvieca kisldpteas yedgysvshq isarfphrsa dvttspyadt
 301 qnsygcatst pystsrlmll nmpgqlpqtl sspstrlite ppqatlwsps mvcgmttppt
 361 spgnvppdls hpyskvfgtt aggkgtplgt patspppapl chsddyvhis lpqatvtppr
 421 keermdsarp clhrqhhlln drgseeppgs kgsvtlsdlp gflgdlasee dsiekdkeea
 481 aisrelseit taeaepvvpr ggfdspfyrd slpgsqrkth saasssqgas vnpeplhssl
 541 dklgpdtpkq aftpidlpcg sadespagdr ecqtsletsi ftpspckipp ptrvgfgsgq
 601 pppydhlfev alpktahhfv irkteellkk akgnteedgv pstspmevld rliqqgadah
 661 skelnklplp sksvdwthfg gsppsdeirt lrdqllllhn qllyerfkrq qhalrnrrll
 721 rkvikaaale ehnaamkdql klqekdiqmw kvslqkeqar ynqlqeqrdt mvtklhsqir
 781 qlqhdreefy nqsqelqtkl edcrnmiael rielkkannk vchtelllsq vsqklsnses
 841 vqqqmeflnr qllvlgevne lyleqlqnkh sdttkevemm kaayrkelek nrshvlqqtq
 901 rldtsqkril eleshlakkd hllleqkkyl edvklqargq lqaaesryea qkritqvfel
 961 eildlygrle kdgllkklee ekaeaaeaae erldccndgc sdsmvghnee asghngetkt
1021 prpssargss gsrgggsss ssselstpek pphqragpfs srwettmgea sasipttvgs
1081 lpssksflgm karelfrnks esqcdedgmt sslseslkte lgkdlgveak iplnldgphp
1141 spptpdsvgq lhimdyneth hehs
```

Figure 5A

```
   1 atggccaaac caacaagcaa agattcaggc ttgaaggaga agtttaagat tctgttggga
  61 ctgggaacac cgaggccaaa tcccaggtct gcagagggta aacagacgga gtttatcatc
 121 accgcggaaa tactgagaga actgagcatg gaatgtggcc tcaacaatcg catccggatg
 181 atagggcaga tttgtgaagt cgcaaaaacc aagaaatttg aagagcacgc agtggaagca
 241 ctctggaagg cggtcgcgga tctgttgcag ccggagcgga cgctggaggc ccggcacgcg
 301 gtgctggctc tgctgaaggc catcgtgcag gggcagggcg agcgtttggg ggtcctcaga
 361 gccctcttct ttaaggtcat caaggattac ccttccaacg aagaccttca cgaaaggctg
 421 gaggttttca aggccctcac agacaatggg agacacatca cctacttgga ggaagagctg
 481 gctgactttg tcctgcagtg gatggatgtt ggcttgtcct cggaattcct tctggtgctg
 541 gtgaacttgg tcaaattcaa tagctgttac ctcgacgagt acatcgcaag gatggttcag
 601 atgatctgtc tgctgtgcgt ccggaccgcg tcctctgtgg acatagaggt ctccctgcag
 661 gtgctggacg ccgtggtctg ctacaactgc ctgccggctg agagcctccc gctgttcatc
 721 gttaccctct gtcgcaccat caacgtcaag gagctctgcg agccttgctg gaagctgatg
 781 cggaacctcc ttggcaccca cctgggccac agcgccatct acaacatgtg ccacctcatg
 841 gaggacagag cctacatgga ggacgcgccc ctgctgagag gagccgtgtt ttttgtgggc
 901 atggctctct ggggagccca ccggctctat tctctcagga actcgccgac atctgtgttt
 961 ccatcatttt accaggccat ggcatgtccg aacgaggtgg tgtcctatga gatcgtcctg
1021 tccatcacca ggctcatcaa gaagtatagg aaggagctcc aggtggtggc gtgggacatt
1081 ctgctgaaca tcatcgaacg gctccttcaa cagctccaga ccttggacag cccggagctc
1141 aggaccatcg tccatgacct gttgaccacg gtggaggagc tgtgtgacca gaacgagttc
1201 cacgggtctc aggagagata ctttgaactg gtggagagat gtgcggacca gaggcctgag
1261 tcctcccctcc tgaacctgat ctcctataga gcgcagtcca tccacccggc caaggacggc
1321 tggattcaga acctgcaggc gctgatggag agattcttca ggagcgagtc ccgaggcgcc
1381 gtgcgcatca aggtgctgga cgtgctgtcc tttgtgctgc tcatcaacag gcagttctat
1441 gaggaggagc tgattaactc agtggtcatc tcgcagctct cccacatccc cgaggataaa
1501 gaccaccagg tccgaaagct ggccacccag ttgctggtgg acctggcaga gggctgccac
1561 acacaccact tcaacagcct gctggacatc atcgagaagg tgatggcccg ctccctctcc
1621 ccaccccccgg agctggaaga aagggatgtg gccgcatact cggcctcctt ggaggatgtg
1681 aagacagccg tcctgggcct tctggtcatc cttcagacca agctgtacac cctgcctgca
1741 agccacgcca cgcgtgtgta tgagatgctg gtcagccaca ttcagctcca ctacaagcac
1801 agctacaccc tgccaatcgc gagcagcatc cggctgcagg cctttgactt cctgtttctg
1861 ctgcgggccg actcactgca ccgcctgggc ctgcccaaca aggatggagt cgtgcggttc
1921 agcccctact gcgtctgcga ctacatggag ccagagagag gtctgagaa gaagaccagc
1981 ggccccccttt ctcctcccac agggcctcct ggccggcgc ctgcaggccc cgccgtgcgg
2041 ctggggtccg tgccctactc cctgctcttc cgcgtcctgc tgcagtgctt gaagcaggag
2101 tctgactgga aggtgctgaa gctggttctg ggcaggctgc ctgagtccct cgcgctataaa
2161 gtgctcatct ttacttcccc ttgcagtgtg gaccagctgt gctctgctct ctgctccatg
2221 ctttcaggcc caaagacact ggagcggctc cgaggcgccc cagaaggctt ctccagaact
2281 gacttgcacc tggccgtggt tccagtgctg acagcattaa tctcttacca taactacctg
2341 gacaaaacca aacagcgcga gatggtctac tgcctggagc agggcctcat ccaccgctgt
2401 gccagacagt gcgtcgtggc cttgtccatc tgcagcgtgg agatgcctga catcatcatc
2461 aaggcgctgc ctgttctggt ggtgaagctc acgcacatct cagccacagc cagcatggcc
2521 gtccactgc tggagttcct gtccactctg gccaggctgc cgcacctcta caggaacttt
2581 gccgcggagc agtatgccag tgtgttcgcc atctccctgc cgtacaccaa ccctccaag
2641 tttaatcagt acatcgtgtg tctggcccat cacgtcatag ccatgtggtt catcaggtgc
2701 cgcctgccct tccggaagga ttttgtccct ttcatcacta agggcctgcg gtccaatgtc
2761 ctcttgtctt ttgatgacac ccccgagaag gacagcttca gggcccggag tactagtctc
2821 aacgagagac ccaagagtct gaggatagcc agacccccca aacaaggctt gaataactct
2881 ccacccgtga agaattcaa ggagagctct gcagccgagg ccttccggtg ccgcagcatc
2941 agtgtgtctg aacatgtggt ccgcagcagg atacagacgt ccctcaccag tgccagcttg
3001 gggtctgcag atgagaactc cgtggcccag gctgacgata gcctgaaaaa cctccacctg
```

Figure 5B

```
3061 gagctcacgg aaacctgtct ggacatgatg gctcgatacg tcttctccaacttcacggct
3121 gtcccgaaga ggtctcctgt gggcgagttc ctcctagcgg gtggcaggac caaaacctgg
3181 ctggttggga acaagcttgt cactgtgacg acaagcgtgg gaaccgggac ccggtcgtta
3241 ctaggcctgg actcggggga gctgcagtcc ggcccggagt cgagctccag ccccggggtg
3301 catgtgagac agaccaagga ggcgccggcc aagctggagt cccaggctgg gcagcaggtg
3361 tcccgtgggg cccgggatcg ggtccgttcc atgtcggggg gccatggtct tcgagttggc
3421 gccctggacg tgccggcctc ccagttcctg ggcagtgcca cttctccagg accacggact
3481 gcaccagccg cgaaacctga gaaggcctca gctggcaccc gggttcctgt gcaggagaag
3541 acgaacctgg cggcctatgt gcccctgctg acccagggct gggcggagat cctggtccgg
3601 aggcccacag ggaacaccag ctggctgatg agcctggaga acccgctcag cccttttctcc
3661 tcggacatca acaacatgcc cctgcaggag ctgtctaacg ccctcatggc ggctgagcgc
3721 ttcaaggagc accgggacac agccctgtac aagtcactgt cggtgccggc agccagcacg
3781 gccaaacccc ctcctctgcc tcgctccaac acagtggcct ctttctcctc cctgtaccag
3841 tccagctgcc aaggacagct gcacaggagc gtttcctggg cagactccgc cgtggtcatg
3901 gaggagggaa gtccgggcga ggttcctgtg ctggtggagc ccccagggtt ggaggacgtt
3961 gaggcagcgc taggcatgga caggcgcacg gatgcctaca gcaggtcgtc ctcagtctcc
4021 agccaggagg agaagtcgct ccacgcggag gagctggttg gcagggggcat ccccatcgag
4081 cgagtcgtct cctcggaggg tggccggccc tctgtggacc tctccttcca gccctcgcag
4141 cccctgagca gtccagctc ctctcccgag ctgcagactc tgcaggacat cctcggggac
4201 cctggggaca aggccgacgt gggccggctg agccctgagg ttaaggcccg gtcacagtca
4261 gggaccctgg acggggaaag tgctgcctgg tcggcctcgg gcgaagacag tcggggccag
4321 cccgagggtc ccttgccttc cagctccccc cgctcgccca gtggcctccg gccccgaggt
4381 tacaccatct ccgactcggc cccatcacgc aggggcaaga gagtagagag ggacgcctta
4441 aagagcagag ccacagcctc caatgcagag aaagtgccag gcatcaaccc cagtttcgtg
4501 ttcctgcagc tctaccattc ccccttcttt ggcgacgagt caaacaagcc aatcctgctg
4561 cccaatgagt cacagtcctt tgagcggtcg gtgcagctcc tcgaccagat cccatcatac
4621 gacacccaca agatcgccgt cctgtatgtt ggagaaggcc agagcaacag cgagctcgcc
4681 atcctgtcca atgagcatgg ctcctacagg tacacggagt tcctgacggg cctgggccgg
4741 ctcatcgagc tgaaggactg ccagccggac aaggtgtacc tgggaggcct ggacgtgtgt
4801 ggtgaggacg gccagttcac ctactgctgg cacgatgaca tcatgcaagc cgtcttccac
4861 atcgccaccc tgatgcccac caaggacgtg gacaagcacc gctgcgacaa gaagcgccac
4921 ctgggcaacg actttgtgtc cattgtctac aatgactccg gtgaggactt caagcttggc
4981 accatcaagg gccagttcaa ctttgtccac gtgatcgtca ccccgctgga ctacgagtgc
5041 aacctggtgt ccctgcagtg caggaaagac atggagggcc ttgtggacac cagcgtggcc
5101 aagatcgtgt ctgaccgcaa cctgcccttc gtggcccgcc agatggccct gcacgcaaat
5161 atggcctcac aggtgcatca tagccgctcc aacccccaccg atatctaccc ctccaagtgg
5221 attgcccggc tccgccacat caagcggctc cgccagcgga tctgcgagga agccgcctac
5281 tccaacccca gcctacctct ggtgcacccct ccgtcccata gcaaagcccc tgcacagact
5341 ccagccgagc ccacacctgg ctatgaggtg ggccagcgga agcgcctcat ctcctcggtg
5401 gaggacttca ccgagtttgt gtga
```

Figure 6

```
   1 makptskdsg lkekfkillg lgtprprnprs aegkqtefii taeilrelsm ecglnnrirm
  61 igqicevakt kkfeehavea lwkavadllq pertlearha vlallkaivq gqgerlgvlr
 121 alffkvikdy psnedlherl evfkaltdng rhityleeel adfvlqwmdv glssefllvl
 181 vnlvkfnscy ldeyiarmvq micllcvrta ssvdievslq vldavvcync lpaeslplfi
 241 vtlcrtinvk elcepcwklm mllgthlgh saiynmchlm edraymedap llrgavffvg
 301 malwgahrly slrnsptsvf psfyqamacp nevvsyeivl sitrlikkyr kelqvvawdi
 361 llniierllq qlqtldspel rtivhdlltt veelcdqnef hgsqeryfel vercadqrpe
 421 ssllnlisyr aqsihpakdg wiqnlqalme rffrsesrga vrikvldvls fvllinrqfy
 481 eeelinsvvi sqlshipedk dhqvrklatq llvdlaegch thhfnslldi iekvmarsls
 541 pppeleerdv aaysasledv ktavlgllvi lqtklytlpa shatrvyeml vshiqlhykh
 601 sytlpiassi rlqafdflfl lradslhrlg lpnkdgvvrf spycvcdyme pergsekkts
 661 gplspptgpp gpapagpavr lgsvpysllf rvllqclkqe sdwkvlklvl grlpeslryk
 721 vliftspcsv dqlcsalcsm lsgpktlerl rgapegfsrt dlhlavvpvl talisyhnyl
 781 dktkqremvy cleqglihrc arqcvvalsi csvempdiii kalpvlvvkl thisatasma
 841 vplleflstl arlphlyrnf aaeqyasvfa islpytnpsk fnqyivclah hviamwfirc
 901 rlpfrkdfvp fitkglrsnv llsfddtpek dsfrarstsl nerpkslria rppkqglnns
 961 ppvkefkess aaeafrcrsi svsehvvrsr iqtsltsasl gsadensvaq addslknlhl
1021 eltetcldmm aryvfsnfta vpkrspvgef llaggrtktw lvgnklvtvt tsvgtgtrsl
1081 lgldsgelqs gpesssspgv hvrqtkeapa klesqagqqv srgardrvrs msgghglrvg
1141 aldvpasqfl gsatspgprt apaakpekas agtrvpvqek tnlaayvpll tqgwaeilvr
1201 rptgntswlm slenplspfs sdinnmplqe lsnalmaaer fkehrdtaly kslsvpaast
1261 akppplprsn tvasfsslyq sscqgqlhrs vswadsavvm eegspgevpv lveppgledv
1321 eaalgmdrrt daysrsssvs sqeekslhae elvgrgipie rvvsseggrp svdlsfqpsq
1381 plsksssspe lqtlqdilgd pgdkadvgrl spevkarsqs gtldgesaaw sasgedsrgq
1441 pegplpsssp rspsglrprg ytisdsapsr rgkrverdal ksratasnae kvpginpsfv
1501 flqlyhspff gdesnkpill pnesqsfers vqlldqipsy dthkiavlyv gegqsnsela
1561 ilsnehgsyr ytefltglgr lielkdcqpd kvylggldvc gedgqftycw hddimqavfh
1621 iatlmptkdv dkhrcdkkrh lgndfvsivy ndsgedfklg tikgqfnfvh vivtpldyec
1681 nlvslqcrkd meglvdtsva kivsdrnlpf varqmalhan masqvhhsrs nptdiypskw
1741 iarlrhikrl rqriceeaay snpslplvhp pshskapaqt paeptpgyev gqrkrlissv
1801 edftefv
```

Figure 7

```
   1 atgcgtgagt gcatctccat ccacgttggc caggctggtg tccagattgg caatgcctgc
  61 tgggagctct actgcctgga acacggcatc cagcccgatg gccagatgcc aagtgacaag
 121 accattgggg gaggagatga ctccttcaac accttcttca gtgagacggg cgctggcaag
 181 cacgtccccc gggctgtgtt tgtagacttg gaacccacag tcattgatga agttcgcact
 241 ggcacctacc gccagctctt ccaccctgag cagctcatca caggcaagga agatgctgcc
 301 aataactatg cccgagggca ctacaccatt ggcaaggaga tcattgacct tgtgttggac
 361 cgaattcgca agctggctga ccagtgcacc ggtcttcagg gcttcttggt tttccacagc
 421 tttggtgggg gaactggttc tgggttcacc tccctgctca tggaacgtct ctcagttgat
 481 tatggcaaga agtccaagct ggagttctcc atttacccag cacccaggt ttccacagct
 541 gtagttgagc cctacaactc catcctcacc acccacacca ccctggagca ctctgattgt
 601 gccttcatgg tagacaatga ggccatctat gacatctgtc gtagaaacct cgatatcgag
 661 cgcccaacct acactaacct taaccgcctt attagccaga ttgtgtcctc catcactgct
 721 tccctgagat tgatggagc cctgaatgtt gacctgacag aattccagac caacctggtg
 781 ccctaccccc gcatccactt ccctctggcc acatatgccc ctgtcatctc tgctgagaaa
 841 gcctaccatg aacagctttc tgtagcagag atcaccaatg cttgctttga gccagccaac
 901 cagatggtga aatgtgaccc tcgccatggt aaatacatgg cttgctgcct gttgtaccgt
 961 ggtgacgtgg ttcccaaaga tgtcaatgct gccattgcca ccatcaaaac caagcgcagc
1021 atccagtttg tggattggtg ccccactggc ttcaaggttg gcatcaacta ccagcctccc
1081 actgtggtgc ctggtggaga cctggccaag gtacagagag ctgtgtgcat gctgagcaac
1141 accacagcca ttgctgaggc ctgggctcgc ctggaccaca gtttgacct gatgtatgcc
1201 aagcgtgcct ttgttcactg gtacgtgggt gaggggatgg aggaaggcga gttttcagag
1261 gcccgtgaag atatggctgc ccttgagaag gattatgagg aggttggtgt ggattctgtt
1321 gaaggagagg gtgaggaaga aggagaggaa tactaa
```

Figure 8

```
  1 mrecisihvg qagvqignac welyclehgi qpdgqmpsdk tigggddsfn tffsetgagk
 61 hvpravfvdl eptvidevrt gtyrqlfhpe qlitgkedaa nnyarghyti gkeiidlvld
121 rirkladqct glqgflvfhs fgggtgsgft sllmerlsvd ygkksklefs iypapqvsta
181 vvepynsilt thttlehsdc afmvdneaiy dicrrnldie rptytnlnrl isqivssita
241 slrfdgalnv dltefqtnlv pyprihfpla tyapvisaek ayheqlsvae itnacfepan
301 qmvkcdprhg kymaccllyr gdvvpkdvna aiatiktkrs iqfvdwcptg fkvginyqpp
361 tvvpggdlak vqravcmlsn ttaiaeawar ldhkfdlmya krafvhwyvg egmeegefse
421 aredmaalek dyeevgvdsv egegeeegee y
```

Figure 10

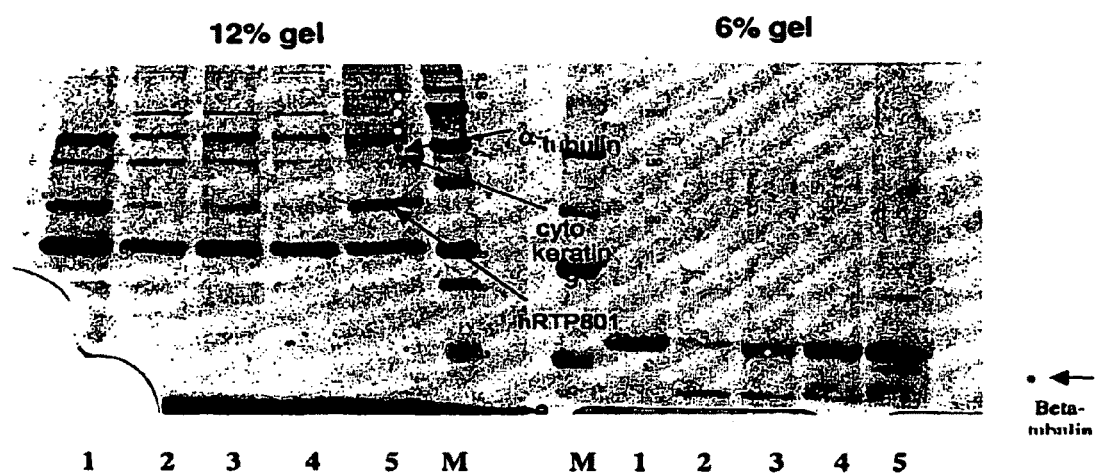

Lane 1: Anti-FLAG beads
Lane 2: Eluant from anti-FLAG beads incubated with extract from control cells, untreated
Lane 3: Eluant from anti-FLAG beads incubated with extract from FLAG-hRTP801 cells, untreated
Lane 4: Eluant from anti-FLAG beads incubated with extract from control cells, cobalt chloride-treated
Lane 5: Eluant from anti-FLAG beads incubated with extract from FLAG-hRTP801 cells cobalt chloride -treated Figure 15A
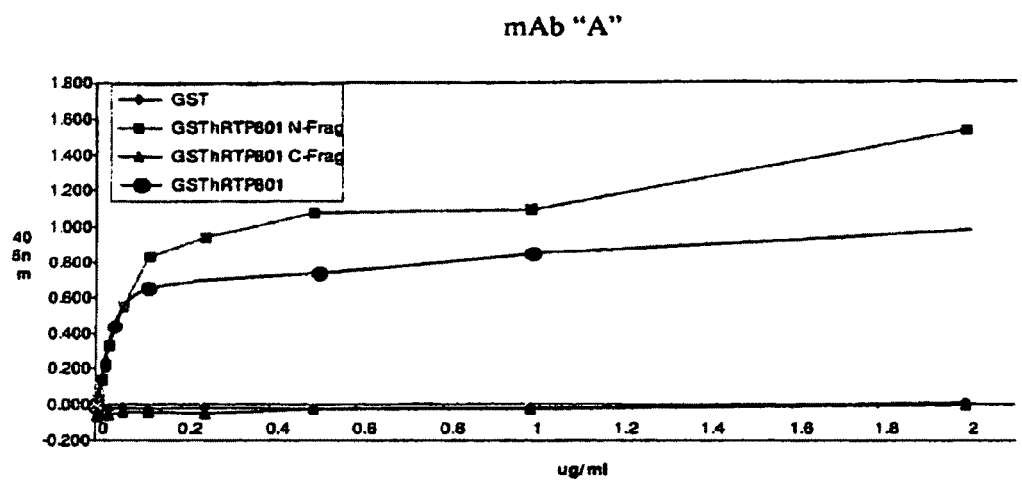
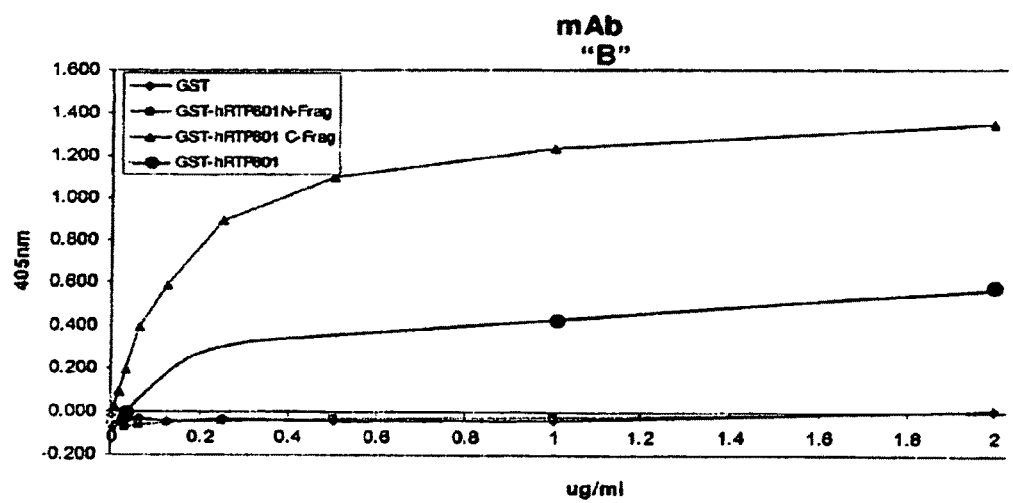

ELISA-based Assay for Screening Small Compounds that disrupt RTP801/TSC2 complex

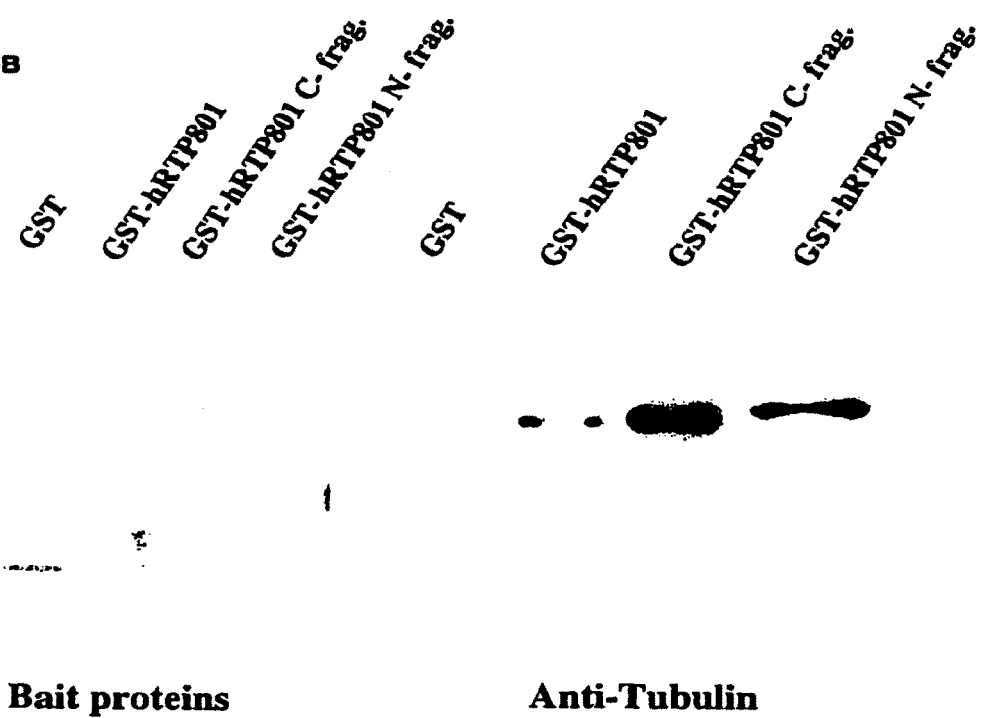

Bait: FLAG-tagged hRTP801 fragments (identified with anti-hRTP801 antibodies)

Prey: HA-SV5-tagged full-length hRTP801 (identified with anti-SV5 Abs)

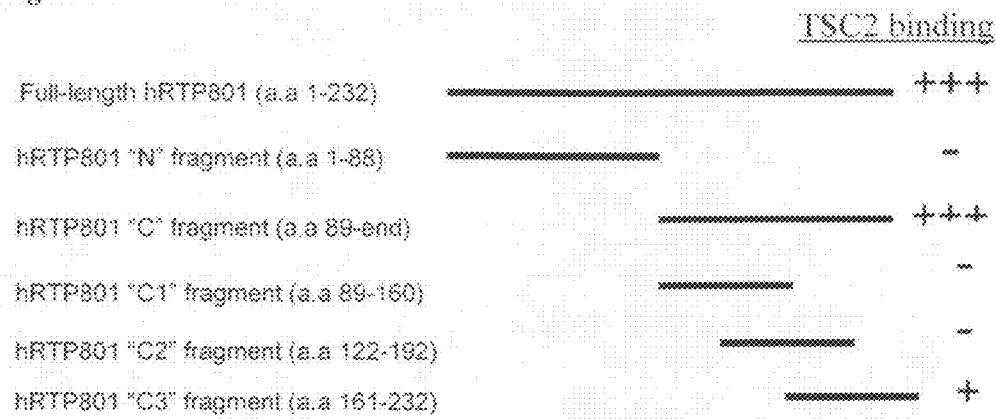
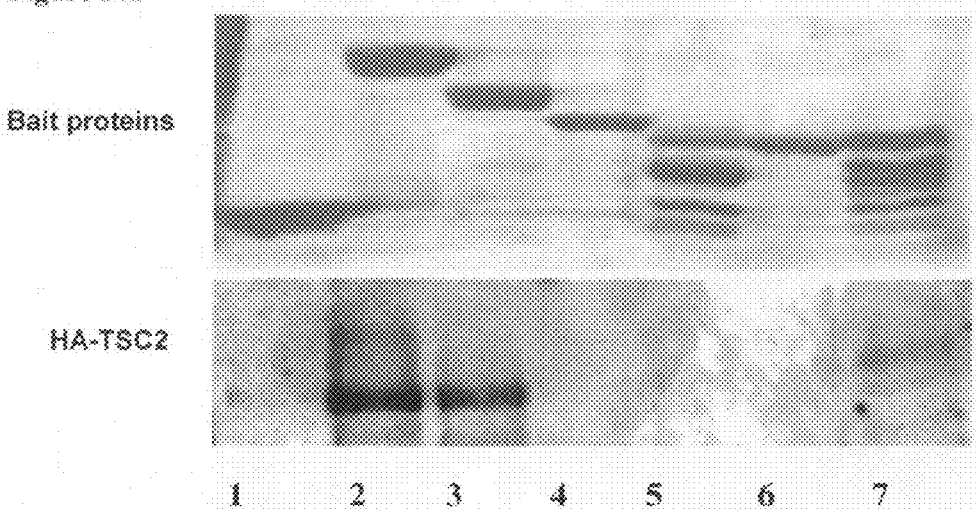
1. GST
2. GST-FLAG-hRTP801
3. GST-FLAG-hRTP801 "C" fragment
4. GST-FLAG-hRTP801 "N" fragment
5. GST-FLAG-hRTP801 "C1" fragment
6. GST-FLAG-hRTP801 "C2" fragment
7. GST-FLAG-hRTP801 "C3" fragment

US 8,034,575 B2

SCREENING SYSTEMS UTILIZING RTP801

This application is a continuation of U.S. Ser. No. 11/803,130, filed May 11, 2007, now U.S. Pat. No. 7,723,052, issued May 25, 2010, which claims the benefit of U.S. Provisional patent applications Nos. 60/799,827, filed May 11, 2006; 60/817,257, filed Jun. 28, 2006 and 60/855,101, filed Oct. 26, 2006, each of which is hereby incorporated by reference in its entirety into this application.

Throughout this application, various scientific publications, or United States Patents or Published Applications, are referenced by author and year or by number, respectively. The disclosures of in these publications as of these U.S. published patents and patent applications in their entireties are hereby incorporated by reference into this application in order to more fully describe the state of the art to which this invention pertains.

FIELD OF THE INVENTION

The present invention relates to novel screening systems utilizing RTP801, and to the use of molecules identified by such screening systems to treat neurodegenerative diseases, respiratory disorders of all types (including pulmonary disorders), eye diseases and conditions, microvascular disorders, angiogenesis- and apoptosis-related conditions, neurodegenerative diseases and hearing impairments.

BACKGROUND OF THE INVENTION

Current modes of therapy for the prevention and/or treatment of apoptosis-related and neurodegenerative diseases, ischemic conditions, COPD, macular degeneration, microvascular diseases and ototoxic conditions are unsatisfactory and there is a need therefore to develop novel compounds for this purpose. The present invention is focused on processes for identifying such compounds. All the diseases and indications disclosed herein, as well as other diseases and conditions disclosed in coassigned PCT Application No. WO06/023544A2 may also be treated by the novel compounds of this invention.

RTP801

Gene RTP801, was first disclosed in commonly assigned U.S. Pat. Nos. 6,455,674, 6,555,667, and 6740738, including the RTP801 polynucleotide and polypeptide, and antibodies directed toward the polypeptide. RTP801 represents a unique gene target for hypoxia-inducible factor-1 (HIF-1) that may regulate hypoxia-induced pathogenesis independent of growth factors such as VEGF.

The following patent applications and publications provide background information:
to PCT Publication No. WO 2001070979 relates to nucleic acid markers, which are overexpressed in ovarian cancer cells.
U.S. Pat. No. 6,673,549 discloses a combination comprising cDNAs that are differentially expressed in response to steroid treatment.
US Patent Publication No. 2003165864 relates to cDNAs that are differentially expressed in cells treated with a DNA demethylating agent.
US Patent Publication No. 2003108871 relates to a composition comprising several cDNAs that are differentially expressed in treated human C3A liver cell cultures.
US Patent Publication No. 2002119463 discloses a new composition, useful for treating and diagnosing prostate cancer, said composition comprising human cDNAs that are differentially expressed in prostate cancer.
PCT Publication No. WO 2004018999 discloses a method for assessing, characterizing, monitoring, preventing and treating cervical cancer.
European Patent No. EP 1394274 relates to a method of testing for bronchial asthma or chronic obstructive pulmonary disease by comparing the expression level of a marker gene in a biological sample from a subject with the expression level of the gene in a sample from a healthy subject.
PCT Publication No. WO 2002101075 relates to an isolated nucleic acid molecule useful for detecting, characterizing, preventing and treating human cervical cancers.
PCT Publication No. WO 2003010205 relates to inhibiting angiogenesis for treating wound healing, retinopathy, ischemia, inflammation, microvasculopathy, bone healing and skin inflammation.
PCT Publication No. WO 2002046465 relates to identifying a gene involved in disease for treating hypoxia-regulated conditions.
PCT Publication No. WO 2002031111 relates to polypeptides and their encoded proteins, and many uses therefore are provided.
PCT Publication No. WO 2001012659 relates to nucleic acids useful in recombinant DNA methodologies.
PCT Publication No. WO 2001077289 discloses six hundred and twenty three polynucleotides derived from a variety of human tissue sources.
PCT Publication No. WO 2003101283 relates to a combination which comprises many cDNAs and proteins
Japan Patent No. JP 2003259877 relates to many hepatic fibrosis disease markers.
Tzipora Shoshani, et al. *Identification of a Novel Hypoxia-Inducible Factor 1-Responsive Gene, RTP801, Involved in Apoptosis*. MOLECULAR AND CELLULAR BIOLOGY, April 2002, p. 2283-2293; this paper, co-authored by the inventor of the present invention, details the discovery of the RTP801 gene (a then novel HIF-1-dependent gene).
Anat Brafman, et al. Inhibition of Oxygen-Induced Retinopathy in RTP801-Deficient Mice. Invest Ophthalmol Vis Sci. 2004 October; 45 (10): 3796-805; also co-authored by the inventor of the present invention, this paper demonstrates that in RTP801 knock out mice, hypoxia does not cause degeneration of the retinal capillary network.
Leif W. Ellisen, et al. *REDD1, a Developmentally Regulated Transcriptional Target of p63 and p53, Links p63 to Regulation of Reactive Oxygen Species*. Molecular Cell. Vol. 10, 995-1005, November, 2002; this paper demonstrates that overexpression of RTP801 (referred to therein as REDD1) leads to increased production of reactive oxygen species.
Richard D R, Berra E, and Pouyssegur J. *Non-hypoxic pathway mediates the induction of hypoxia-inducible factor 1 alpha in vascular smooth muscle cells*. J. Biol. Chem. 2000, September; 275(35): 26765-71. This paper demonstrates that HIF-1-dependent transcription may be induced by excessive production of reactive oxygen species.
Rangasami T, et al., *Genetic ablation of Nrf2 enhances susceptibility to cigarette smoke-induced emphysema in mice*. Submitted to *Journal of Clinical Investigation*. This work relates to mice with a compromised antioxidant defense (due to a germline inactivation of RTP801).
The mTOR Pathway Tuberous sclerosis is an autosomal-dominant disorder caused by the mutation of one of the two tumor suppressor genes: TSC1 or TSC2, (TSC=Tuberous Sclerosis Complex) encoding protein products, hamartin, and tuberin, respectively. Both proteins form intracellular complexes exerting inhibitory activity on mammalian target of rapamycin (mTOR) kinase. It has been demonstrated that signal transduction from tuberin to mTOR is mediated by a G protein, Ras homologue enriched in brain (Rheb). In normal cells, tuberin having GTPase-activating protein properties toward Rheb controls signals of nutrient depletion, hypoxia, or stress, not allowing activation of mTOR and subsequent protein translation and cell proliferation. However, when environmental conditions change, tuberin is phosphorylated and it forms a complex with hamartin is degraded, and downstream targets of mTOR, S6K, and eEF2K, can be activated. (Jozwiak J, Jozwiak S, Grzela T, Lazarczyk M: Positive and negative regulation of TSC2 activity and its effects on downstream effectors of the mTOR pathway. Neuromolecular Med. 2005; 7(4):287-96).

mTOR is a central regulator of protein synthesis the activity of which is modulated by a variety of signals. Energy depletion and hypoxia result in mTOR inhibition through a process involving the activation of AMP-activated protein kinase (AMPK) by LKB1 and subsequent phosphorylation of TSC2. It has been shown that mTOR inhibition by hypoxia requires the TSC1/TSC2 tumor suppressor complex and RTP801. Disruption of the TSC1/TSC2 complex through loss of TSC1 or TSC2 blocks the effects of hypoxia on mTOR, as measured by changes in the mTOR targets S6K and 4E-BP1, and results in abnormal accumulation of Hypoxia-inducible factor (HIF). In contrast to energy depletion, mTOR inhibition by hypoxia does not require AMPK or LKB1. Downregulation of mTOR activity by hypoxia requires de novo mRNA synthesis and correlates with increased expression of RTP801. Disruption of RTP801 abrogates the hypoxia-induced inhibition of mTOR, and RTP801 overexpression is sufficient to down-regulate S6K phosphorylation in a TSC1/TSC2-dependent manner. (Brugarolas 1, Lei K, Hurley R L, Manning B D, Reiling J H, Hafen E, Witters L A. Ellisen L W, Kaelin W G Jr.: Regulation of mTOR function in response to hypoxia by REDD1 and the TSC1/TSC2 tumor suppressor complex. Genes Dev. 2004 Dec. 1; 18(23):2893-904.)

Additionally, it has recently been demonstrated that RTP801 potently inhibit signaling through mTOR, working downstream of AKT and upstream of TSC2 to inhibit mTOR functions. (Corradetti M N, et al., J Biol. Chem. 2005 Mar. 18; 280(11):9769-72).

SUMMARY OF THE INVENTION

The present invention relates to screening systems useful for identifying molecules which inhibit or enhance the activity of RTP801, thereby identifying molecules which may be used for the treatment of various diseases and conditions. Thus, in some embodiments, the present invention comprises processes for identifying a test compound useful for modulating the activity of an RTP801 polypeptide The present invention further provides novel methods and compositions for treating apoptotic or neurodegenerative diseases, as well as microvascular disorders, macular degeneration, respiratory disorders, and spinal cord injury or disease.

BRIEF DESCRIPTION OF THE FIGURES

FIG. 1 details the coding sequence of the RTP801 gene (SEQ ID NO:1);

FIG. 2 details the amino acid sequence of the RTP801 polypeptide (SEQ ID NO:2);

FIGS. 3A and 3B detail the coding sequence of the TSC1 gene (SEQ ID NO:31; gi: 56699466

FIG. 4 details the amino acid sequence of the TSC 1 polypeptide (SEQ ID NO:4):

FIGS. 5A and 5B detail the coding sequence of the TSC2 gene (SEQ ID NO:5); gi: 10938006

FIG. 6 details the amino acid sequence of the TSC2 polypeptide (SEQ ID NO:6);

FIG. 7 details the coding sequence of the alpha-tubulin gene (SEQ ID NO:7); gi: 47938359

FIG. 8 details the amino acid sequence of the alpha-tubulin polypeptide (SEQ ID NO:8);

FIG. 10 discovery of alpha/beta tubulin and cytokeratin-9 as proteins that co-IP with FLAG-hRTP801—demonstrates that alpha/beta tubulin and cytokeratin-9 co-immunoprecipitate with RTP801;

FIG. 24 shows the RTP801 region that hinds TSC2;

DETAILED DESCRIPTION OF THE INVENTION

Figure 9:
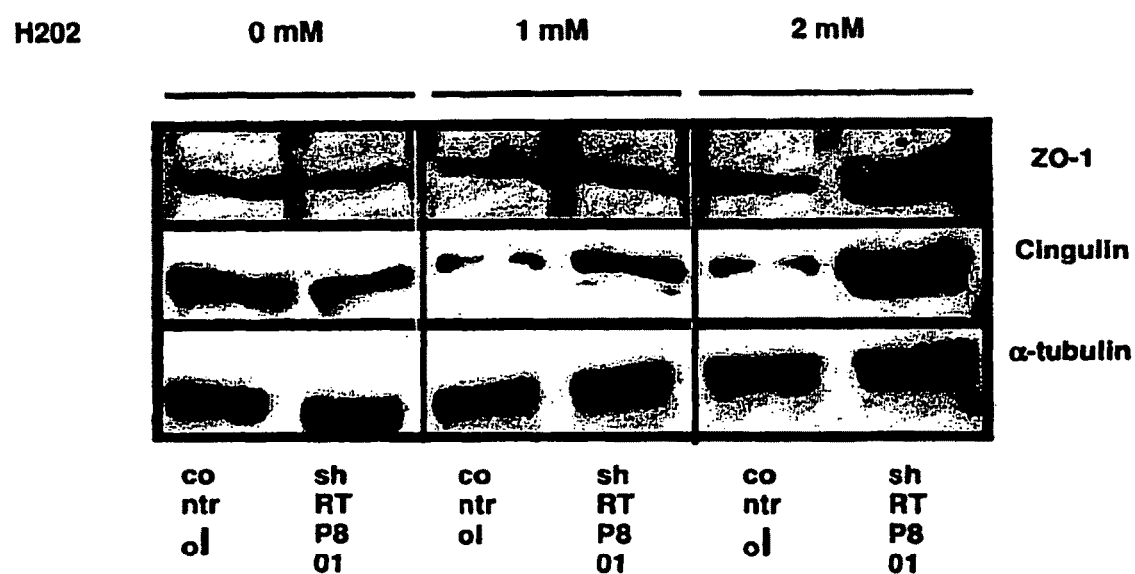
FIG. 9 demonstrates that ZO-1 and cingulin are up-regulated upon hypoxia treatment in RTP801 knock-down cells.

The present invention relates to screening systems for identifying molecules which inhibit or enhance the activity of RTP801, inter alia in its capacity to modulate apoptotic and/or neurotoxic conditions, as well as its capacity to affect the mTOR pathway. The inventors of the present invention have discovered that RTP801 self associates (forms homodimers or oligomers) and also binds to TSC1 and TSC2, said binding potentially affecting the mTOR pathway. The object of the present invention is therefore to identify molecules which may modulate this binding and/or the activity or self-association of RTP801, thereby affecting inhibition or enhancement of any of the to mTOR pathway participants, resulting in molecules which may be used to treat diseases or conditions which relate to apoptosis, ischemia or anoxia, or any other disadvantageous conditions relating to the mTOR pathway or mTOR pathway malfunction. Further, the inventors of the present invention have discovered that RTP801 binds to alpha-tubulin, said binding potentially affecting RTP801 activity in any processes which relate to cellular integrity such as, inter alia, apoptosis or anoxia. Any of the diseases and conditions mentioned herein may be treated using pharmaceutical compositions comprising the molecules identified by the methods of the present invention.

RTP801 binds RTP801 (self-association/homodimerization) and/or TSC1 and/or TSC2 and may therefore, without being bound by theory, inhibit the mTOR pathway or mTOR signalling by causing or enhancing association of the TSC complex, possibly by affecting the phosphorylation state of one or more of the complex members. Without being bound by theory, it would therefore be beneficial to enhance RTP801 activity in cases where mTOR pathway inhibition is desired and inhibit RTP801 activity in cases where mTOR pathway up-regulation is desired. RTP801 can be considered as the "glue" that strengthens the TSC complex, which in turn causes down-regulation in mTOR signaling.

As stated above, RTP801 can self associate and this self association of RTP801 has been mapped herein to a region between a.a 161-195. RTP801 self association is probably of functional significance since a deletion mutant that lacks this region and cannot self associate, is also non-functional. In addition, a 70 a.a fragment that contains this self-association region is functionally competent.

For further information concerning the mTOR pathway and the various interactors involved in said pathway, see: Jozwiak J, Jozwiak S, Grzela T, Lazarczyk M: Positive and negative regulation of TSC2 activity and its effects on downstream effectors of the mTOR pathway. Neuromolecular Med. 2005; 7(4):287-96; Brugarolas J, Lei K, Hurley L, Manning B D, Reiling J H, Hafen E, Witters L A. Ellisen L W, Kaelin W G Jr.: Regulation of mTOR function in response to hypoxia by REDD1 and the TSC1/TSC2 tumor suppressor complex. Genes Dev. 2004 Dec. 1; 18(23):2893-904; Sofer A, Lei K, Johannessen C M. Ellisen L W.: Regulation of mTOR and cell growth in response to energy stress by REDD1. Mol Cell Biol. 2005 July; 25(14):5834-45; Corradetti M N, Inoki K, Guan K L: The stress-inducted proteins RTP801 and RTP801L are negative regulators of the mammalian target of rapamycin pathway. J Biol. Chem. 2005 Mar. 18; 280(11): 9769-72.

"RTP801 gene" refers to the RTP801 coding sequence open reading frame, as shown in FIG. 1 (SEQ ID NO:1), or any homologous sequence thereof preferably having at least 70% identity, more preferable 80% identity, even more preferably 90% or 95% identity. This encompasses any sequences derived from SEQ ID NO:1 which have undergone mutations, alterations or modifications as described herein. Thus, in a preferred embodiment RTP801 is encoded by a nucleic acid sequence according to SEQ. ID. NO. 1. It is also within the present invention that the nucleic acids according to the present invention are only complementary and identical, respectively, to a part of the nucleic acid coding for RTP801 as, preferably, the first stretch and first strand is typically shorter than the nucleic acid according to the present invention. It is also to be acknowledged that based on the amino acid sequence of RTP801 any nucleic acid sequence coding for such amino acid sequence can be perceived by the one skilled in the art based on the genetic code.

"RTP801 polypeptide" refers to the polypeptide of the RTP801 gene, and is understood to include, for the purposes of the instant invention, the terms "RTP779", "REDD1", "Ddit4", "FLJ20500", "Dig2", and "PRF1", derived from any organism, optionally man, splice variants and fragments thereof retaining biological activity (such as the functional fragments disclosed herein), and homologs thereof, preferably having at least 70%, more preferably at least 80%, even more preferably at least 90% or 95% homology thereto. In addition, this term is understood to encompass polypeptides resulting from minor alterations in the RTP801 coding sequence, such as, inter alia, point mutations, substitutions, deletions and insertions which may cause a difference in a few amino acids between the resultant polypeptide and the naturally occurring RTP801. Polypeptides encoded by nucleic acid sequences which bind to the RTP801 coding sequence or genomic sequence under conditions of highly stringent hybridization, which are well-known in the art (for example Ausubel et al., Current Protocols in Molecular Biology, John Wiley and Sons, Baltimore, Md. (1988), updated in 1995 and 1998), are also encompassed by this term. Chemically modified RTP801 or chemically modified fragments of RTP801 are also included in the term, so long as the biological activity is retained, RTP801 preferably has or comprises an amino acid sequence according to SEQ. ID. NO, 2. It is acknowledged that there might be differences in the amino acid sequence among various tissues of an organism and among different organisms of one species or among different species to which the nucleic acid according to the present invention can be applied in various embodiments of the present invention. However, based on the technical teaching provided herein, the respective sequence can be taken into consideration accordingly when designing any of the nucleic acids according to the present invention. Particular fragments of RTP801 include amino acids 1-50, 51-100, 101-150, 151-200 and 201-232 of the sequence shown in FIG. 2. Further particular fragments of RTP801 include amino acids 25-74, 75-124, 125-174, 175-224 and 225-232 of the sequence shown in FIG. 2. The inventors of the present invention have discovered that RTP801 binds itself (see Example 5), and this can also be used in the screening methods of the present invention, enabling search for molecules or agents which can inhibit or enhance binding of RTP801 to itself, as described herein.

RTP801 as used herein is a protein described, among others, in WO 99/09046. RTP801 has been described as a transcriptional target of HIF-1 by Shoshani T et al. (Shoshani et al., 2002, Mol Cell Biol, 22, 2283-93). Furthermore the study by Ellisen et al. (Ellisen et al., Mol Cell, 10, 995-1005) has identified RTP801 as a p53-dependent DNA damage response gene and as a p63-dependent gene involved in epithelial differentiation. Also, RTP801 minors the tissue-specific pattern of the p53 family member p63, is effective similar to or in addition to TP 63, is an inhibitor to in vitro differentiation, and is involved in the regulation of reactive oxygen species. Apart from that, RTP801 is responsive to hypoxia-responsive transcription factor hypoxia-inducible factor 1 (HIF-1) and is typically up-regulated during hypoxia both in vitro and in vivo in an animal model of ischemic stroke. RTP801 appears to function in the regulation of reactive oxygen species (ROS) and ROS levels and reduced sensitivity to oxidative stress are both increased following ectopic expression RTP801 (Ellisen et al. 2002, supra; Soshani et al. 2002, supra). Preferably, RTP801 is a biologically active RTP801 protein which preferably exhibits at least one of those characteristics, preferable two or more and most preferably each and any of these characteristics. For the purposes of the present invention, RTP801 activity can also be defined as the ability of RTP801 to form a complex with a polypeptide, such as, inter alia, itself, TSC1, TSC2 or alpha-tubulin. Without being bound by theory, any polypeptide RTP801 forms a complex with may be involved in exerting the activity RTP801 has on various signal transduction pathways. Thus, a compound that disturbs the complex formation of RTP801 and a polypeptide such as inter alia, RTP801, TSC 1, TSC2 or alpha-tubulin, is a compound which modulates the activity of RTP801.

"TSC1 gene" refers to the TSC1 coding sequence open reading frame, as shown in FIG. 3 (SEQ ID NO:3), or any homologous sequence thereof preferably having at least 70% identity, more preferable 80% identity, even more preferably 90% or 95% identity. This encompasses any sequences derived from SEQ ID NO:3 which have undergone mutations, alterations or modifications as described herein.

"TSC2 gene" refers to the RTP801 coding sequence open reading frame, as shown in FIG. 5 (SEQ ID NO:5), or any homologous sequence thereof preferably having at least 70% identity, more preferable 80% identity, even more preferably 90% or 95% identity. This encompasses any sequences derived from SEQ ID NO:5 which have undergone mutations, alterations or modifications as described herein.

"Alpha-tubulin gene" refers to the alpha-tubulin coding sequence open reading frame, as shown in FIG. 7 (SEQ ID NO:7), or any homologous sequence thereof preferably having at least 70% identity, more preferable 80% identity, even more preferably 90% or 95% identity. This encompasses any sequences derived from SEQ ID NO:7 which have undergone mutations, alterations or modifications as described herein.

"TSC1 polypeptide" refers to the polypeptide of the TSC1 gene, also known as hamartin, derived from any organism, optionally man, splice variants and fragments thereof retaining biological activity, and homologs thereof, preferably having at least 70%, more preferably at least 80%, even more preferably at least 90% or 95% homology thereto. In addition, this term is understood to encompass polypeptides resulting from minor alterations in the TSC1 coding sequence, such as, inter alia, point mutations, substitutions, deletions and insertions which may cause a difference in a few amino acids between the resultant polypeptide and the naturally occurring TSC1. Polypeptides encoded by nucleic acid sequences which bind to the TSC1 coding sequence or genomic sequence under conditions of highly stringent hybridization which are well-known in the art (for example Ausubel et al., Current Protocols in Molecular Biology, John Wiley and Sons. Baltimore, Md. (1988), updated in 1995 and 1998), are also encompassed by this term. Chemically modified TSC1 or fragments of TSC1, which may or may not be chemically modified, are also included in the term, so long as they are still capable of binding RTP801. TSC1 preferably has or comprises an amino acid sequence according to SEQ. ID. NO. 4. It is acknowledged that there might be differences in the amino acid sequence among various tissues of an organism and among different organisms of one species or among different species to which the nucleic acid according to the present invention can be applied in various embodiments of the present invention. However, based on the technical teaching provided herein, the respective sequence can be taken into consideration accordingly when designing any of the nucleic acids according to the present invention. Particular fragments of TSC1 include amino acids 1-50, 51-100, 101-150, 151-200 and 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100 and 1101-1164 of the sequence shown in FIG. 4. Further particular fragments of TSC1 include amino acids 25-74, 75-124, 125-174, 175-224, 225-274, 275-324, 325-374, 375-424, 425-474, 475-524, 525-574, 575-624, 625-674, 675-724, 725-774, 775-824, 825-874, 875-924, 925-974, 975-1024, 1025-1074, 1075-1124 and 1125-1164 of the sequence shown in FIG. 4.

"TSC2 polypeptide" refers to the polypeptide of the TSC2 gene, also known as tuberin, derived from any organism, optionally man, splice variants and fragments thereof retaining biological activity, and homologs thereof, preferably having at least 70%, more preferably at least 80%, even more preferably at least 90% or 95% homology thereto. In addition, this term is understood to encompass polypeptides resulting from minor alterations in the TSC2 coding sequence, such as, inter alia, point mutations, substitutions, deletions and insertions which may cause a difference in a few amino acids between the resultant polypeptide and the naturally occurring TSC2. Polypeptides encoded by nucleic acid sequences which bind to the TSC2 coding sequence or genomic sequence under conditions of highly stringent hybridization, which are well-known in the art (for example Ausubel et al., Current Protocols in Molecular Biology, John Wiley and Sons, Baltimore, Md. (1988), updated in 1995 and 1998), are also encompassed by this term. Chemically modified TSC2 or fragments of TSC2, which may or may not be chemically modified, are also included in the term, so long as they are still capable of binding RTP801. TSC2 preferably has or comprises an amino acid sequence according to SEQ. ID. NO. 6. It is acknowledged that there might be differences in the amino acid sequence among various tissues of an organism and among different organisms of one species or among different species to which the nucleic acid according to the present invention can be applied in various embodiments of the present invention. However, based on the technical teaching provided herein, the respective sequence can be taken into consideration accordingly when designing any of the nucleic acids according to the present invention. Particular fragments of TSC2 include amino acids 1-50, 51-100, 101-150, 151-200 and 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750 and 1751-1807 of the sequence shown in FIG. 6. Further particular fragments of TSC2 include amino acids 25-74, 75-124, 125-174, 175-224, 225-274, 275-324, 325-374, 375-424, 425-474, 475-524, 525-574, 575-624, 625-674, 675-724, 725-774, 775-824, 825-874, 875-924, 925-974, 975-1024, 1025-1074, 1075-1124, 1125-1174, 1175-1224, 1225-1274, 1275-1324, 1325-1374, 1375-1424, 1425-1474, 1475-1524, 1525-1574, 1575-1624, 1625-1674, 1675-1724, 1725-1774 and 1775-1807 of the sequence shown in FIG. 6.

"Alpha-tubulin polypeptide" refers to the polypeptide of the alpha-tubulin gene derived from any organism, optionally man, splice variants and fragments thereof retaining biological activity, and homologs thereof, preferably having at least 70%, more preferably at least 80%, even more preferably at least 90% or 95% homology thereto. In addition, this term is understood to encompass polypeptides resulting from minor alterations in the alpha-tubulin coding sequence, such as, inter alia, point mutations, substitutions, deletions and insertions which may cause a difference in a few amino acids between the resultant polypeptide and the naturally occurring alpha-tubulin. Polypeptides encoded by nucleic acid sequences which bind to the alpha-tubulin coding sequence or genomic sequence under conditions of highly stringent hybridization, which are well-known in the art (for example Ausubel et al., Current Protocols in Molecular Biology, John Wiley and Sons, Baltimore, Md. (1988), updated in 1995 and 1998), are also encompassed by this term. Chemically modified alpha-tubulin or fragments of alpha-tubulin, which may or may not be chemically modified, are also included in the term, so long as they are still capable of binding RTP801. alpha-tubulin preferably has or comprises an amino acid sequence according to SEQ. ID. NO. 8. It is acknowledged that there might be differences in the amino acid sequence among various tissues of an organism and among different organisms of one species or among different species to which the nucleic acid according to the present invention can be applied in various embodiments of the present invention. However, based on the technical teaching provided herein, the respective sequence can be taken into consideration accordingly when designing any of the nucleic acids according to the present invention. Particular fragments of alpha-tubulin include amino acids 1-50, 51-100, 101-150, 151-200, 201-250, 251-300, 301-350, 351-400 and 401-451 of the sequence shown in FIG. 8. Further particular fragments of alpha-tubulin include amino acids 25-74, 75-124, 125-174, 175-224, 225-274, 275-324, 325-374, 375-424 and 425-451 of the sequence shown in FIG. 8.

The inventors of the present invention have discovered that alpha-tubulin binds RTP801, and thus, alpha-tubulin can be employed in screening systems aimed at identifying RTP801 modulators. Detection of the activity of RTP801 modulators can be accomplished by assaying for an RTP801-alpha-tubulin complex, or by tubulin polymerization assays.

Without being bound by theory, RTP801 being a stress-inducible protein (responding to hypoxia, oxidative stress, thermal stress, ER stress) is a factor acting in fine-tuning of cell response to energy misbalance. As such, it is a target suitable for treatment of any disease where cells should be rescued from apoptosis due to stressful conditions (e.g. diseases accompanied by death of normal cells) or where cells, which are adapted to stressful conditions due to changes in RTP801 expression (e.g. cancer cells), should be killed. In the latter case, RTP801 may be viewed as a survival factor for cancer cells and its inhibitors may treat cancer as a monotherapy or as sensitising drugs in combination with chemotherapy or radiotherapy.

The inventors of the present invention have also discovered that inhibition of RTP801 expression results in increased amounts of the tight junction proteins cingulin and ZO-1 in $H_2O_2$-treated cells (see Example 3 and FIG. 9). Further, the inventors of the present invention have also discovered that RTP801 binds cyto-keratin9. Said tight-junction proteins or cyto-keratin9 may be used in all the methods of the present invention, as output indications in screening systems alone or in conjunction with other polypeptides disclosed herein. Further, additional tight junction proteins may also be used in the same capacity if desired.

Thus, in one embodiment the present invention comprises a process for determining whether a test compound modulates the activity of an RTP801 polypeptide comprising the following steps:
a) providing an RTP801 polypeptide and a second polypeptide selected front the group consisting of RTP801, TSC1, TSC2 and alpha-tubulin;
b) treating or contacting the polypeptides of a) with the test compound;
c) determining the amount of a complex comprising the RTP801 polypeptide and the second polypeptide; and
d) comparing the amount of such complex determined in step c) with the amount determined for control polypeptides not treated or contacted with the test compound.

Optionally further wherein a difference in the amount determined in step c) with the amount determined for the control polypeptides indicates that the test compound modulates the activity of RTP801.

As discussed above, the activity of the RTP801 polypeptide encompasses its ability to form a complex with one or more polypeptide, which is optionally selected from the group consisting of RTP801, TSC1, TSC2 and alpha-tubulin. The continuing activity exerted by the formation of such a complex may relate to the mTOR pathway and/or apoptosis, inter alia., but the complex formation in itself is defined as RTP801 activity, and a compound which disturbs or disrupts the formation of such a complex thereby modulates the activity of RTP801. A compound which enhances the formation of such a complex also modulates the activity of RTP801.

Additionally, the present invention further comprises the above process wherein one or both of the polypeptides are substantially purified, or wherein the RTP801 polypeptide is a form of RTP801 comprising a tag, or wherein the second polypeptide is a form of the second polypeptide comprising a tag, or wherein the RTP801 polypeptide is a form of RTP801 comprising a first tag and the second polypeptide is a form of the second polypeptide comprising a second tag. Further, one of the polypeptides may be attached to a solid support. Any of the polypeptides provided in the above process or any other processes of the present invention may be provided in a sample, and the subsequent steps of any of these processes performed on this sample.

The present invention additionally comprises a process for determining whether a test compound modulates the activity of an RTP801 polypeptide comprising the following steps:
a) providing a cell which expresses
(i) an RTP801 polypeptide and
(ii) a second polypeptide selected from the group consisting of RTP801, TSC1, TSC2 and alpha-tubulin;
(b) treating or contacting the cell of (a) with the test compound;

(c) determining the amount of a complex comprising the RTP801 polypeptide and the second polypeptide present in the cell; and
(d) comparing the amount of such complex determined in step c) with the amount determined in a control cell not treated or contacted with the test compound.
further wherein a difference in the amount determined in step c) with the amount determined in the control cell indicates that the test compound modulates the activity of RTP801.

Additionally, a lysate may be prepared from the cell of step (b) and the detection of step (c) may be performed on the lysate. Further, a lysate may be prepared from the cell of step (a) and the treatment of step b) and detection of step (c) may be performed on the lysate.

In an additional embodiment, the present invention comprises a process for determining whether a test compound modulates the activity of RTP801 comprising the following steps:
a) providing a cell which expresses
 (i) a form of RTP801 comprising a first tag; and
 (ii) a form of a second polypeptide selected from the group consisting of RTP801, TSC1, TSC2 and alpha-tubulin, wherein the second polypeptide comprises a second tag;
(b) treating or contacting the cell of (a) with the test compound;
(c) determining the amount of a complex comprising the tagged form of RTP801 and the tagged form of the second polypeptide present in the cell; and
(d) comparing the amount of such complex determined in step c) with the amount determined in a control cell not treated or contacted with the test compound.

Optionally further wherein a difference in the amount determined in step c) with the amount determined in the control sample indicates that the test compound modulates the activity of RTP801.

Additionally, a lysate may be prepared from the cell of step (b) and the detection of step (c) may be performed on the lysate. Further, a lysate may be prepared from the cell of step (a) and the treatment of step b) and detection of step (c) may be performed on the lysate.

Further, the first tag and the second tag may interact to produce a moiety, the amount of which can be determined. Exemplary moieties are discussed further below.

The present invention additionally provides a process for determining whether a test compound modulates the activity of an RTP801 polypeptide comprising the following steps:
a) providing an RTP801 polypeptide;
(b) treating or contacting the polypeptide of a) with the test compound;
(c) determining the amount of an RTP801 polypeptide complex; and
(d) comparing the amount of such complex determined in step c) with the amount determined for a control RTP801 polypeptide not treated or contacted with the test compound.

Optionally further wherein a difference in the amount determined in step c) with the amount determined for the control polypeptides indicates that the test compound modulates the activity of RTP801.

The RTP801 polypeptide may be substantially purified; further, a portion of the RTP801 polypeptide may be a form of RTP801 comprising a tag. Additionally, a first portion of the RTP801 polypeptide may be a form of RTP801 comprising a first tag and the second portion of the RTP801 polypeptide may be a form of RTP801 comprising a second tag. Further, a portion of the RTP801 polypeptide may be attached to a solid support. Additionally, the complex formed may be a dimer.

Further provided is a process for obtaining a compound which modulates apoptosis in a cell comprising:
a) providing cells which express the human RTP801 polypeptide;
b) contacting the cells with a plurality of compounds;
c) determining which of the plurality of compounds modulates apoptosis in the cells; and
d) obtaining the compound determined to modulate apoptosis in step c).

The process may additionally comprise:
a) providing cells which express the human RTP801 polypeptide at a level such that about 50% of the cells undergo apoptosis in the presence of a known apoptosis-stimulating agent;
b) contacting the cells with the plurality of compounds;
c) treating the cells with an amount of the known apoptosis-stimulating agent so as to cause apoptosis in the cells;
d) determining which of the plurality of compounds modulates apoptosis in the cells; and
e) obtaining the compound determined to modulate apoptosis in step d).

An additionally embodiment comprises a process for obtaining a compound which modulates the activity of the RTP801 polypeptide comprising:
a) measuring the activity of the RTP801 polypeptide;
b) contacting the RTP801 polypeptide with a plurality of compounds;
c) determining which of the plurality of compounds modulates the activity of the RTP801 polypeptide; and
d) obtaining the compound determined to modulate the activity of the RTP801 polypeptide in step c).

Further provided is a process for obtaining a compound which modulates the activity of the RTP801 polypeptide comprising:
a) measuring the binding of the RTP801 polypeptide to a species with which the RTP801 polypeptide interacts;
b) contacting the RTP801 polypeptide with a plurality of compounds;
c) determining which of the plurality of compounds modulates the binding of the of the RTP801 polypeptide to the species; and
d) obtaining the compound determined to modulate the binding of the RTP801 polypeptide to the species in step c).

Additionally provided is a kit for obtaining a compound which modulates the biological activity of RTP801 comprising:
(a) RTP801; and
(b) an interactor with which RTP801 interacts.

The interactor may be selected from the group consisting of a TSC1 polypeptide, a TSC2 polypeptide and an alpha-tubulin polypeptide.

In an additional embodiment, the present invention provides a process for identifying a compound which modulates the activity of RTP801 comprising the following steps:
 a) providing a cell which expresses an RTP801 polypeptide and a second polypeptide selected from RTP801, TSC1, TSC2 and alpha-tubulin;
 (b) treating the cell of (a) with a chemical compound;
 (c) detecting the amount of a complex comprising RTP801 and the second polypeptide as compared to an untreated cell.

This process may be performed on cells or cell lysates, or alternatively in vitro using purified polypeptides instead of cells. The process would then comprise:

a) providing a purified RTP801 polypeptide
b) mixing the purified RTP801 polypeptide with a second purified polypeptide selected from RTP801, TSC1, TSC2 and alpha-tubulin;
(b) exposing the mixture of b) to a chemical compound;
(c) detecting the amount of a complex comprising RTP801 and the second polypeptide as compared to an unexposed sample.

The detection of polypeptides in any of the processes of the present invention may be performed using specific antibodies. Protein complexes may also be detected via gel electrophoresis (for example, under native conditions) or other methods known to those of skill in the art.

Additionally, as disclosed herein, the methods of the present invention may be performed using tagged polypeptides.

Thus, in another embodiment, the present invention provides a process for identifying a compound which modulates the activity of RTP801 comprising the following steps:
a) providing a cell which expresses RTP801 comprising a first tag and which also expresses a second polypeptide selected from RTP801, TSC1, TSC2 and alpha-tubulin, wherein the second polypeptide comprises a second tag;
(b) treating the cell of (a) with a chemical compound;
(c) detecting the amount of a complex comprising RTP801 and the second polypeptide as compared to a control.

Further provided is a process for identifying a compound which modulates the activity of RTP801 comprising the steps as above, wherein a lysate may be is prepared from the cell of step (b) and the detection of step (c) may be performed on the lysate. Further, a lysate may be prepared from the cell of step (a) and the treatment of step b) and detection of step (c) may be performed on the lysate.

In a particular embodiment, there is provided a process for identifying a compound which modulates the activity of RTP801 comprising the following steps:
a) providing a cell which expresses RTP801 comprising a first tag and which also expresses RTP801 comprising a second tag;
(b) treating the cell of (a) with a chemical compound;
(c) detecting the amount of an RTP801 homodimer as compared to a control cell.

Further provided is a process for identifying a compound which modulates the activity of RTP801 comprising the steps as above, wherein a lysate may be is prepared from the cell of step (b) and the detection of step (c) may be performed on the lysate. Further, a lysate may be prepared from the cell of step (a) and the treatment of step b) and detection of step (c) may be performed on the lysate.

Additionally provided is a process for identifying a compound which modulates the activity of RTP801 comprising the following steps:
a) providing purified RTP801 comprising a first tag;
b) providing purified RTP801 comprising a second tag;
(b) mixing a) and b) in vitro under binding conditions;
(c) detecting the amount of an RTP801 homodimer or oligomer as compared to a control sample.

Additionally, the present invention provides for a process for identifying a compound which modulates the activity of RTP801 comprising the following steps:
a) providing a cell which expresses RTP801 comprising a first tag and which also expresses a second polypeptide selected from RTP801, TSC1, TSC2 and alpha-tubulin, wherein the second polypeptide comprises a second tag, whereby the first and second tag interact in-vivo resulting in a detectable moiety;
b) treating the cells of step a) with a chemical compound;

c) detecting the amount of the detectable moiety in the cells or in a lysate of the cells as compared to a control.

Said detectable moiety may comprise, for example, a fluorescent molecule or protein, such as the split-YFP (BiFC) linker tagging system (Bracha-Drori et al, Plant J., 2004 November; 40(3):419-27) or fluorescence achieved in a FRET or BRET (Issad T., et al., "The use of bioluminescence resonance energy transfer for the study of therapeutic targets: application to tyrosine kinase receptors" *ert Opin Ther Targets*. 2007 April; 11(4):541-56; Koterba & Rowan, "Measuring ligand-dependent and ligand-independent interactions between nuclear receptors and associated proteins using Bioluminescence Resonance Energy Transfer (BRET)" *Nucl Recept Signal*. 2006 Jul. 26; 4:e021; Prinz A., et al., "Application of bioluminescence resonance energy transfer (BRET) for biomolecular interaction studies" *Chembiochem*. 2006 July; 7(7):1007-12) system, or a system based on an interaction detectable using, for example, western or protein blotting, such as an avidin-biotin interaction.

The control used in the processes of the present invention typically comprises an untreated cell, i.e., an identical cell which is not treated with a chemical. The control may additionally comprise a cell which does not express either TSC1, TSC2 or alpha-tubulin (or cingulin, ZO-1 or cyto-keratin9), or a cell which expresses RTP801 but does not express TSC1, TSC2 or alpha-tubulin (or cingulin, ZO-1 or cyto-keratin9), or a cell which expresses TSC1, TSC2 or alpha-tubulin (or cingulin, ZO-1 or cyto-keratin9) but does not express RTP801 respectively. Preferably, said control cell expresses the necessary endogenous level of said polypeptides, in any of the combinations described, but does not over-express one or more of the polypeptides in question. Further, the control cell may comprise a cell essentially identical in its expression profile to the treatment cell, wherein the overexpressing polypeptides in the control cell do not comprise a tag. According to the present invention, expression of RTP801 nucleic acid molecules and activity of RTP801 polypeptides are used in the screening of various compounds in order to obtain those which may be active in modulating the apoptotic process or the mTOR pathway, inter alia.

In a cell-based embodiment of this aspect of the invention, there is provided a process for obtaining a compound which modulates apoptosis in a cell comprising:
a) providing cells which express the human RTP801 polypeptide;
b) contacting said cells with said compound; and
c) determining the ability of said compound to modulate apoptosis in the cells.

The process may further comprise:
a) providing test cells and control cells which express the human RTP801 polypeptide at a level at which approximately 50% of the cells undergo apoptosis in the presence of an apoptosis-stimulating agent;
b) contacting said test cells with said compound;
c) treating said cells in conjunction with step (b) with an amount of apoptosis-stimulating agent capable of causing apoptosis in the control cell; and
d) determining the ability of said compound to modulate apoptosis in the test cell.

The process may further comprise:
a) providing a test cell which expresses the human RTP801 polypeptide and a control cell which does not express the human RTP801 polypeptide;
b) contacting said cells with said compound;
c) treating said cells in conjunction with step (b) with an amount of apoptosis-stimulating agent capable of causing apoptosis in the control cell but not in the test cell in the absence of said compound; and d) determining the ability of said compound to promote apoptosis in the test cell.

Any of the above apoptosis-based methods may also be conducted on cells which overexpress or have reduced expression of a polypeptide selected from the group consisting of TSC1, TSC2, alpha-tubulin, cingulin, ZO-1 or cytokeratin9.

In the processes of the invention, a preferred apoptosis-stimulating agent may be a Fas activating agent such as a Fas ligand or an anti-Fas activating antibody or a chemotherapeutic drug such as those described above, or an analog of one of these chemotherapeutic drugs or a chemical analog or homolog thereof, or irradiation such as gamma irradiation. Additionally, the cells used in the above assays may be stimulated by treatment with cobalt, which causes the collapse of mitochondrial function in the cells and simulates some aspects of hypoxic and/or apoptotic states.

All of the screening methods described herein may be up-scaled to a larger scale format (including an industrial up-scaling) by methods known in the art. One up-scaling possibility involves transferring all the above methods to well plates comprising 96, 192, 384 or any other number of wells, which may serve in automated versions of the methods of the present invention. Up-scaling the methods of the present invention may involve performing them on a solid support, and possibly automating various steps of the methods. Appropriate automation procedures and solid supports are known to those of skill in the art. For example, a large-scale method according to the present invention may comprise the following steps:

(a) obtaining a solid support coated with purified RTP801 polypeptide;
(b) incubating the solid support with a lysate from cells which overexpress a tagged polypeptide selected from the group consisting of RTP801, TSC1, TSC2 and alpha-tubulin;
(c) washing the solid support;
(d) treating the solid support with a molecule such as a compound, chemical, siRNA or other potentially inhibitory molecule of any kind;
(e) washing the solid support; and
(f) assaying for the ability of the molecule of step (d) to disrupt the interaction between the tagged polypeptide of step (b) and RTP801.

The purified polypeptide of step a and the tagged polypeptide of step b are interchangeable and thus, the methods may be performed with purified RTP801, TSC1, TSC2 or alpha-tubulin in step (a) and tagged RTP801 in step (b). Further, said method may be performed with any fragment of a relevant polypeptide, such as the particular fragments disclosed herein or any other biologically active fragment, i.e., a fragment that retains the relevant binding activity of the parent polypeptide.

A variety of tags for tagging polypeptides may be used with any of the methods of the present invention, such as fluorescent tags (fluorescent protein fusions, alexa dyes, cy dyes, FITC, etc.), biotin, amino acid tags (Myc, HA, 1A8, His) Flag, and GST, inter alia. The word "tag" is understood to include both cases where the mature polypeptide is bound to the tag by various chemical or biochemical means, and cases where the polypeptide is expressed as a fusion to the tag by biological means (expressed and purified from a bacterial system, or expressed directly as a fusion protein in mammalian systems).

It will be appreciated that, based on knowledge of the RTP801 polypeptide, it is possible to devise a non cell-based assay for screening for, i.e. obtaining compounds which modulate apoptosis through the human RTP801 polypeptide. An example of such a non cell-based assay is described below. Without being bound by theory, the anti-apoptotic effect of the RTP801 polypeptide may be due to the specific binding or interaction of part or all of the RTP801 polypeptide to a different species such as, without limitation, a factor, molecule, or specific binding substance, and this effect may be monitored by linking this specific binding or interaction to a signaling system. It is thus an aim of the present invention to identify compounds which, for example, modulate or disturb this specific interaction of the RTP801 polypeptide with such species.

Therefore, in a non cell-based embodiment there is provided a process for obtaining a compound which modulates apoptosis through the human RTP801 polypeptide comprising:

a) measuring activity of the human RTP801 polypeptide;
b) contacting said polypeptide with said compound; and
c) measuring the activity of said polypeptide as compared to a control.

For the purposes of this and other non-cell based assays, the activity of RTP801 may be in the modulation of apoptosis, as described herein; further, said activity may relate to the balance of reactive oxygen species in the sample being tested, or to the binding capacity of RTP801 to RTP801, TSC1, TSC2 or alpha-tubulin (or cingulin or ZO-1 or cyto-keratin9) in vitro.

Another non cell-based embodiment provides a process for obtaining a compound which modulates apoptosis through the human RTP801 polypeptide comprising:

a) measuring the binding of the human RTP801 polypeptide, or an active fragment thereof, to a species to which the human RTP801 polypeptide interacts specifically in viva to produce an effect;
b) contacting said polypeptide or fragment with said compound; and
c) determining whether the activity of said polypeptide or fragment is affected by said compound. The species may be RTP801, TSC1, TSC2 alpha-tubulin, cingulin, cyto-keratin9 or ZO-1, inter alia. Further, the effect may be an apoptosis modulation effect, an effect relating to energy metabolism or an effect on the mTOR pathway.

It is known that at times, fragments of polypeptides retain the essential biological properties of the parent, unfragmented polypeptide, and accordingly, a RTP801 DNA molecule useful in the methods of the present invention may also have a sequence encoding such fragments. Likewise, fragments of TSC1, TSC2 or alpha-tubulin may also be employed in the methods of the present invention. Preliminary results obtained by the inventors of the present invention indicate that the following fragments are useful in the screening systems of the present invention:

RTP801 N-fragment: a polypeptide comprising amino acids 1-88 of the RTP801 polypeptide, as presented in FIG. 2; this polypeptide serves as a control in TSC2 binding-based screening systems, and as a binding moiety in other screening systems.

RTP801 C-fragment: a polypeptide comprising amino acids 89-232 of the RTP801 polypeptide, as presented in FIG. 2; this polypeptide serves as a binding moiety in all the screening systems detailed herein, and may replace RTP801 in said systems, particularly those based on alpha-tubulin or TSC2 binding.

RTP801 N-C1 fragment: a polypeptide comprising amino acids 1-161 of the RTP801 polypeptide, as presented in FIG. 2.

RTP801 N-C2 fragment: a polypeptide comprising amino acids 1-195 of the RTP801 polypeptide, as presented in FIG. 2.

RTP801 C3 fragment: a polypeptide comprising amino acids 161-232 of the RTP801 polypeptide, as presented in FIG. 2.

RTP801 self association moiety: a polypeptide comprising amino acids 161-195 of the RTP801 polypeptide, as presented in FIG. 2.

TSC2 N-fragment: a polypeptide comprising amino acids 1-935 of the TSC2 polypeptide, as presented in FIG. 6; this polypeptide can serve as control or replace TSC2 in all the TSC2 based assays of the present invention.

TSC2 C-fragment: a polypeptide comprising amino acids 853-1807 of the TSC2 polypeptide, as presented in FIG. 6; this polypeptide can serve as control or replace TSC2 in all the TSC2 based assays of the present invention.

Any of the methods of the present invention can be practiced with the above fragments in lieu of their respective full-length polypeptides, as well as tagged fragments instead of tagged full-length polypeptides.

Said above fragments/polypeptides are in themselves novel and inventive and are considered per se a part of the present invention. Further details concerning the assays in which these fragments/polypeptides were used can be found in Examples 4-6.

An additional embodiment of the present invention concerns methods and processes for obtaining a species and/or chemical compound that modulates the biological activity of RTP801. One aspect of this embodiment provides a process for obtaining a species and/or chemical compound that modulates the biological activity of RTP801 which comprises contacting a cell expressing RTP801 with a species and/or compound and determining the ability of the species and/or compound to modulate the biological activity of RTP801 of the cell as compared to a control. The cell being examined may be modified to express RTP801, and—without being bound by theory—apoptosis may be induced by the presence of RTP801, or by neurotoxic stress, optionally caused by hydrogen peroxide, glutamate, dopamine, the Aβ protein or any known neurotoxin or neurotoxic treatment such as ischemia or hypoxia, or by a neurodegenerative disease such as stroke. In addition, this process may be used in order to prepare a pharmaceutical composition. The process then comprises admixing a species or compound obtained by the process recited above or a chemical analog or homolog thereof with a pharmaceutically acceptable carrier.

By cells being "modified to express" as used herein is meant that cells are modified by transfection, transduction, infection or any other known molecular biology method which will cause the cells to express the desired gene. Materials and protocols for carrying out such methods are evident to the skilled artisan.

Thus, an additional aspect of the screening embodiment provides a process of screening a plurality of species or compounds to obtain a species and/or compound that modulates the biological activity of RTP801, which comprises:
  (a) contacting cells expressing RTP801 with a plurality of species and/or chemical compounds;
  (b) determining whether the biological activity of RTP801 is modulated in the presence of the species and/or compounds, as compared to a control; and if so
  (c) separately determining whether the modulation of the biological activity of RTP801 is affected by each species and/or compound included in the plurality of species and/or compounds, so as to thereby identify the species and/or compound which modulates the biological activity of RTP801.

The cells in the contacting step may be modified to express the RTP801 polypeptide, and—without being bound by theory—apoptosis may be induced spontaneously by RTP801 overexpression, or as a result of subjection of the cells to neurotoxic stress, optionally caused by hydrogen peroxide, glutamate, dopamine, the Aβ protein or any known neurotoxin or neurotoxic treatment such as ischemic or hypoxia, or by a neurodegenerative disease such as stroke. Further, the species may be a polypeptide such as, inter alia, RTP801, TSC1, TSC2, alpha-tubulin, cingulin, cyto-keratin9 or ZO-1, or any species which is known to have activity in the mTOR pathway. In addition, this process may be used in order to prepare a pharmaceutical composition. The process then comprises admixing a species or compound identified by the process recited above or a chemical analog or homolog thereof with a pharmaceutically acceptable carrier.

The process may additionally comprise modification of a species or compound found to modulate apoptosis by the above process to produce a compound with improved activity and admixing such compound with a pharmaceutically acceptable carrier. This additional act may be performed with a compound discovered by any of the processes which are disclosed in the screening embodiment of the present invention, so as to thereby obtain a pharmaceutical composition comprising a compound with improved activity.

Additionally, the screening embodiment of the present invention provides a non cell-based process for obtaining a species or compound which modulates the biological activity of RTP801 comprising:
  (a) measuring the binding of RTP801 or the RTP801 gene to an interactor;
  (b) contacting RTP801 or the RTP801 gene with said species or compound; and
  (c) determining whether the binding of RTP801 or the RTP801 gene to said interactor is affected by said species or compound.

Said in-vitro system may be subjected to apoptotic conditions, which can be induced—without being bound by theory—by causing neurotoxic stress, as a result of treatment with, inter alia, hydrogen peroxide, glutamate, dopamine, the Aβ protein or any known neurotoxin. Further, said interactor may be RTP801, TSC1, TSC2, alpha-tubulin, cingulin, cyto-keratin9 or ZO-1, or any other interactor known to have activity in the mTOR pathway. In addition, this process may be used in order to prepare a pharmaceutical composition. The process then comprises admixing a species or compound identified by the process recited above or a chemical analog or homolog thereof with a pharmaceutically acceptable carrier.

Another aspect of the screening embodiment provided by the present invention concerns a kit for obtaining a species or compound which modulates the biological activity of RTP801 or the RTP801 gene in a cell comprising:
  (a) RTP801 or the RTP801 gene; and
  (b) an interactor with which RTP801 or the RTP801 gene interacts;
  (c) means for measuring the interaction of RTP801 or the RTP801 gene with the interactor; and
  (d) means of determining whether the binding of RTP801 or the RTP801 gene to the interactor is affected by said species or compound.

The interactor in question may be RTP801, TSC1, TSC2, cingulin, ZO-1 or cyto-keratin9; the interactor may also be a microtubule comprising or microtubule associated protein.

Means of measuring interactions between molecules and determining the strength, affinity, avidity and other parameters of the interaction are well known in the art (see, for example, Lubert Stryer, *Biochemistry*, W H Freeman & Co.; 5th edition (April 2002); and "Comprehensive Medicinal Chemistry", by various authors and editors, published by Pergamon Press).

Interaction between RTP801 and TSC1 or TSC2 can be measured by assessing the activity of the mTOR pathway.

The activity and/or status of the mTOR pathway can be assessed, inter alia, by measuring Rheb activity; activity or phosphorylation state of S6K and/or eEF2K and/or 4E-BP1; TSC2 phosphorylation and HIF accumulation. For further information see: Jozwiak J, Jozwiak S, Grzela T, Lazarczyk M: Positive and negative regulation of TSC2 activity and its effects on downstream effectors of the mTOR pathway. Neuromolecular Med. 2005; 7(4):287-96; Brugarolas J, Lei K, Hurley R L, Manning B D, Reiling J H, Hafen E, Witters L A, Ellisen L W, Kaelin W G Jr.: Regulation of mTOR function in response to hypoxia by REDD1 and the TSC1/TSC2 tumor suppressor complex. Genes Dev. 2004 Dec. 1; 18(23):2893-904; Sofer A, Lei K, Johannessen C M, Ellisen L W.: Regulation of mTOR and cell growth in response to energy stress by REDD1. Mol Cell Biol. 2005 July; 25(14):5834-45; Corradetti M N, Inoki K, Guan K L: The stress-inducted proteins RTP801 and RTP801L are negative regulators of the mammalian target of rapamycin pathway. J Biol. Chem. 2005 Mar. 18; 280(11):9769-72.

Screening Systems

The RTP801 gene or polypeptide may be used in a screening assay for identifying and isolating compounds which modulate its activity such as the methods of screening for compounds which modulate RTP801 activity as disclosed herein. Compounds which modulate RTP801 activity typically also modulate neurotoxic stress or neurodegenerative diseases, and can thus be useful in the preparation of pharmaceutical compositions aimed at treating such conditions. The compounds to be screened comprise inter alia substances such as small chemical molecules, antibodies, antisense oligonucleotides, antisense DNA or RNA molecules, polypeptides and dominant negatives, and expression vectors.

Many types of screening assays are known to those of ordinary skill in the art. The specific assay which is chosen depends to a great extent on the activity of the candidate gene or the polypeptide expressed thereby. Thus, if it is known that the expression product of a candidate gene has enzymatic activity, then an assay which is based on inhibition (or stimulation) of the enzymatic activity can be used. If the candidate polypeptide is known to bind to a ligand or other interactor, then the assay can be based on the inhibition of such binding or interaction. When the candidate gene is a known gene, then many of its properties can also be known, and these can be used to determine the best screening assay. If the candidate gene is novel, then some analysis and/or experimentation is appropriate in order to determine the best assay to be used to find inhibitors of the activity of that candidate gene. The analysis can involve a sequence analysis to find domains in the sequence which shed light on its activity.

As is well known in the art, the screening assays can be cell-based or non-cell-based. The cell-based assay is performed using eukaryotic cells such as HeLa cells, and such cell-based systems are particularly relevant in order to directly measure the activity of candidate genes which are anti-apoptotic functional genes, i.e., expression of the gene prevents apoptosis or otherwise prevents cell death in target cells. One way of running such a cell-based assay uses tetracycline-inducible (Tet-inducible) gene expression. Tet-inducible gene expression is well known in the art; see for example. Hofmann et al, 1996, Proc Natl Acad Sci 93(11): 5185-5190.

Tet-inducible retroviruses have been designed incorporating the Self-inactivating (SIN) feature of a 3' Ltr enhancer/promoter retroviral deletion mutant. Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, thus indicating that expression is regulated uniformly within the infected cell population.

If the gene product of the candidate gene phosphorylates with a specific target protein, a specific reporter gene construct can be designed such that phosphorylation of this reporter gene product causes its activation, which can be followed by a color reaction. The candidate gene can be specifically induced, using the Tet-inducible system discussed above, and a comparison of induced versus non-induced genes provides a measure of reporter gene activation.

In a similar indirect assay, a reporter system can be designed that responds to changes in protein-protein interaction of the candidate protein. If the reporter responds to actual interaction with the candidate protein, a color reaction occurs.

One can also measure inhibition or stimulation (referred to herein collectively as "modulation") of e.g., reporter gene activity, by modulation of its expression levels via the specific candidate promoter or other regulatory elements. A specific promoter or regulatory element controlling the activity of a candidate gene is defined by methods well known in the art. A reporter gene is constructed which is controlled by the specific candidate gene promoter or regulatory elements. The DNA containing the specific promoter or regulatory agent is actually linked to the gene encoding the reporter. Reporter activity depends on specific activation of the promoter or regulatory element. Thus, inhibition or stimulation of the reporter is a direct assay of stimulation/inhibition of the reporter gene; see, for example, Komarov et al (1999), Science vol 285, 1733-7 and Storz et al (1999) Analytical Biochemistry, 276, 97-104.

Various non-cell-based screening assays are also well within the skill of those of ordinary skill in the art. For example, if enzymatic activity is to be measured, such as if the candidate protein has a kinase activity, the target protein can be defined and specific phosphorylation of the target can be followed. The assay can involve either inhibition of target phosphorylation or stimulation of target phosphorylation, both types of assay being well known in the art; for example see Mohney et al (1998) J. Neuroscience 18, 5285 and Tang et al (1997) J. Clin. Invest. 100, 1180 for measurement of kinase activity. Additionally, there is a possibility that RTP801 interacts with an enzyme and regulates its enzymatic activity through protein-protein interaction.

One can also measure in vitro interaction of a candidate polypeptide with interactors. In this screen, the candidate polypeptide is immobilized on beads. An interactor, such as a receptor ligand, is radioactively labeled and added. When it binds to the candidate polypeptide on the bead, the amount of radioactivity carried on the beads (due to interaction with the candidate polypeptide) can be measured. The assay indicates inhibition of the interaction by measuring the amount of radioactivity on the bead.

Any of the screening assays, according to the present invention, can include a step of identifying the chemical compound (as described above) or other species which tests positive in the assay and can also include the further step of producing as a medicament that which has been so identified. It is considered that medicaments comprising such compounds, or chemical analogs or homologs thereof, are part of the present invention. The use of any such compounds identified for inhibition or stimulation of apoptosis is also considered to be part of the present invention.

Examples of viability assays that can be used with this bioassay include Annexin V stain (for apoptosis), and alamar blue or neutral red stains (for life/death).

An additional embodiment of the present invention concerns inhibition of the RTP801 gene or polypeptide for the treatment of eye diseases, respiratory disorders, microvascular disorders, hearing disorders and ischemic conditions, inter alia.

In addition to the above and without being bound by theory, the inventors of the present invention have found that RTP801 is involved in various disease states including microvascular disorders, eye diseases, respiratory disorders, hearing disorders, pressure sores, ischemic conditions and spinal cord injury and disease, and it would be beneficial to inhibit RTP801 in order to treat any of said diseases or disorders. Methods for identifying compounds and molecules that inhibit RTP801 are discussed herein at length, and any of said molecules and/or compositions may be beneficially employed in the treatment of a patient suffering from any of said conditions. Additionally, the molecules identified according to the methods of the present invention may potentially be used to treat patients suffering from diseases relating to abnormal function of the mTOR pathway, as well as diseases relating to abnormal TSC1 or TSC2 function such as, inter alia, tubular sclerosis.

The molecules identified according to the methods of the present invention and pharmaceutical compositions comprising them can have application in the treatment of any disease in which neuronal degeneration or damage is involved or implicated, such as, inter alia—the following conditions: hypertension, hypertensive cerebral vascular disease, a constriction or obstruction of a blood vessel—as occurs in the case of a thrombus or embolus, angioma, blood dyscrasias, any form of compromised cardiac function including cardiac arrest or failure, systemic hypotension, and diseases such as stroke, Parkinson's disease, epilepsy, depression, ALS, Alzheimer's disease, Huntington's disease and any other disease-induced dementia (such as HIV induced dementia for example). These conditions are also referred to herein as "neurodegenerative diseases". Trauma to the central nervous system, such as rupture of aneurysm, cardiac arrest, cardiogenic shock, septic shock, spinal cord trauma, head trauma, traumatic brain injury (TBI), seizure, bleeding from a tumor, etc., are also referred to herein as "injury to the central nervous system" and may also be treated using the compounds and compositions of the present invention.

The term "polynucleotide" refers to any molecule composed of DNA nucleotides, RNA nucleotides or a combination of both types, i.e. that comprises two or more of the bases guanidine, cytosine, thymidine, adenine, uracil or inosine, inter alia. A polynucleotide may include natural nucleotides, chemically modified nucleotides and synthetic nucleotides, or chemical analogs thereof. The term includes "oligonucleotides" and encompasses "nucleic acids".

The term "amino acid" refers to a molecule which consists of any one of the 20 naturally occurring amino acids, amino acids which have been chemically modified (see below), or synthetic amino acids.

The term "polypeptide" refers to a molecule composed of two or more amino acids residues. The term includes peptides, polypeptides, proteins and peptidomimetics.

A "peptidomimetic" is a compound containing non-peptidic structural elements that is capable of mimicking the biological action(s) of a natural parent peptide. Some of the classical peptide characteristics such as enzymatically scissile peptidic bonds are normally not present in a peptidomimetic. Peptidomimetics may be used in the screening systems of the present invention.

By the term "dominant negative peptide" is meant a polypeptide encoded by a cDNA fragment that encodes for a part of a protein (see Herskowitz I.: *Functional inactivation of genes by dominant negative mutations. Nature.* 1987 Sep. 17-23; 329(6136):219-22. Review; Roninson I B et al., *Genetic suppressor elements: new tools for molecular oncology*—thirteenth Cornelius P. Rhoads Memorial Award Lecture. *Cancer Res.* 1995 Sep. 15; 55(18):4023). This peptide can have a different function from the protein from which it was derived. It can interact with the full protein and inhibit its activity or it can interact with other proteins and inhibit their activity in response to the full-length (parent) protein. Dominant negative means that the peptide is able to overcome the natural parent protein and inhibit its activity to give the cell a different characteristic, such as resistance or sensitization to death or any cellular phenotype of interest. For therapeutic intervention the peptide itself may be delivered as the active ingredient of a pharmaceutical composition, or the cDNA can be delivered to the cell utilizing known methods. Dominant negative peptides may be used in the screening systems of the present invention.

Preparation of Peptides and Polypeptides

Polypeptides may be produced via several methods, for example:

1) Synthetically:

Synthetic polypeptides can be made using a commercially available machine, using the known sequence of the desired protein or a portion thereof.

2) Recombinant Methods:

A preferred method of making the desired polypeptides of fragments thereof is to clone a polynucleotide comprising the cDNA of the desired gene into an expression vector and culture the cell harboring the vector so as to express the encoded polypeptide, and then purify the resulting polypeptide, all performed using methods known in the art as described in, for example, Marshak et al., "*Strategies for Protein Purification and Characterization. A laboratory course manual*," CSHL Press (1996). (in addition, see *Bibl Haematol.* 1965; 23:1165-74 *Appl Microbiol.* 1967 July; 15(4):851-6; *Can J. Biochem.* 1968 May; 46(5):441-4; *Biochemistry.* 1968 July; 7(7):2574-80; *Arch Biochem Biophys.* 1968 Sep. 10; 126(3); 746-72; *Biochem Biophys Res Commun.* 1970 Feb. 20; 38(4):825-30)).

The expression vector can include a promoter for controlling transcription of the heterologous material and can be either a constitutive or inducible promoter to allow selective transcription. Enhancers that can be required to obtain necessary transcription levels can optionally be included. The expression vehicle can also include a selection gene.

Vectors can be introduced into cells or tissues by any one of a variety of methods known within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Vega et al., *Gene Targeting*, CRC Press, Ann Arbor, Mich. (1995), Vectors: A *Survey of Molecular Cloning Vectors and Their Uses*, Butterworths, Boston Mass. (1988) and Gilboa et al. (1986).

3) Purification from Natural Sources:

A desired polypeptide, or naturally occurring fragments thereof, can be purified from natural sources (such as tissues) using many methods known to one of ordinary skill in the art, such as for example: immuno-precipitation with an appropriate antibody, or matrix-bound affinity chromatography with any molecule known to bind the desired protein.

Protein purification is practiced as is known in the art as described in, for example. Marshak et al., "*Strategies for Protein Purification and Characterization. A laboratory course manual.*" CSHL Press (1996).

"Apoptosis" refers to a physiological type of cell death which results from activation of some cellular mechanisms, i.e. death that is controlled by the machinery of the cell. Apoptosis may, for example, be the result of activation of the cell machinery by an external trigger, e.g. a cytokine or anti-FAS antibody, which leads to cell death or by an internal signal. The term "programmed cell death" may also be used interchangeably with "apoptosis".

"Apoptosis-related disease" refers to a disease the etiology of which is related either wholly or partially to the process of apoptosis. The disease may be caused either by a malfunction of the apoptotic process (such as in cancer or an autoimmune disease) or by overactivity of the apoptotic process (such as in certain neurodegenerative diseases). Many diseases in which RTP801 is involved are apoptosis-related diseases. For example, apoptosis is a significant mechanism in dry AMD, whereby slow atrophy of photoreceptor and pigment epithelium cells, primarily in the central (macular) region of retina takes place. Neuroretinal apoptosis is also a significant mechanism in diabetic retinopathy.

An "inhibitor" is a compound which is capable of inhibiting the activity of a gene or the product of such gene to an extent sufficient to achieve a desired biological or physiological effect. An "RTP801 inhibitor" is a compound which is capable of inhibiting the activity of the RTP801 gene or RTP801 gene product, particularly the human RTP801 gene or gene product. Such inhibitors include substances that affect the transcription or translation of the gene as well as substances that affect the activity of the gene product. An RTP801 inhibitor may also be an inhibitor of the RTP801 promoter. Examples of such inhibitors may include, inter alia: polynucleotides such as AS fragments, siRNA, or vectors comprising them; polypeptides such as dominant negatives, antibodies, and enzymes; catalytic RNAs such as ribozymes; and chemical molecules with a low molecular weight e.g. a molecular weight below 2000 daltons. Specific RTP801 inhibitors are given below.

"Expression vector" refers to a vector that has the ability to incorporate and express heterologous DNA fragments in a foreign cell. Many prokaryotic and eukaryotic expression vectors are known and/or commercially available. Selection of appropriate expression vectors is within the knowledge of those having skill in the art.

The term "antibody" refers to IgG, IgM, IgD, IgA, and IgE antibody, inter alia. The definition includes polyclonal antibodies or monoclonal antibodies. This term refers to whole antibodies or fragments of antibodies comprising an antigen-binding domain, e.g. antibodies without the Fc portion, single chain antibodies, miniantibodies, fragments consisting of essentially only the variable, antigen-binding domain of the antibody, etc. The term "antibody" may also refer to antibodies against polynucleotide sequences obtained by cDNA vaccination. The term also encompasses antibody fragments which retain the ability to selectively bind with their antigen or receptor and are exemplified as follows, inter alia:

(1) Fab, the fragment which contains a monovalent antigen-binding fragment of an antibody molecule which can be produced by digestion of whole antibody with the enzyme papain to yield a light chain and a portion of the heavy chain;
(2) (Fab')$_2$, the fragment of the antibody that can be obtained by treating whole antibody with the enzyme pepsin without subsequent reduction; F(ab'$_2$) is a dimer of two Fab fragments held together by two disulfide bonds;
(3) Fv, defined as a genetically engineered fragment containing the variable region of the light chain and the variable region of the heavy chain expressed as two chains; and
(4) Single chain antibody (SCA), defined as a genetically engineered molecule containing the variable region of the light chain and the variable region of the heavy chain linked by a suitable polypeptide linker as a genetically fused single chain molecule.

By the term "epitope" as used in this invention is meant an antigenic determinant on an antigen to which the antibody binds. Epitopic determinants usually consist of chemically active surface groupings of molecules such as amino acids or sugar side chains and usually have specific three-dimensional structural characteristics, as well as specific charge characteristics.

Preparation of Antibodies

Antibodies which bind to a desired polypeptide or a fragment derived therefrom may be prepared using an intact polypeptide or fragments containing smaller polypeptides as the immunizing antigen. For example, it may be desirable to produce antibodies that specifically bind to the N- or C-terminal or any other suitable domains of the desired polypeptide. The polypeptide used to immunize an animal can be derived from translated cDNA or chemical synthesis and can be conjugated to a carrier protein, if desired. Such commonly used carriers which are chemically coupled to the polypeptide include keyhole limpet hemocyanin (KLH), thyroglobulin, bovine serum albumin (BSA) and tetanus toxoid. The coupled polypeptide is then used to immunize the animal.

If desired, polyclonal or monoclonal antibodies can be further purified, for example by binding to and elution from a matrix to which the polypeptide or a peptide to which the antibodies were raised is bound. Those skilled in the art know various techniques common in immunology for purification and/or concentration of polyclonal as well as monoclonal antibodies (Coligan et al, Unit 9, *Current Protocols in Immunology*, Wiley Interscience, 1994).

Methods for making antibodies of all types, including fragments, are known in the art (See for example, Harlow and Lane, *Antibodies: A Laboratory Manual*, Cold Spring Harbor Laboratory, New York (1988)). Methods of immunization, including all necessary steps of preparing the immunogen in a suitable adjuvant, determining antibody binding, isolation of antibodies, methods for obtaining monoclonal antibodies, and humanization of monoclonal antibodies are all known to the skilled artisan The antibodies may be humanized antibodies or human antibodies. Antibodies can be humanized using a variety of techniques known in the art including CDR-grafting (EP239, 400: PCT publication WO91/09967;U.S. Pat. Nos. 5,225, 539; 5,530,101; and 5,585,089, veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,332).

The monoclonal antibodies as defined include antibodies derived from one species (such as murine, rabbit, goat, rat, human, etc.) as well as antibodies derived from two (or more) species, such as chimeric and humanized antibodies.

Completely human antibodies are particularly desirable for therapeutic treatment of human patients. Human antibodies can be made by a variety of methods known in the art including phage display methods using antibody libraries derived from human immunoglobulin sequences. See also U.S. Pat. Nos. 4,444,887 and 4,716,111; and PCT publications WO 98/46645, WO 98/50433, WO 98/24893, WO 98/16654. WO 96/34096, WO 96/33735, and WO 91/10741, each of which is incorporated herein by reference in its entirety.

Additional information regarding all types of antibodies, including humanized antibodies, human antibodies and antibody fragments can be found in WO 01/05998, which is incorporated herein by reference in its entirety.

Neutralizing antibodies can be prepared by the methods discussed above, possibly with an additional step of screening for neutralizing activity by, for example, a survival assay.

The terms "chemical compound", "small molecule", "chemical molecule" "small chemical molecule" and "small chemical compound" are used interchangeably herein and are understood to refer to chemical moieties of any particular type which may be synthetically produced or obtained from natural sources and usually have a molecular weight of less than 2000 daltons, less than 1000 daltons or even less than 600 daltons.

Hypoxia has been recognised as a key element in the pathomechanism of quite a number of diseases such as stroke, emphysema and infarct which are associated with sub-optimum oxygen availability and tissue damaging responses to the hypoxia conditions. In fast-growing tissues, including tumor, a sub-optimum oxygen availability is compensated by undesired neoangiogenesis. Therefore, at least in case of cancer diseases, the growth of vasculature is undesired.

In view of this, the inhibition of angiogenesis and vascular growth, respectively, is subject to intense research. Already today some compounds are available which inhibit undesired angiogenesis and vascular growth. Some of the more prominent compounds are those inhibiting VEGF and the VEGF receptor. In both cases, the effect of VEGF is avoided by either blocking VEGF as such, for example by using an antibody directed against VEGF such as pursued by Genentech's AVASTIN (monoclonal AB specific for VEGF) (Ferrara N.; Endocr Rev. 2004 August; 25(4):581-611), or by blocking the corresponding receptor, i.e. the VEGF receptor (Traxler P; Cancer Res. 2004 Jul. 15; 64(14):4931-41; or Stadler W M et al., Clin Cancer Res. 2004 May 15; 10(10):3365-70).

As, however, angiogenesis and the growth of vasculature is a very basic and vital process in any animal and human being, the effect of this kind of compound has to be focused at the particular site where angiogenesis and vascular growth is actually undesired which renders appropriate targeting or delivery a critical issue in connection with this kind of therapeutic approach.

It is thus an objective of the present invention to provide further means for the treat ent of diseases involving undesired growth of vasculature and angiogenesis, respectively.

By "small interfering RNA" (siRNA) is meant an RNA molecule which decreases or silences (prevents) the expression of a gene/mRNA of its endogenous cellular counterpart. The term is understood to encompass "RNA interference" (RNAi). RNA interference (RNAi) refers to the process of sequence-specific post transcriptional gene silencing in mammals mediated by small interfering RNAs (siRNAs) (Fire et al. 1998, Nature 391, 806). The corresponding process in plants is commonly referred to as specific post transcriptional gene silencing or RNA silencing and is also referred to as quelling in fungi. The RNA interference response may feature an endonuclease complex containing an siRNA, commonly referred to as an RNA-induced silencing complex (RISC), which mediates cleavage of single-stranded RNA having sequence complementary to the antisense strand of the siRNA duplex. Cleavage of the target RNA may take place in the middle of the region complementary to the antisense strand of the siRNA duplex (Elbashir et al 2001, Genes Dev., 15, 188). For recent information on these terms and proposed mechanisms, see Bernstein E., Denli A M., Hannon G J: *The rest is silence. RNA.* 2001 November; 7(11):1509-21; and Nishikura K.: *A short primer on RNAi: RNA-directed RNA polymerase acts as a key catalyst. Cell.* 2001 Nov. 16; 107(4):415-8.

SiRNAs may be used in the screening processes of the present invention. The assignee of the present invention has found that siRNAs which inhibit the expression of the RTP801 polypeptide are useful in the treatment of various diseases and conditions. In the context of the present invention, siRNAs known to inhibit the expression of RTP801 may be used as competitive agents in the screening of chemical compounds or biological molecules which inhibit RTP801 (thereby competing with said siRNAs for RTP801 inhibition) or in the screening of chemical compounds or other molecules which enhance the expression or activity of RTP801 (thereby reversing the RTP801 inhibition effected by said siRNA molecules). For further information on RTP801 siRNAs and methods of examining the inhibition effected by these siRNAs, see PCT publication No. WO06/023544, assigned to the assignee of the present invention, which is hereby incorporated by reference in its entirety.

During recent years, RNAi has emerged as one of the most efficient methods for inactivation of genes (Nature Reviews, 2002, v. 3, p. 737-47; Nature, 2002, v. 418, p. 244-51). As a method, it is based on the ability of dsRNA species to enter a specific protein complex, where it is then targeted to the complementary cellular RNA and specifically degrades it. In more detail, dsRNAs are digested into short (17-29 bp) inhibitory RNAs (siRNAs) by type III RNAses (DICER, Drosha, etc) (Nature, 2001, v. 409, p. 363-6; Nature, 2003, 425, p. 415-9). These fragments and complementary mRNA are recognized by the specific RISC protein complex. The whole process is culminated by endonuclease cleavage of target mRNA (Nature Reviews, 2002, v. 3, p. 737-47; Curr Opin Mol. Ther. 2003 June; 5(3):217-24).

For disclosure on how to design and prepare siRNA to known genes see for example Chalk A M, Wahlestedt C, Sonnhammer E L. *Improved and automated prediction of effective siRNA* Biochem. Biophys. Res. Commun. 2004 Jun. 18; 319(1):264-74; Sioud M, Leirdal M., *Potential design rules and enzymatic synthesis of siRNAs*, Methods Mol Biol. 2004; 252:457-69; Levenkova N, Gu Q, Rux J J.: Gene specific siRNA selector Bioinformatics. 2004 Feb. 12; 20(3): 430-2. and Ui-Tei K, Naito Y, Takahashi F, Haraguchi T, Ohki-Hamazaki H, Juni A, Ueda R, Saigo K., *Guidelines for the selection of highly effective siRNA sequences for mammalian and chick RNA interference* Nucleic Acids Res. 2004 Feb. 9; 32(3):936-48. See also Liu Y, Braasch D A, Nulf C J, Corey D R. *Efficient and isoform-selective inhibition of cellular gene expression by peptide nucleic acids* Biochemistry, 2004 Feb. 24; 43(7):1921-7. See also PCT publications WO 2004/015107 (Atugen) and WO 02/44321 (Tuschl et al), and also Chiu Y L, Rana T M. siRNA function in RNAi: a chemical modification analysis, RNA 2003 September; 9(9):1034-48 and U.S. Pat. Nos. 5,898,031 and 6,107,094 (Crooke) for production of modified/more stable siRNAs.

In a preferred embodiment, the molecules identified according to the screening systems of the present invention down-regulate RTP801 function. Down-regulation of RTP801 function preferably happens by reduction in the level of expression at the protein level and/or the mRNA level, whereby such reduced level of expression, preferably at the protein level, can be as little as 5% and be as high as 100%, with reference to an expression under conditions where the nucleic acid according to the present invention is not administered or is not functionally active. Such conditions are preferably the conditions of or as present in an expression system, preferably an expression system for RTP801. Such expression system is preferably a translation system which can be an in vitro translation system, more preferably a cell, organ and/or organism. It is more preferred that the organism is a multicellular organism, more preferably a mammal, whereby such mammal is preferably selected from the group comprising man, monkey, mouse, rat, guinea pig, rabbit, cat, dog, sheep, cow, horse, cattle and pig. In connection with the down-regulation it is to be acknowledged that said down-regulation may be a function of time, i.e. the down-regulation effect is not necessarily observed immediately upon administration or functional activation of the nucleic acids according to the present invention, but may be deferred in time as well as in space, i.e. in various cells, tissues and/or organs. Such deferment may range from 5%-100%, preferably 10 to 50%. It will be acknowledged by the ones skilled in the art that a 5% reduction for a longer time period might be as effective as a 100% reduction over a shorter time period. It will also be acknowledged by the ones skilled in the art that such deferment strongly depends on the particular functional nucleic acid actually used, as well as on the target cell population and thus, ultimately, on the disease to be treated and/or prevented according to the technical teaching of the present application. repetitive It will also be acknowledged by the ones skilled in the art that the deferment can occur at any level as outlined above, i.e. a deferment in function, whereby such function is any function exhibited by RTP801, a deferment in protein expression or a deferment at mRNA expression level.

When a nucleic acid to be employed in the processes of the present invention is manufactured or expressed, preferably expressed in vivo, such manufacture or expression preferably uses an expression vector, preferably a mammalian expression vector. Expression vectors are known in the art and preferably comprise plasmids, cosmids, viral expression systems. Preferred viral expression systems include, but are not limited to, adenovirus, retrovirus and lentivirus.

Methods are known in the art to introduce the vectors into cells or tissues. Such methods can be found generally described in Sambrook et al., Molecular cloning: A Laboratory Manual, Cold Springs Harbour Laboratory, New York (1983, 1992), or in Ausubel et al., Current Protocols in Molecular Biology, John Wiley and Sons, Baltimore, Md. 1998.

Suitable methods comprise, among others, transfection, lipofection, electroporation and infection with recombinant viral vectors. In connection with the present invention, an additional feature of the vector is in one embodiment an expression limiting feature such as a promoter and regulatory element, respectively, that are specific for the desired cell type thus allowing the expression of the nucleic acid sequence according to the present invention only once the background is provided which allows the desired expression.

In a further aspect the present invention is related to a pharmaceutical composition comprising a molecule identified according to the methods of the present invention and/or a vector according to the present invention and, optionally, a pharmaceutically acceptable carrier, diluent or adjuvants or other vehicle(s). Preferably, such carrier, diluents, adjuvants and vehicles are inert, and non-toxic. The pharmaceutical composition is in its various embodiments adapted for administration in various ways. Such administration comprises systemic and local administration as well as oral, subcutaneous, parenteral, intravenous, intraarterial, intramuscular, intraperitoneal, intranasal, and intrategral.

It will be acknowledged by the ones skilled in the art that the amount of the pharmaceutical composition and the respective nucleic acid and vector, respectively, depends on the clinical condition of the individual patient, the site and method of administration, scheduling of administration, patient age, sex, bodyweight and other factors known to medical practitioners. The pharmaceutically effective amount for purposes of prevention and/or treatment is thus determined by such considerations as are known in the medical arts. Preferably, the amount is effective to achieve improvement including but limited to improve the diseased condition or to provide for a more rapid recovery, improvement or elimination of symptoms and other indicators as are selected as appropriate measures by those skilled in the medical arts.

In a preferred embodiment, the pharmaceutical composition according to the present invention may comprise other pharmaceutically active compounds. Preferably, such other pharmaceutically active compounds are selected from the group comprising compounds which allow for uptake intracellular cell delivery, compounds which allow for endosomal release, compounds which allow for, longer circulation time and compounds which allow for targeting of endothelial cells or pathogenic cells. Preferred compounds for endosomal release are chloroquine, and inhibitors of ATP dependent $H^+$ pumps.

The pharmaceutical composition is preferably formulated so as to provide for a single dosage administration or a multi-dosage administration.

It will be acknowledged that the pharmaceutical composition according to the present invention can be used for any disease which involves undesired development or growth of vasculature including angiogenesis, as well as any of the diseases and conditions described herein. Preferably, these kind of diseases are tumor diseases. Among tumor diseases, the following tumors are most preferred: endometrial cancer, colorectal carcinomas, gliomas, endometrial cancers, adenocarcinomas, endometrial hyperplasias, Cowden's syndrome, hereditary non-polyposis colorectal carcinoma, Li-Fraumene's syndrome, breast-ovarian cancer, prostate cancer (Ali, I. U., Journal of the National Cancer Institute, Vol. 92, no. 11, Jun. 7, 2000, page 861-863), Bannayan-Zonana syndrome, LDD (Lhermitte-Duklos' syndrome) (Macleod, K., supra) hamartoma-macrocephaly diseases including Cow disease (CD) and Bannayan-Ruvalcaba-Rily syndrome (BRR), mucocutaneous lesions (e.g. trichilemmonmas), macrocephaly, mental retardation, gastrointestinal harmatomas, lipomas, thyroid adenomas, fibrocystic disease of the breast, cerebellar dysplastic gangliocytoma and breast and thyroid malignancies (Vazquez, F., Sellers, W. R., supra).

The pharmaceutical composition according to the present invention can also be used in a method for preventing and/or treating a disease as disclosed herein, whereby the method comprises the administration of a pharmaceutical composition or medicament comprising a molecule identified according to the methods or processes of present invention for any of the diseases described herein. Additional pharmacological considerations, formulations and delivery modes are disclosed in PCT Publication No. WO06/023544A2, assigned to assignee of the instant application.

The synthesis of any of the nucleic acids described herein is within the skills of the one of the art. Such synthesis is, among others, described in Beaucage S. L. and Iyer R. P., Tetrahedron 1992; 48: 2223-2311, Beaucage S. L. and Iyer R. P., Tetrahedron 1993; 49: 6123-6194 and Caruthers M. H. et. al., Methods Enzymol. 1987; 154: 287-313, the synthesis of thioates is, among others, described in Eckstein F., Annu. Rev. Biochem. 1985; 54: 367-402, the synthesis of RNA molecules is described in Sproat B., in Humana Press 2005 Edited by Herdewijn P.; Kap. 2: 17-31 and respective downstream processes are, among others, described in Pingoud A. et. al., in IRL Press 1989 Edited by Oliver R. W. A.; Kap. 7: 183-208 and Sproat B., in Humana Press 2005 Edited by Herdewijn P.; Kap. 2: 17-31 (supra).

All analogues of, or modifications to, a polynucleotide may be employed with the present invention, provided that said analogue or modification does not substantially affect the function of the polynucleotide. The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiouracil, 8-halo adenine, 8-aminoadenine, 8-thiol adenine, 8-thioalkyl adenines, 8-hydroxyl adenine and other 8-substituted adenines, 8-halo guanines. 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of polynucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones.

The polypeptides employed in the present invention may also be modified, optionally chemically modified, in order to improve their therapeutic activity. "Chemically modified"—when referring to the polypeptides, means a polypeptide where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Additional possible polypeptide modifications (such as those resulting from nucleic acid sequence alteration) include the following:

"Conservative substitution"—refers to the substitution of an amino acid in one class by an amino acid of the same class, where a class is defined by common physicochemical amino acid side chain properties and high substitution frequencies in homologous polypeptides found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His. Arg, Lys); Class V (Ile, Leu, Val, Met); and Class VI (Phe, Tyr, Trp). For example, substitution of an Asp for another class III residue such as Asn, Gln, or Glu, is a conservative substitution.

"Non-conservative substitution"—refers to the substitution of an amino acid in one class with an amino acid from another class; for example, substitution of an Ala, a class II residue, with a class III residue such as Asp, Asn, Glu, or Gln.

"Deletion"—is a change in either nucleotide or amino acid sequence in which one or more to nucleotides or amino acid residues, respectively, are absent.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively. As regards amino acid sequences the substitution may be conservative or non-conservative.

By "homolog/homology", as utilized in the present invention, is meant at least about 70%, preferably at least about 75% homology, advantageously at least about 80% homology, more advantageously at least about 90% homology, even more advantageously at least about 95%, e.g., at least about 97%, about 98%, about 99% or even about 100% homology. The invention also comprehends that these polynucleotides and polypeptides can be used in the same fashion as the herein or aforementioned polynucleotides and polypeptides.

Alternatively or additionally, "homology", with respect to sequences, can refer to the number of positions with identical nucleotides or amino acid residues, divided by the number of nucleotides or amino acid residues in the shorter of the two sequences, wherein alignment of the two sequences can be determined in accordance with the Wilbur and Lipman algorithm ((1983) Proc. Natl. Acad. Sci. USA 80:726); for instance, using a window size of 20 nucleotides, a word length of 4 nucleotides, and a gap penalty of 4, computer-assisted analysis and interpretation of the sequence data, including alignment, can be conveniently performed using commercially available programs (e.g., Intelligenetics™ Suite, Intelligenetics Inc., CA). When RNA sequences are said to be similar, or to have a degree of sequence identity or homology with DNA sequences, thymidine (T) in the DNA sequence is considered equal to uracil (U) in the RNA sequence. RNA sequences within the scope of the invention can be derived from DNA sequences or their complements, by substituting thymidine (T) in the DNA sequence with uracil (U).

Additionally, or alternatively, amino acid sequence similarity or homology can be determined, for instance, using the BlastP program (Altschul et al., Nucl. Acids Res. 25:3389-3402) and available at NCBI. The following references provide algorithms for comparing the relative identity or homology of amino acid residues of two polypeptides, and additionally, or alternatively, with respect to the foregoing, the teachings in these references can be used for determining percent homology: Smith et al., (1981) Adv. Appl. Math. 2:482-489; Smith et al., (1983) Nucl. Acids Res. 11:2205-2220; Devereux et al., (1984) Nucl. Acids Res. 12:387-395; Feng et al., (1987) J. Molec. Evol. 25:351-360; Higgins et al., (1989) CABIOS 5:151-153; and Thompson et al., (1994) Nucl. Acids Res. 22:4673-4680.

"Having at least X % homolgy"—with respect to two amino acid or nucleotide sequences, refers to the percentage of residues that are identical in the two sequences when the sequences are optimally aligned. Thus, 90% amino acid sequence identity means that 90% of the amino acids in two or more optimally aligned polypeptide sequences are identical.

EXAMPLES

Without further elaboration, it is believed that one skilled in the art can, using the preceding description, utilize the present invention to its fullest extent. The following preferred specific embodiments are, therefore, to be construed as merely illustrative, and not imitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988).

Standard organic synthesis protocols known in the art not specifically described herein are generally followed essentially as in *Organic syntheses*: Vol. 1-79, editors vary, J. Wiley, New York, (1941-2003); Gewert et al., *Organic synthesis workbook*, Wiley-VCH, Weinheim (2000); Smith & March, *Advanced Organic Chemistry*, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

The features of the present invention disclosed in the specification, the claims and/or the drawings may both separately and in any combination thereof be material for realizing the invention in various forms thereof.

Example 1

General Materials and Methods

If not indicated to the contrary, the following materials and methods were used in Examples 1-5:

Cell Culture

The first human cell line, namely HeLa cells (American Type Culture Collection) were cultured as follows: Hela cells (American Type Culture Collection) were cultured as described in Czauderna F et al. (Czauderna, F., Fechtner, M. Aygun, H., Arnold, W., Klippel, A., Giese, K. & Kaufmann, J. (2003). Nucleic Acids Res, 31, 670-82).

The second human cell line was a human keratinocyte cell line which was cultivated as follows: Human keratinocytes were cultured at 37° C. in Dulbecco's modified Eagle medium (DMEM) containing 10% FCS.

The mouse cell line was B 16V (American Type Culture Collection) cultured at 37° C. in Dulbecco's modified Eagle medium (DMEM) containing 10% FCS. Culture conditions were as described in Methods Find Exp Clin Pharmacol. 1997 May; 19(4):231-9:

In each case, the cells were subject to the experiments as described herein at a density of about 50,000 cells per well and the double-stranded nucleic acid according to the present invention was added at 20 nM, whereby the double-stranded nucleic acid was complexed using 1 µg/ml of a proprietary lipid.

Induction of Hypoxia-Like Condition

The cells were treated with $CoCl_2$ for inducing a hypoxia-like condition as follows: siRNA transfections were carried out in 10-cm plates (30-50% confluency) as described by (Czauderna et al., 2003; Kretschmer et al., 2003). Briefly, siRNA were transfected by adding a preformed 10× concentrated complex of GB and lipid in serum-free medium to cells in complete medium. The total transfection volume was 10 ml. The final lipid concentration was 1.0 µg/ml; the final siRNA concentration was 20 nM unless otherwise stated. Induction of the hypoxic responses was carried out by adding $CoCl_2$ (100 µM) directly to the tissue culture medium 24 h before lysis.

Preparation of Cell Extracts and Immuno Blotting

The preparation of cell extracts and immuno blot analysis were carried out essentially as described by Klippel et al. (Klippel, A., Escobedo, M. A., Wachowicz, M. S., Apell, G., Brown, T. W., Giedlin, M. A., Kavanaugh, W. M. & Williams, L. T. (1998). Mol Cell Biol, 18, 5699-711; Klippel, A., Reinhard, C., Kavanaugh, W. M., Apell, G. Escobedo, M. A. & Williams, L. T. (1996). Mol Cell Biol, 16, 4117-27). Polyclonal antibodies against full length RTP801 were generated by immunizing rabbits with recombinant RTP801 protein producing bacteria from pET19-b expression vector (Merck Biosciences GmbH, Schwalbach, Germany). The murine monoclonal anti-p110a and anti-p85 antibodies have been described by Klippel et al. (supra).

Example 2

Experimental Models and Methods

In-vivo and in-vitro models which are useful in the identification of compounds which modulate RTP801 and animal models which can be used for validation of the activity of said identified compounds and their therapeutic potential are disclosed in PCT Publication No. WO06/023544A2 and PCT application No. PCT/US2007/01468, assigned to assignee of the instant application.

Example 3

Experimental Methods Used to Identify Tight-Junction Proteins

Permeability Experiments

EOMA cells stably infected with Lentivirus encoding shRNA 14 (aka REDD14, which decreases levels of the RTP801 polypeptide) and Lentivirus controls (empty vector; Luciferase shRNA encoding vector and "Yeast" siRNA encoding vector) were used in the experiment. Permeability was measured using the kit "*In vitro Vascular Permeability Assay Kit*" ECM640, Chemicon. Cells were grown in an collagen-coated inserts, seeding density—100.000/insert. Growth—4 days, in DMEM medium with 10% FCS. H2O2 (1-2 mM) was added after 4 d of growth for 2 h. Then medium was replaced with fresh medium containing FITC-dextran. Incubation was continued for 10-40 min and aliquots were taken for fluorescence measurements (485-530 nM)

Western Blotting

Cells were grown in 6 well plates in similar conditions as above (+/−H2O2), and were lysed in RIPA buffer containing protease inhibitor cocktail and phosphatase inhibitors.

Protein extracts were separated on 6% PAGE-SOS gel and transferred onto nitrocellulose membrane.

The membrane was probed using anti-ZO-1 sc-8146 (Santa Cruz) and anti-Cingulin 36-4401 (Zymed).

The results are presented in FIG. 9 and demonstrate that down-regulation of RTP801 (using shRNA) causes up-regulation of ZO-1 and cingulin in response to hypoxia.

Example 4

Experimental Results

A) Co-Immuno Precipitation

Description: 293T cells were transiently transfected with either empty plasmid or with plasmid containing FLAG-hRTP801 or FLAG-hRTP801-L cDNAs. 48 hrs. post-transfection, cobalt chloride (150 uM) was added (or omitted) for another 24 hrs. Cytosolic extracts prepared and IP was done using anti-FLAG antibodies. Alternatively, 293T cells were transiently transfected with plasmid containing FLAG-hRTP801 cDNA and plasmid containing TSC1 or TSC2 cDNAs or both. 48 hrs. post transfection, cobalt chloride (150 uM) was added for another 24 hrs. Cytosolic extracts prepared and IP was done using anti-TSC1, anti-TSC2 or normal rabbit IgG (NRIgG) antibodies. Alternatively, 293T cells were transiently transfected with either empty plasmid, plasmid containing FLAG-hRTP801 cDNA and plasmids containing either TSC1 and/or TSC2 cDNAs. 48 hrs. post transfection, cobalt chloride (150 uM) was added for another 24 his. Cytosolic extracts prepared and IP was done using anti-FLAG antibodies. Immunocomplexes were analysed by immunoblotting with the indicated antibodies (see FIGS. 10-13).

Figure 11:
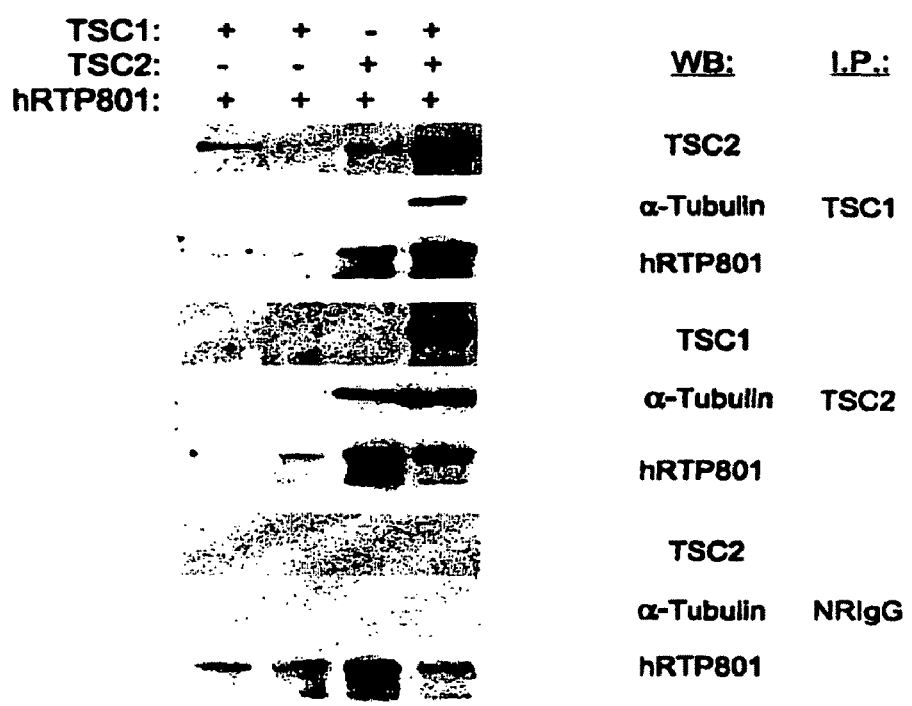
FIG. 11 shows co-immunoprecipitation of exogenous TSC2 with alpha tubulin and RTP801.
Figure 12:
FIG. 12 hRTP801 co-IP with tubulin independently of exogenous TSC2—demonstrates that RTP801 co-immunoprecipitates with tubulin independently of exogenous TSC2.

The results are presented in FIGS. 10-12. FIG. 10 demonstrates that alpha/beta tubulin and cytokeratin-9 co-immunoprecipitate with RTP801. FIG. 11 demonstrates that TSC2 co-immunoprecipitates with alpha tubulin and RTP801. FIG. 12 demonstrates that RTP801 co-immunoprecipitates with tubulin independently of exogenous TSC2.

B) "Pull-Down" Experiments

Description: Recombinant hRTP801 (purified as a GST-fusion protein from bacteria) as well as free GST were used to capture interacting proteins from cell extract. GST or GST-hRTP801 were immobilized on glutathione beads and similar amount of each protein was incubated with various 293T cell extracts. Elution was done using reduced glutathione. Binding of TSC2 or alpha tubulin was assessed by Western Blotting with specific antibodies.

Figure 13:
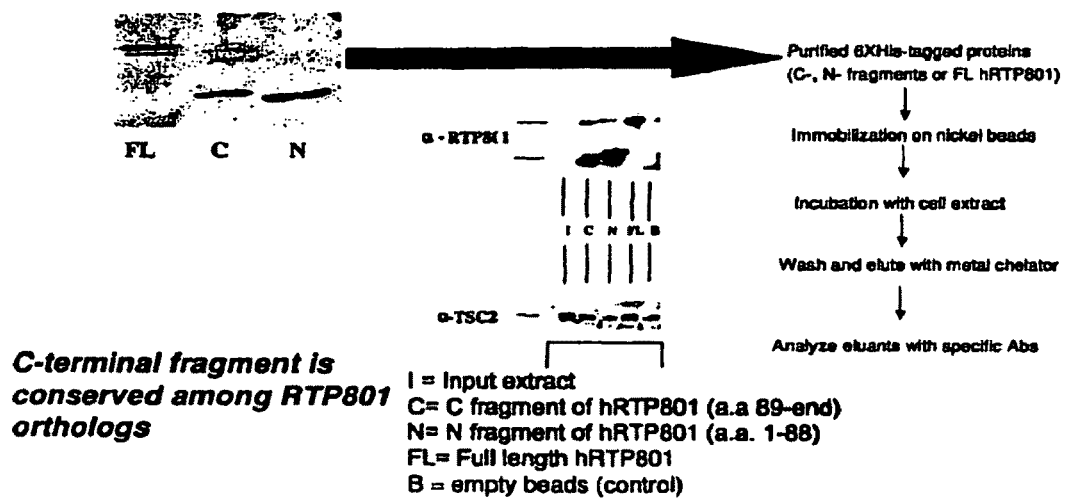
FIG. 13 binding in vitro of 6XHis-hRTP801 and 6XHis-hRTP801 C-fragment (but not 6XHis hRTP801 N-fragment) to TSC2 ("pull-down" from extract)—shows binding in vitro of RTP801 and RTP801 C-fragment (but not RTP801 N-fragment) to TSC2.
Figure 14A:
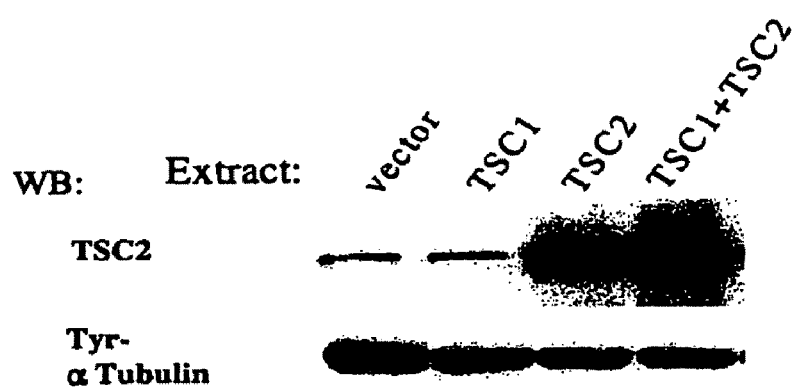
FIG. 14 binding in vitro of GST-hRTP801 (but not of free GST to TSC2 and to tubulin). A. Input extracts used for experiment B. Pull down result—demonstrates binding in vitro of GST-hRTP801 but not of free GST) to TSC2 and to tubulin.
Figure 14B:
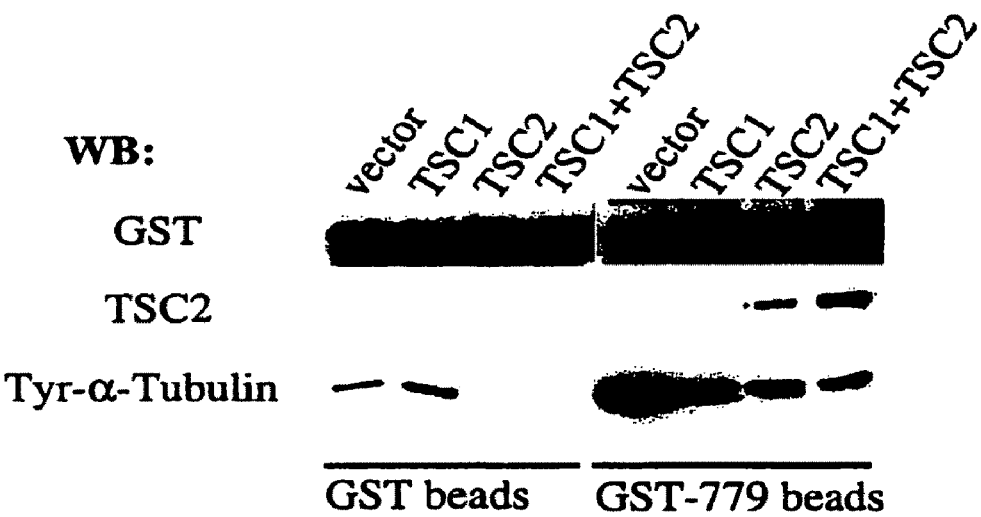
Figure 15B:
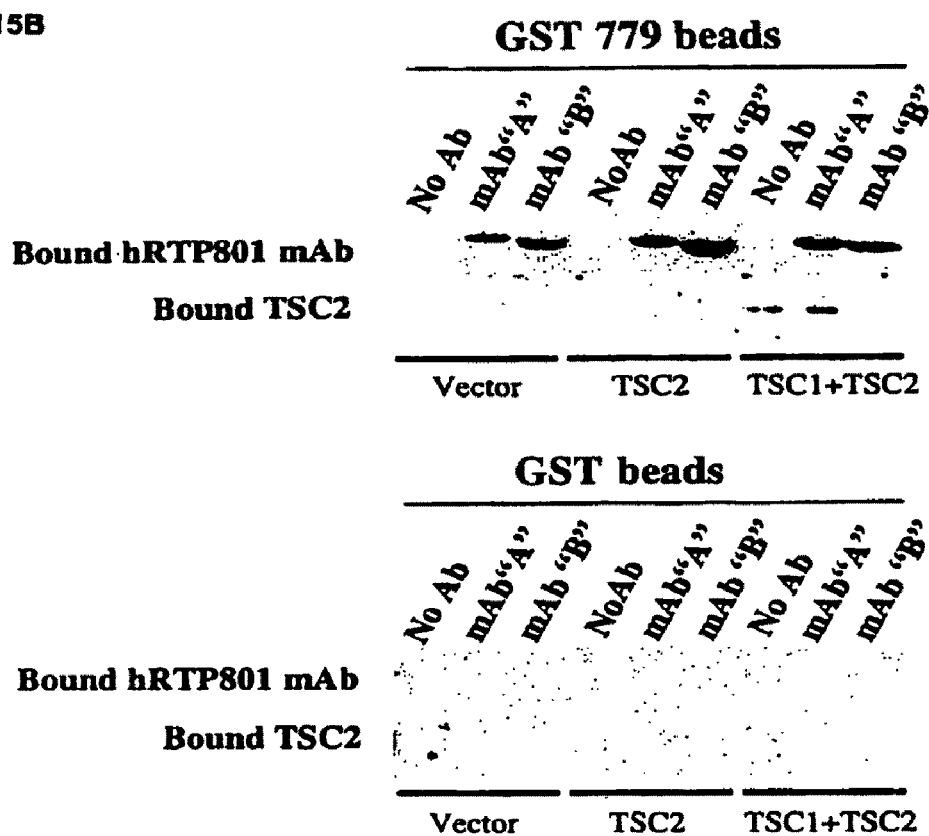
FIG. 15 monoclonal anti-hRTP801 C-fragment (termed mAb "B") abolishes binding in vitro of GST-hRTP801 to TSC2 whereas monoclonal anti-hRTP801 N-fragment (termed mAb "A") has no effect. A. Specificity of mAbs as judged by ELISA. B. Effect of pre-incubation with mAbs "A" or "B" on binding of GST-hRTP801 to TSC2, shows that monoclonal anti-hRTP801 C-fragment abolishes binding in vitro of GST-hRTP801 to TSC2 whereas monoclonal anti-hRTP801 N-fragment has no effect.
Figure 16:
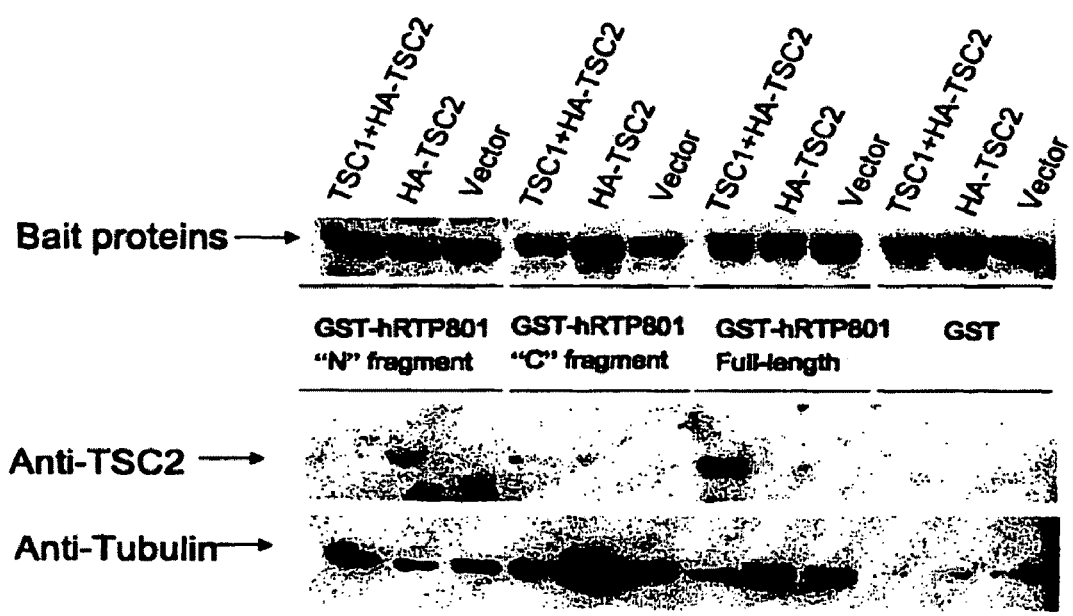
FIG. 16 demonstrates that binding of TSC2 to RTP801 occurs within the C-fragment while binding of alpha tubulin to hRTP801 requires both C- and N-fragments.

The results are presented in FIGS. 13-16. FIG. 13 demonstrates that RTP801 and RTP801 C-fragment but not RTP801 N-fragment bind TSC2 in vitro ("pull-down" from extract). FIG. 14 demonstrates that GST-RTP801 (but not free GST) binds to TSC2 and Tubulin in vitro. A. shows the Input extracts used for the experiment, while B. shows the pull-down results. FIG. 15 demonstrates that Monoclonal anti-hRTP801 C-fragment (termed mAb "B") abolishes binding in vitro of GST-hRTP801 to TSC2 whereas monoclonal anti-hRTP801 N-fragment (termed mAb "A") has no effect. A. Specificity of mAbs as judged by ELISA. B. Effect of pre-incubation with mAbs "A" or "B" on binding of GST-hRTP801 to TSC2. FIG. 16 demonstrates that binding of TSC2 to hRTP801 occurs within the C-fragment while binding of alpha tubulin to hRTP801 requires both C- and N-fragments.

C) Identification of TSC2 Fragment Sufficient for Interaction with RTP801

Description: 293T cells were transfected with plasmid containing FLAG-hRTP801 cDNA and one of the constructs shown in the figure. Cytosolic extracts were prepared and IP was done using anti-FLAG antibodies. Analysis of the immunocomplexes was done with anti-HA.

Figure 17:
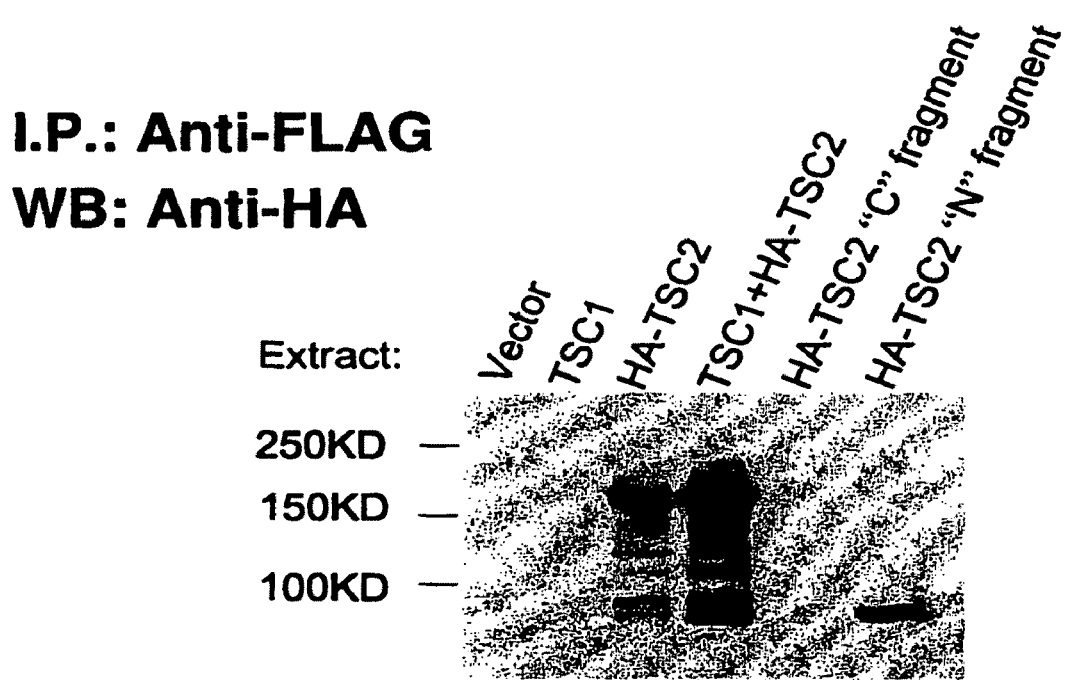
FIG. 17 shows that TSC2 "N" fragment (a.a. 2-935) is sufficient for interaction with FLAG-hRTP801.

The results, showing that TSC2"N" fragment (a.a. 2-935) is sufficient for interaction with FLAG-hRTP801, are presented in FIG. 17.

D) Up-Scaling of an Exemplary Screening Assay

Description: Purified hRTP801 (or as GST-hRTP801) is used to coat multi-well plates. Coating can either be directly or via anti-GST antibodies that are easily produced. Following a blocking step, small molecules are introduced followed by addition of extract from cells that express tagged TSC2 or TSC1/TSC2 complex. Following washes, bound TSC2 can be tested via its tag by an ELISA-based protocol. Wells which have a reduced signal contain inhibitory compounds which are thus identified.

Figure 18:
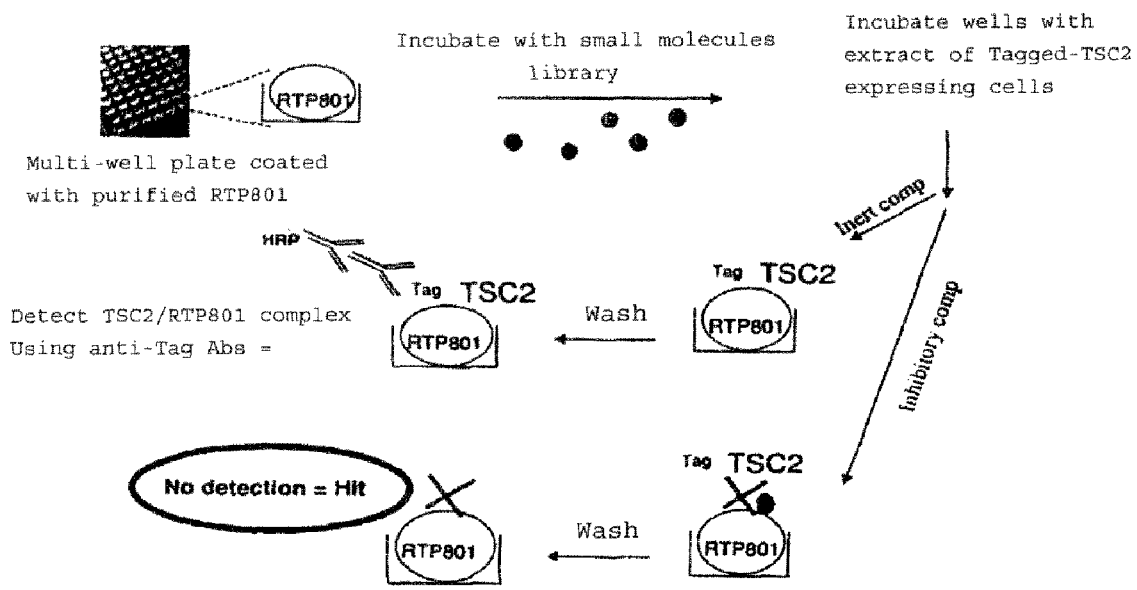
FIG. 18 schematic description of suggested ELISA-based assay for discovery of small molecules that can inhibit hRTP801/TSC2 complex—depicts a schematic description of an exemplary ELISA-based assay for discovery of small molecules that can inhibit the RTP801/TSC2 complex.

FIG. 18 is a schematic description of suggested ELISA-based assay for discovery of small molecules that can inhibit hRTP801/TSC2 complex.

Figure 19:
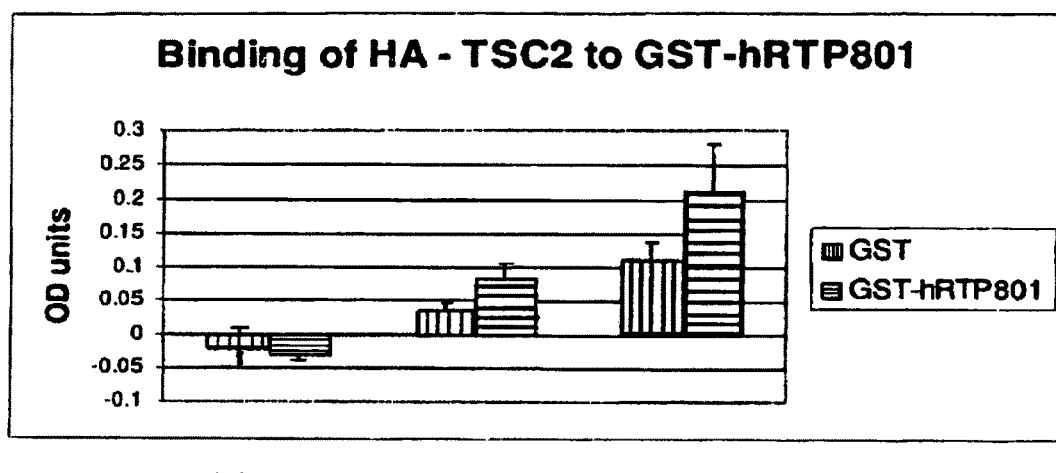
FIG. 19 shows that binding of HA-tagged TSC2 to GST-hRTP801 can be detected using an ELISA-based assay.

The validation results demonstrated in FIG. 19 show that Binding of HA-tagged TSC2 to GST-hRTP801 can be detected using an ELISA-based assay (as described above).

E) Binding of Purified Tubulin to RTP801

Description: Binding to purified tubulin (Cytoskeleton Inc.) was done essentially as described in Chen et al., JBC Vol. 281, pp. 7983-7993.

Figure 20A:
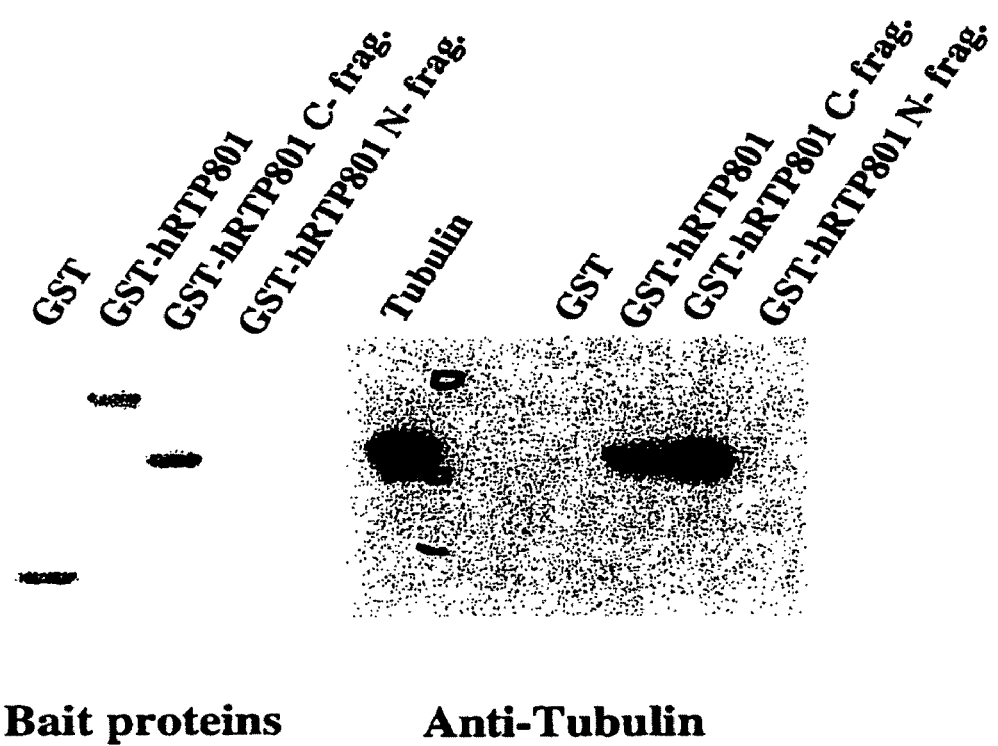
FIG. 20 binding of purified tubulin to GST-hRTP801, GST-hRTP C-frag. and GST-hRTP801 N-frag. but not to free GST. A. Purified tubulin binds to both full hRTP801 and to its C-frag. B. Purified tubulin binds the hRTP801 N-frag.—demonstrates binding of purified tubulin of purified tubulin to RTP801.

The results are presented in FIG. 20. Binding of purified tubulin to GST-hRTP801, GST-hRTP C-frag. and GST-hRTP801 N-frag. but not to free GST. A. Purified tubulin binds to both full hRTP801 and to its C-frag. A second experiment performed with a higher amount of the N-frag. Shows that the N-frag. also binds tubulin (B.).

In Summary:
- Alpha/beta tubulin and cytokeratin 9 were discovered to be proteins that co-immuno precipitate with FLAG-hRTP801.
- FLAG-hRTP801 and FLAG-hRTP801-L co-immuno precipitate with endogenous alpha tubulin and TSC2
- Exogenous TSC2 co-immuno precipitates with alpha tubulin and FLAG-hRTP801
- hRTP801 co-immuno precipitates with tubulin independently of exogenous TSC2
- TSC2 binds in vitro to 6XHis-hRTP801 and 6XHis-hRTP801 C-fragment (hut not 6XHis hRTP801 N-fragment)("pull-down" from extract)
- TSC2 and to tubulin bind in vitro to GST-hRTP801 (but not of free GST).
- Monoclonal anti-hRTP801 C-fragment (termed mAb "A") abolishes binding in vitro of GST-hRTP801 to TSC2 whereas monoclonal anti-hRTP801 N-fragment (termed mAb "B") has no effect.
- Binding of TSC2 to hRTP801 occurs at the C-fragment while binding of alpha tubulin to hRTP801 requires both C- and N-fragments.
- TSC2 "N" fragment (a.a. 2-935) is sufficient for interaction with FLAG-hRTP801.
- GST-hRTP801 (full length, C-fragment and N-fragment) Binds in vitro to purified brain tubulin
- ELISA-format assay is effective for measuring thr binding of HA-TSC2 to GST-hRTP801.

Example 5

Further Experimental Results Relating To RTP801 Self-Association

A) hRTP801 Self Associates and the Region Between a.a 161-195 is Essential for Self-Association 293T HEK cells were co-transfected with a plasmid containing cDNA of HA-SV5-full length hRTP801 ("Prey") as well as plasmid containing cDNA of one of the following: FLAG-full length hRTP801, FLAG-(C) hRTP801, FLAG-(N-C1) hRTP801, FLAG-(N-C1) hRTP801, FLAG-(N-C2) hRTP801 and FLAG-(C3) hRTP801. Forty-eight hours after transfection, cells were treated with 150 uM cobalt chloride for 18 hrs to mimic hypoxic stress conditions. The next day, cytosolic extracts were made by mechanic lysis under hypotonic conditions. FLAG-tagged bait proteins were immunoprecipitated with M2 anti-FLAG resin (Sigma). Following extensive washing, immunoprecipitated material was analyzed by immunoblotting with either anti-hRTP801 polyclonal antibodies (proprietary) or with anti-SV5 polyclonal antibodies (AbCam).

Figure 21A:
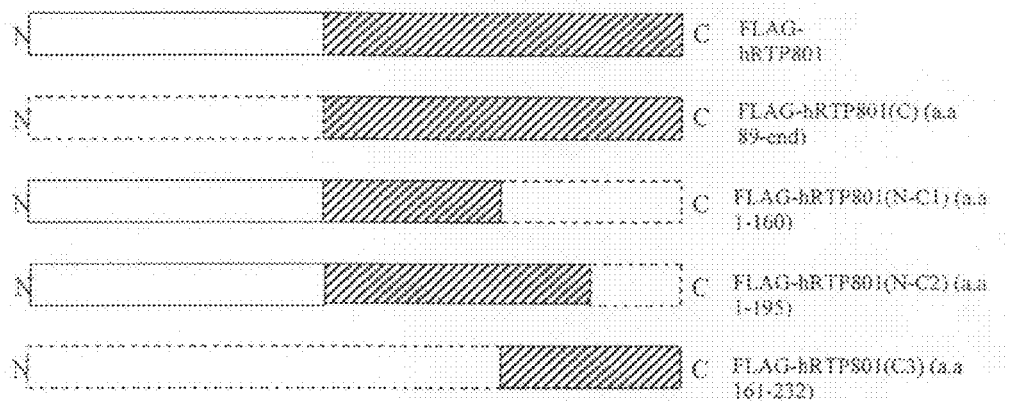
FIG. 21 shows that full length RTP801 co-immunoprecipitated with FLAG-hRTP801, indicating self association of hRTP801.
Figure 21B:
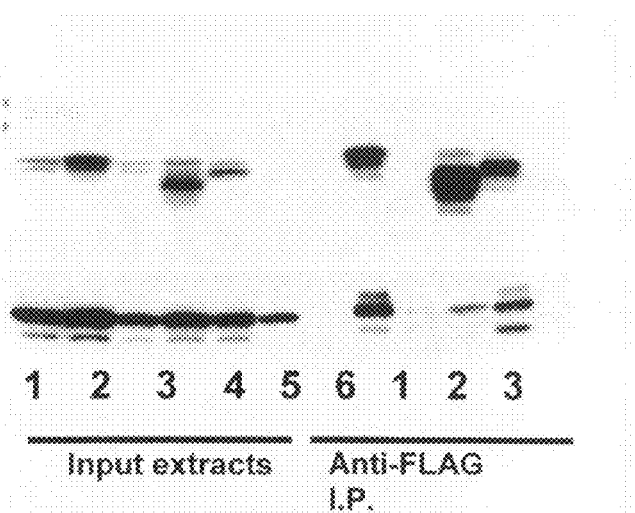

As shown in FIG. 21, HA-full length hRTP801 co-immuno-precipitated with FLAG-hRTP801, indicating self association of hRTP801 (lane 2, right panel). Moreover, hRTP801 N-C1 fragment lacking the last 72 a.a was markedly impaired in its ability to associate with the full-length hRTP801. hRTP801 N-C2 fragment lacking only the last 37 a.a was almost as efficient as the full-length protein in self association (lane 4, right panel). Thus, a.a 161-195 of hRTP801 are important for self association.

Figure 22:
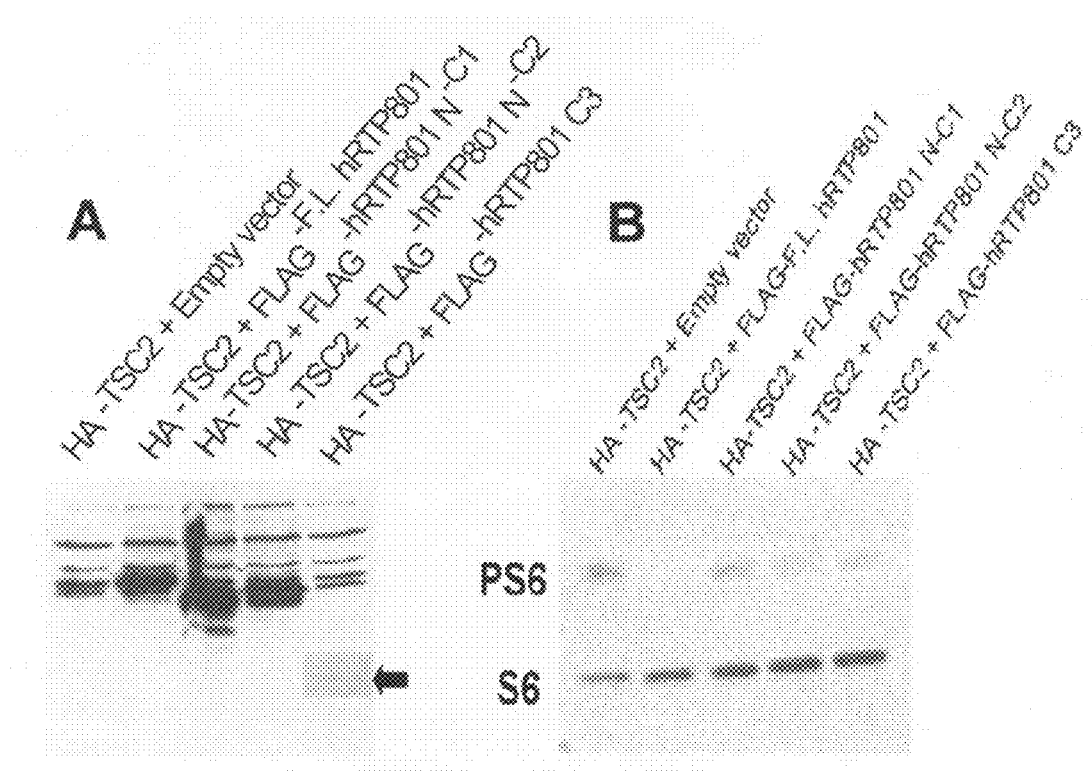
FIG. 22 shows results obtained using various RTP801 fragments.

B) A Deletion Mutant of hRTP801 that is Defective in Self Association is Functionally Impaired The Experiment was performed essentially as described in A) above, except cells were transfected with HA-TSC2 cDNA in addition to the hRTP801 constructs. Cell extracts were analyzed by anti-FLAG for expression of the FLAG-hRTP801 proteins (panel A) and by anti-phospho-S6 (pS6) which serves as a commonly used marker for mTOR activity (Averous J & Proud C G, *Oncogene* (2006) 25, 6423-6435). As a normalizer, total S6 antibody was used. As shown in FIG. 22 panel B, pS6 was absent in cells expressing full-length hRTP801 whereas cells expressing the hRTP801 N-C1 mutant (which is impaired in its ability to self associate), displayed similar amount of pS6 as control cells. In contrast, cells expressing hRTP801 N-C2 mutant (which was almost as efficient as full-length in self association) had lower level of pS6 than control. Interestingly, hRTP801 C3 fragment (a.a 161-232) was as efficient as hRTP801 N-C2 fragment (a.a 1-195) in inhibition of pS6 despite its very low expression (see in panel A). Thus, a.a 161-195 of hRTP801 are important for function of hRTP801 and its inhibition of mTOR activity.

C) HTRF Measurement of hRTP801 Self Association

Self association of hRTP801 by was tested with HTRF technology (Jia Y, et al., "Homogeneous time-resolved fluorescence and its applications for kinase assays in drug discovery" *Anal Biochem.* 2006 Sep. 15; 356(2):273-81. Epub 2006 May 24; Gabourdes et al., "A homogeneous time-resolved fluorescence detection of telomerase activity" *Anal Biochem.* 2004 Oct. 1; 333(1):105-13). Eu-labeled anti-HA and XL665-labeled anti-FLAG antibodies (CisBio) were added at a 1:100 dilution to 6 ug cytosolic extract of 293T HEK cells that were transfected with either empty plasmid (control) or co-transfected with two plasmids each containing cDNAs of either FLAG-full length hRTP801 or HA-SV5-hRTP801. Following overnight incubation at 40 C. the samples were excited at 330 nm and emission was read at 615 nm (Eu) and at 665 nm (FRET by XL665). The units shown in FIG. 23 refer to ratio of readings at 665 nm/615 nm*$10^4$ factor. Two batches of extracts expressing hRTP801 with both tags were tested.

Figure 23:
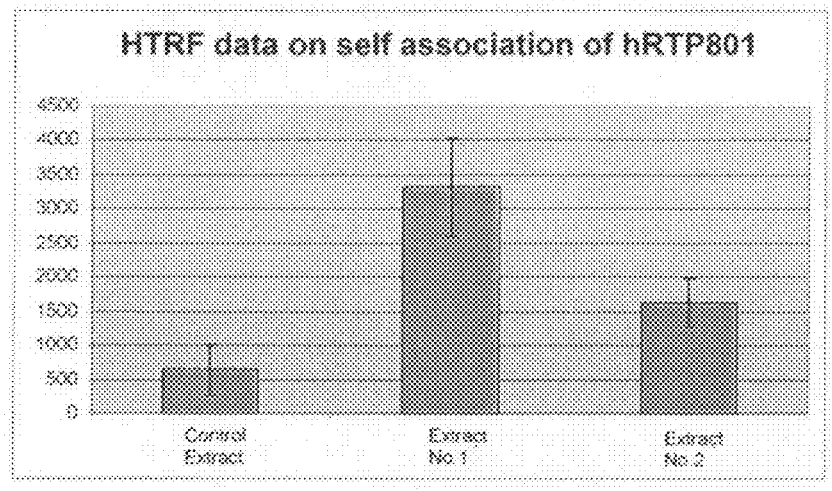
FIG. 23 depicts HTRF results relating to self association of hRTP801.

As shown in FIG. 23, FRET between Eu-anti HA and XL665-anti-FLAG were measured in extracts of cells that were transfected with the HA-hRTP801 and FLAG-hRTP801 cDNAs but not in control cells. Thus, self association of hRTP801 can be measured in an HTRF-based assay.

Example 6

Additional Experimental Results

Without being bound by theory, the inventors of the present invention have discovered the following:

1. RTP801 forms a physical complex with TSC2; interaction between RTP801 and TSC2 occurs via the C-terminal domain of RTP801 and N-terminal half of TSC2. For the purpose of a screening assay, recombinant bacterially expressed RTP801 can bind TSC2 expressed in cells.
2. RTP801 forms a physical complex with tyrosinated alpha-tubulin (Tyr-tubulin), and both N- and C-terminal fragments of RTP801 can bind Tyr-tubulin. Recombinant RTP801 or its C-terminal fragment can directly interact with purified tubulin.
3. Further, it was noted that RTP801-TSC2 and RTP801-tubulin complexes are separate entities and, moreover, mutually exclusive.
4. RTP801 can self associate.

The following is a non exclusive list of possible screening assays which can be conducted utilizing RTP801:
   a. ELISA-based assay utilizing immobilized GST-RTP801 baits and protein extracts from HA-TSC2 overexpressing cells—disruption of RTP80'-TSC2 interaction.
   b. ELISA-based assay utilizing immobilized purified tubulin as a bait and recombinant GST-RTP801-C—disruption of RTP80'-tubulin interaction.
   c. FRETWorks S.Tag based assay utilizing immobilized GST-RTP801 baits and extracts of cells overexpressing S-tagged TSC2—disruption of RTP801-TSC2 interaction.
   d. FRETWorks S.Tag based assay utilizing immobilized tubulin as a bait and recombinant S-tagged RTP801 or its portions—disruption of RTP801-tubulin interaction.

The above assays can also be used as secondary assays to test the function of small molecules identified, potentially, in a "Neogenesis-type" assay (identification of small molecules that directly bind to recombinant RTP801 protein).

Additional Assays which May be Employed Include:
1. Cell free assay utilizing recombinant minimal interacting fragments of RTP801 and TSC2—as described herein—disruption of RTP801-TSC2 interaction.
2. Cell-free assay utilizing differently tagged recombinant RTP801 proteins or fragments thereof—disruption of RTP801 self-association.

RTP801-TSC2 Interaction

Background

Without being bound by theory, RTP801 is involved in the mammalian target of rapamycin (mTOR) pathway. Specifically, RTP801, whose expression is induced under a variety of cell stresses, has been shown to be crucial for inhibition of activity of mTOR rapamycin-sensitive complex 1 under stress conditions such as hypoxia or energy deprivation (Brugarolas et al., Sofer et al). The exact molecular mechanism via which RTP801 inhibits mTOR activity remains obscure. However, it has been shown that RTP801 acts upstream to mTOR and exerts its inhibitory activity in a strict dependence on tuberin (TSC2) (Brugarolas et al. Sofer et al). TSC2 serves as a GTPase activating protein (GAP) for Rheb, a membrane-bound GTPase which, when in an active GTP-hound state, can activate the mTOR kinase (Zhang et al, Tee et al). As a consequence, activation of TSC2 leads to mTOR inhibition. TSC2 regulates Rheb function in cell membranes where Rheb resides. Lacking its own membrane targeting motifs, TSC2 is held in the membranes via interaction with hamartin (TSC1). Phosphorylation of TSC2 by AKT leads to its dissociation from TSC1, translocation to the cytosol and subsequent degradation (Cai et al).

Since. RTP801 and TSC2 are functionally linked and both act to inhibit mTOR activity, it is possible to inhibit RTP801 by decoupling it from TSC2.

Results Relating to The RTP801 and TSC2 Interaction hRTP801 region that binds TSC2 (FIG. 24). Various cDNA fragments of hRTP801 (FIG. 24A) were subcloned into a pGEX6P plasmid, to produce GST-FLAG fusion proteins which were purified on glutathione resin (FIG. 24B). The purified GST-FLAG fusion proteins ("baits") were immobilized to glutathione resin and incubated with post-nuclear supernatant of 293T cells transfected with either HA-tagged TSC2 (HA-TSC2) or with empty plasmid. Following elution, column-bound HA-TSC2 was then detected by immunoblotting with anti-HA antibodies. As shown in FIG. 24, both GST-full length hRTP801 and GST-hRTP801 "C" fragment bound HA-TSC2 present in the cell extract (lanes 2 and 3, respectively), while free GST (lane 1) failed to do so. Notably, GST-hRTP801 "C3" bait encompassing the last 70 a.a of hRTP801 was able to bind HA-TSC2 albeit with lower efficiency (lane 7). In contrast, GST-hRTP801 "N" and GST-hRTP801"C1" and GST-hRTP801 "C2" baits, failed to bind HA-TSC2 (lanes 4, 5, 6, respectively). Thus, the last 70 amino acids of hRTP801 comprising the C3 fragment are sufficient to bind TSC2. Note that C-terminal domain of RTP801 is the most conserved portion among all RTP801 orthologues.

Figure 25:
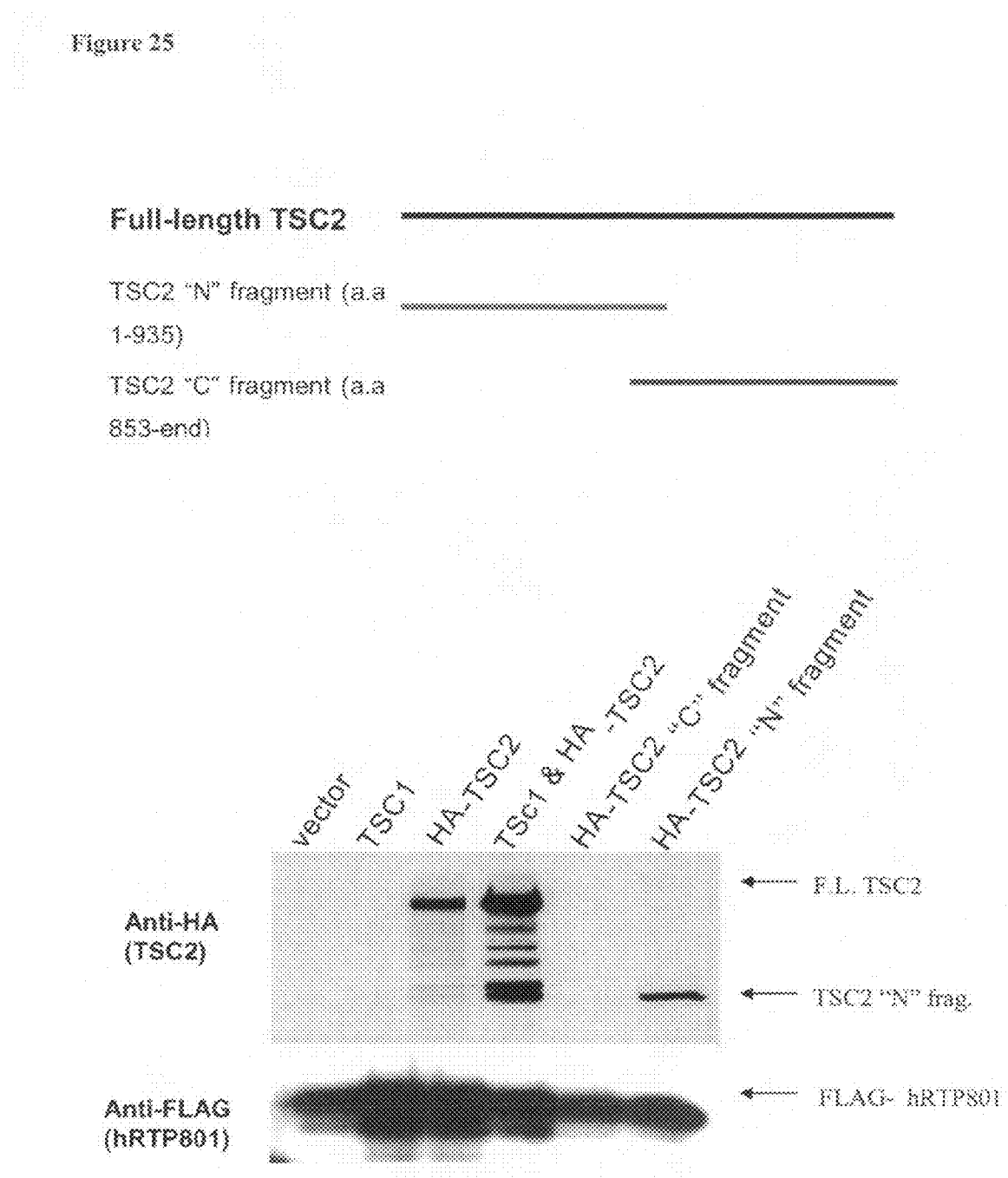
FIG. 25 shows the TSC2 region that binds hRTP801.

TSC2 region that binds hRTP801 (FIG. 25). Human TSC2 HA-tagged "N" and "C" fragments (FIG. 25, upper panel) as well as full length HA-tagged TSC2 were transfected into 293T cells along with FLAG-hRTP801 or with empty vector. Forty-eight hours after transfection, the cells were treated with $CoCl_2$ for overnight. Cells were harvested and post-nuclear supernatant was prepared and used for IP with anti-FLAG antibodies. As shown in FIG. 4, FLAG-hRTP801 was co-IP with both full length HA-TSC2 and HA-"N" fragment of TSC2 (lower panel). Unfortunately, the HA-"C" fragment of TSC2 was poorly expressed (undetectable in input extracts following immunoblotting with anti-HA antibodies) and hence could not be tested for co-IP with hRTP801. Nevertheless, these results show that aa 1-935 of human TSC2 are sufficient to bind to hRTP801.

Figure 26:
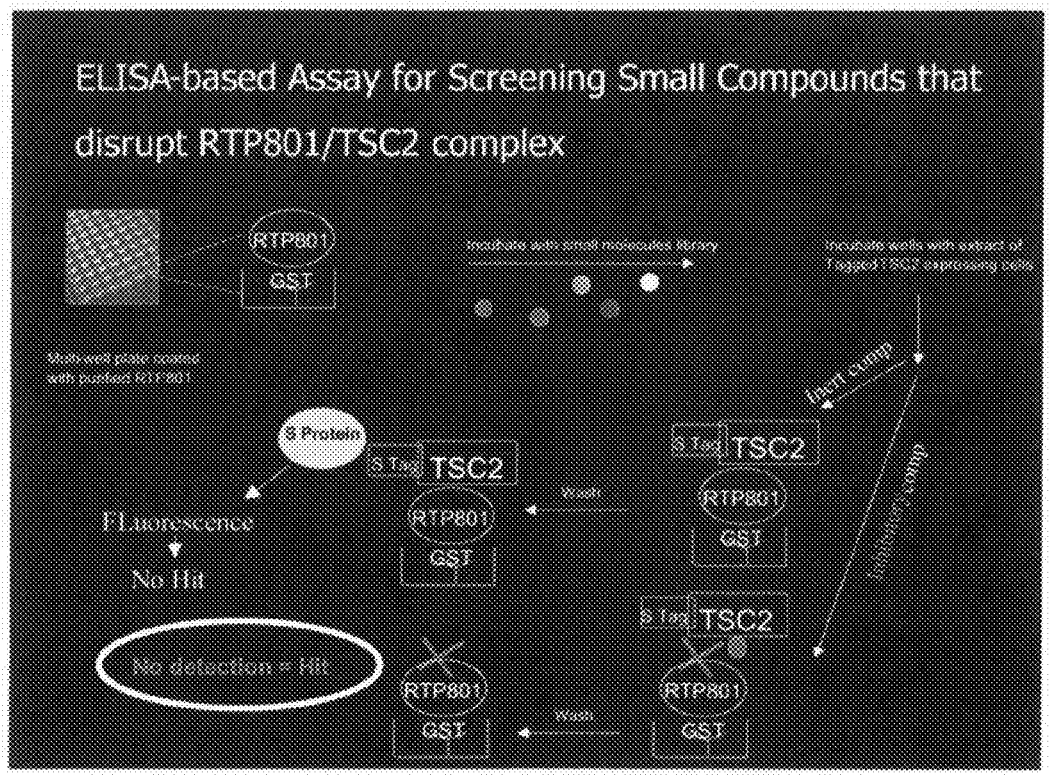
FIG. 26 depicts an additional exemplary assay.

FIGS. 18 and 19 show schematic details of some of the bioassays proposed herein; an additional possible proposed assay is shown in FIG. 26. This exemplary assay is based on the FRETWorks S Tag assay kit sold by Novagen. Briefly, a protein of interest (in our case TSC2) is fused to a 15 aa-long peptide (S Tag). This peptide binds with nM affinity to a 104 aa enzymatically inactive fragment of Rnase S(S protein). Upon binding, it reconstitutes a functional RNase S enzyme. The reconstituted enzymatic activity can then be assayed using a ribo-oligo substrate having a fluorophore group on one of its ends and a quencher group—on the other. Upon cleavage by the reconstituted RNase S, a fluorescence signal is obtained. Thus, as a modification of the first generation assay, S Tagged-TSC2-containing extract is allowed to bind GST-FLAG-hRTP801 bait bound to the plate. Bound S-tagged-TSC2 is assayed by a simple addition of the S protein and oligo-substrate followed by fluorescence measurement. This saves the need for the last 2 steps included in the first assay. Sensitivity of the assay may also be increased.

Note that screening assays employing any of the interactions disclosed herein can be performed along the lines of those exemplified in FIGS. 18, 19 and 26.

Positive control for proposed bioassays. A panel of monoclonal antibodies against different parts of hRTP801 has been generated by the inventors of the present invention. When added to GST-RTP801 pull-down reaction carried out in a tube format, some of these antibodies abolish TSC2-RTP801 binding, which is observed otherwise. Currently, we are testing whether these antibodies can also disrupt RTP801-TSC2 interaction in a 96-well ELISA format. Moreover, a more precise mapping of RTP801 epitopes reacting with the antibodies neutralizing RTP801-TSC2 binding may help to a more precise mapping of interacting interface of both proteins. However, an allosteric interference with the protein interaction cannot be excluded.

RTP801-Tyr-Alpha-Tubulin Interaction

Background

Figure 33:
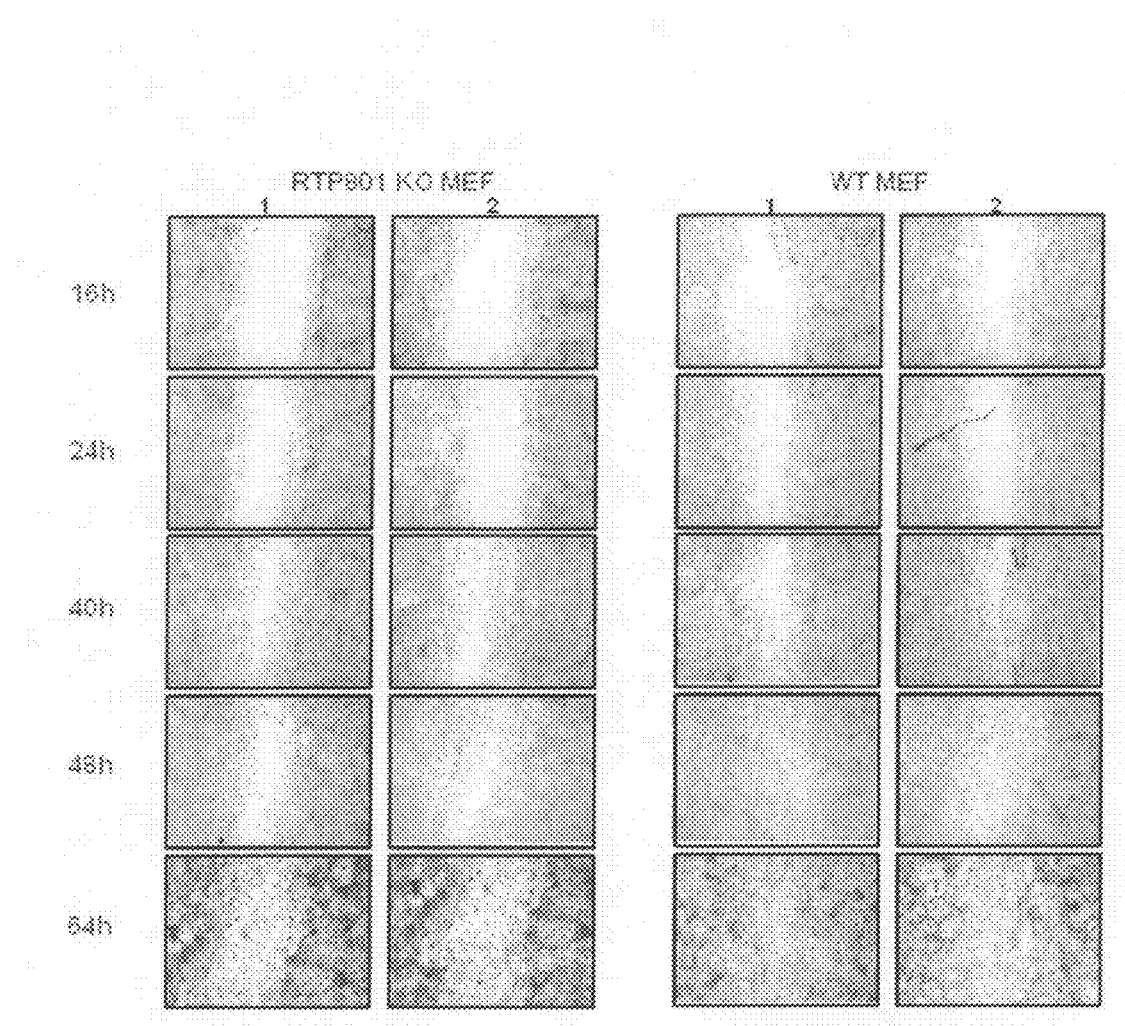
FIG. 33 shows reduced motility of RTP801 KO mouse embryo fibroblasts.

Alpha-Tubulin was identified by the inventors of the present invention as a protein that co-immunoprecipitated with FLAG-RTP801 from the overexpressing cells. No functional linkage between RTP801 and cytoskeleton has been previously suggested in the literature. However, several lines of evidence suggest a functional connection between mTOR and TSC1/TSC2 complex with this subcellular compartment, involving both actin cytoskeleton and microtubules. Inhibition of mTOR complex 1 by rapamycin significantly affects microtubules assembly, elongation and stability (Choi et al). TSC1- and TSC2-null cells have disorganized microtubules and are defective microtubule-dependent protein transport (Jiang and Yeung). TSC1- and TSC2-null cells have altered distribution of actin Filaments, which is reversed by either rapamycin or by Rheb inhibitors (Gau et al.). mTOR-rictor-bound complex, which is rapamycin-resistant, regulate the actin cytoskeleton (Sarbassov et al). There is also a compelling evidence that TSC1/TSC2 complex has an independent from mTOR activity impact on cytoskeleton through regulation of Rac 1 and Rho small GTPases. Thus, inactivation of TSC2 complex leads to reduced Rho-GTPase activity, decreased actin stress fibers and focal adhesions, and reduced motility and invasion (Liu et al). Interestingly, our proprietary data demonstrates also a reduced motility of RTP801 KO mouse embryo fibroblasts (MEF) (FIG. 33) in a standard cell monolayer scratching assay. This is in line with the fact that RTP801 acts as an activator of TSC1/TSC2 complex under stress conditions. Reduced motility of cells with inhibited RTP801 may be relevant to quite a number of therapeutic outcomes associated with RTP801 inhibition: e.g., reduced tumor growth and metastasis, reduced infiltration of inflammatory cells in the tissues, reduced pathological neoangiogenesis.

RTP801 interacts specifically with tyrosinated alpha-tubulin (see below). Tubulin undergoes tyrosination at its carboxyl terminus. This tyrosination is reversible leading to two distinct populations of microtubules: one, composed of tyrosinated tubulin (Tyr-tubulin), is dynamic and prone to depolymerization and another one, composed of detyrosinated or Glu-tubulin, is more stable (Bulinski et al). There are several proteins known to bind preferentially to Tyr-tubulin (Peris et al). Interestingly, one of these proteins, CLIP-170, was also shown to bind mTOR (Choi et al.). Moreover, the inventors of the present invention have discovered that CLIP-170 associated protein (CLASP2) is elevated ~3 folds in retinas of diabetic WT mice as compared with diabetic RTP801 KO mice whereas in non-diabetic mice its expression is unchanged in RTP801 KO mice compared to WT animals. Potential direct influence of RTP801 on microtubule dynamics may be of therapeutic importance influencing cell proliferation, motility and endothelial layers permeability (Birukova et al).

Results Relating to The RTP801 and Alpha-Tubulin Interaction

Figure 27:
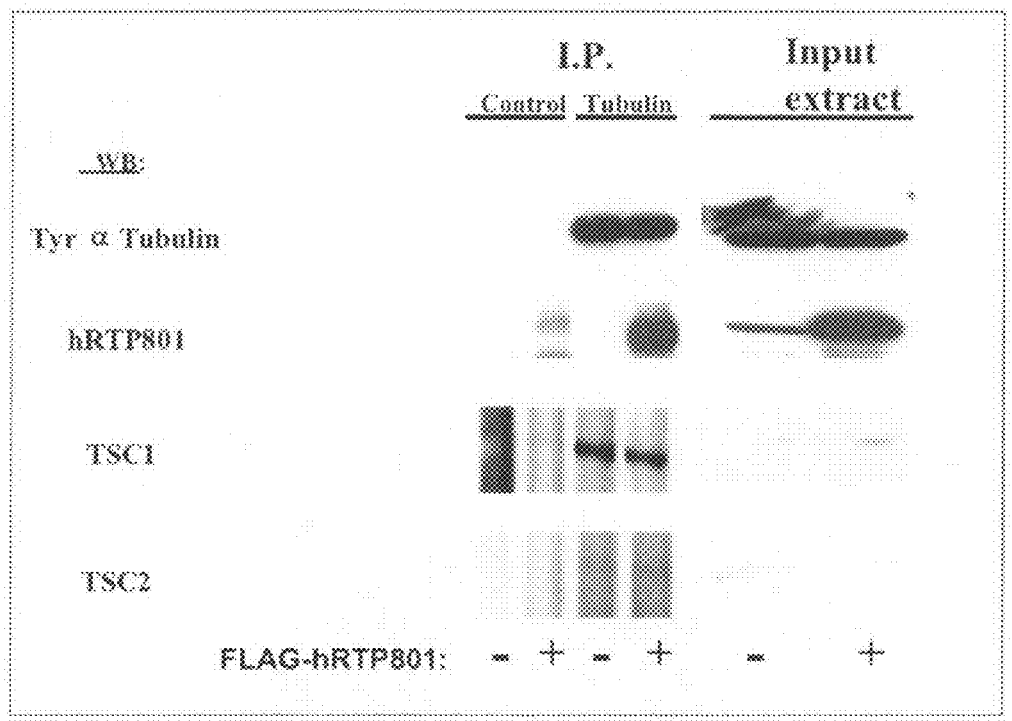
FIG. 27 shows reciprocal co-immunoprecipitation of exogenous RTP801 with endogenous Tyr-tubulin.
Figure 28:
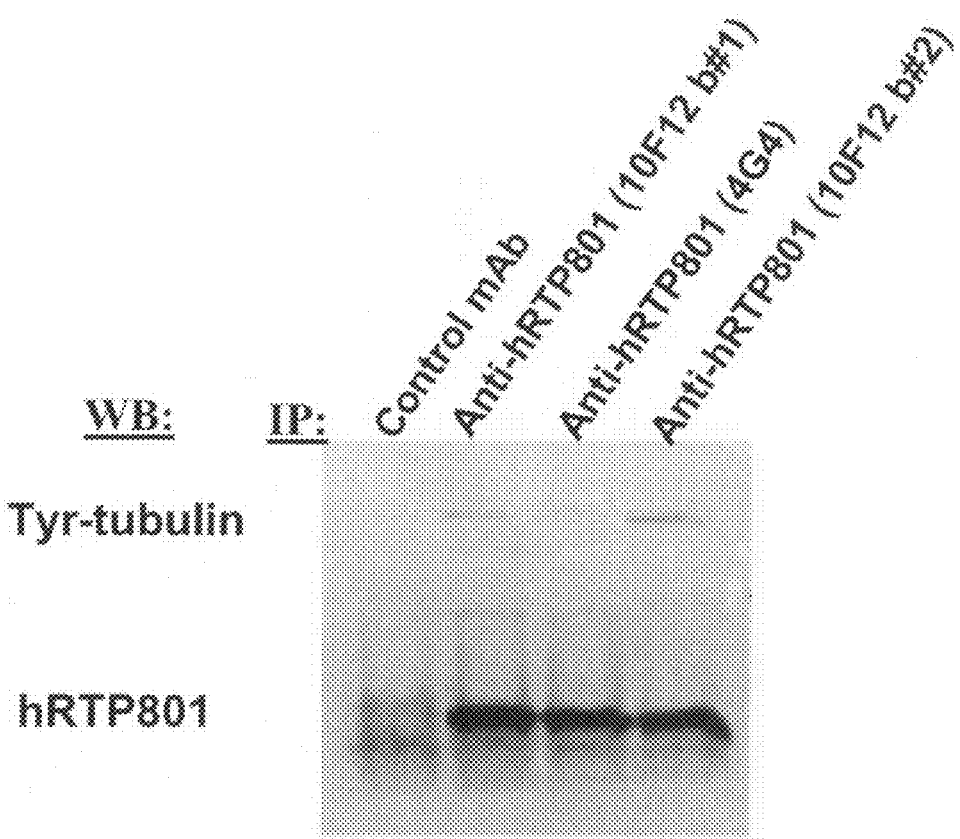
FIG. 28 shows co-immunoprecipitation of endogenous Tyr-tubulin with endogenous RTP801.

A. Evidence of a hRTP801 and Tyr-Tubulin Complex
 i. Co-IP of endogenous Tyr-tubulin with exogenous FLAG-tagged hRTP801 (FIG. 12). As shown in FIG. 12, Tyr-tubulin was specifically co-immunoprecipitated with FLAG-hRTP801.
 ii. Reciprocal co-IP of exogenous FLAG-hRTP801 with endogenous Tyr-tubulin (FIG. 27). The experiment was done essentially as described for FIG. 12 except that IP was performed using anti-Tyr-tubulin antibodies. As evident, hRTP801 was specifically and efficiently co-immunoprecipitated along with Tyr-tubulin where as no co-immunoprecipitation of RTP801 was observed with control antibodies.
 iii. Co-IP of endogenous Tyr-tubulin with endogenous hRTP801 (FIG. 28). Undifferentiated neuroblastoma cells (BE2C) were treated for 20 hrs with 150 uM $CoCl_2$ to stress the cells and to induce the expression of endogenous hRTP801. Post-nuclear supernatant was prepared and used for IP with either monoclonal antibodies (mAbs) against hRTP801 (two batches of mAb 10F12 and mAb 4G4) or with control monoclonal antibody. As evident, endogenous hRTP801 was specifically IP by both 10F12 and 4G4. Tyr-tubulin was co-IP with hRTP801 only when 10F12 mAb was used potentially indicating that mAb 4G4 interferes with RTP801-tubulin interactions. No co-IP of Tyr-tubulin was observed with control mAb.

B. Defining the Minimal Tubulin-Binding Regions in hRTP801
 Pull-down of Tyr-tubulin from cell extract (FIG. 16). Various regions (N-erminus, C-terminus, full-length—for construct details, see FIGS. 13 and 24) of hRTP801 were cloned in pGEX6P plasmids and expressed as GST-FLAG fusion proteins in bacteria followed by purification on glutathione resin (upper panel). The purified GST-FLAG fusion proteins ("baits") were immobilized on glutathione resin and incubated with post-nuclear supernatants of various transfectants of 293T cells (transfection details are irrelevant to this particular description). Following elution, RTP801-bound Tyr-tubulin was then detected by immunoblotting with anti-Tyr-tubulin antibodies. As evident, all RTP801 baits used were capable of Tyr-tubulin binding. Thus, Tyr-tubulin may bind hRTP801 at least in different two locations.

Figure 29:
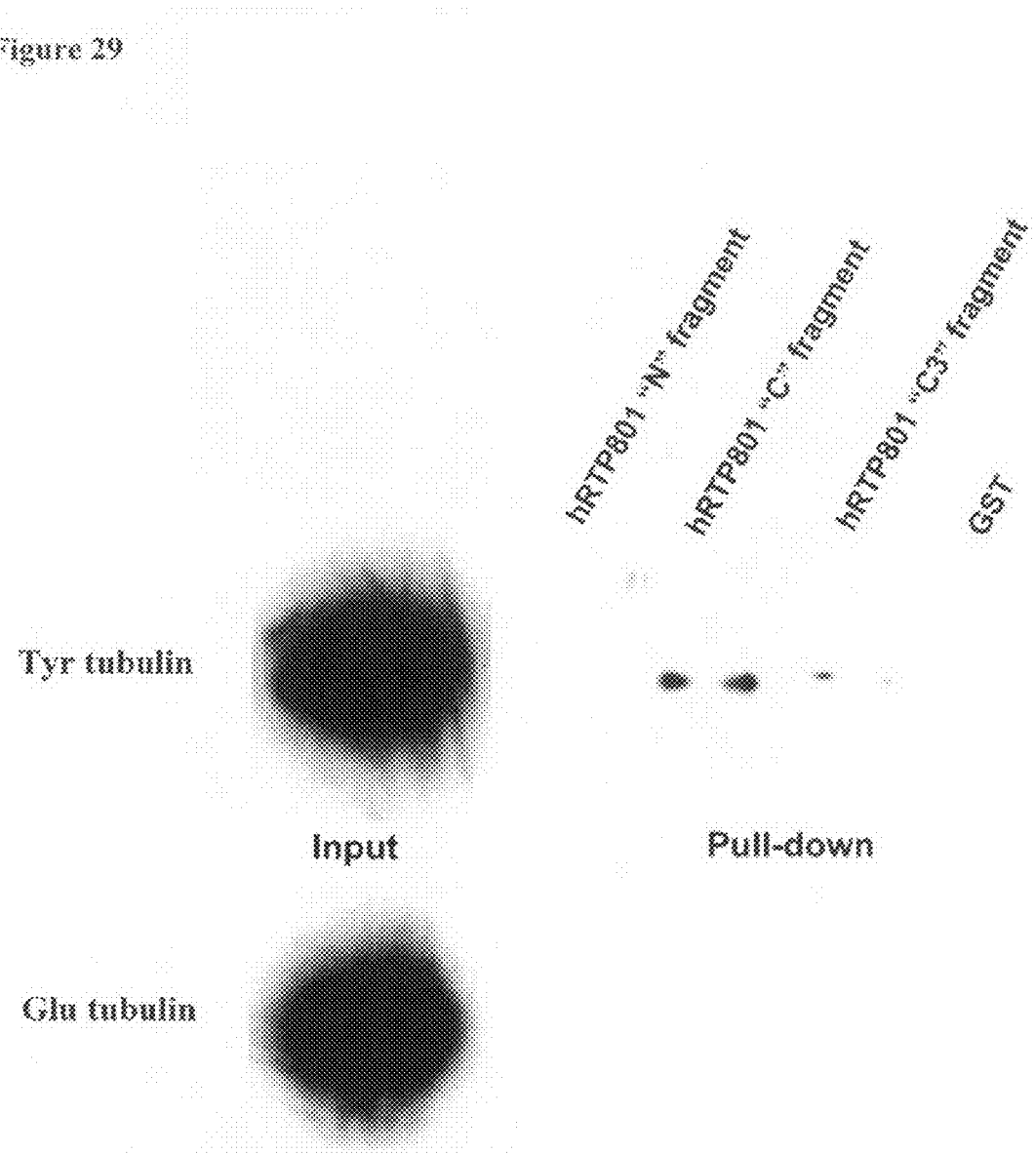
FIG. 29 depicts results indicating that RTP801 has preference for Tyr-tubulin as compared with de-tyrosinated tubulin (Glu-tubulin)

C. Evidence of Direct Binding Between hRTP801 and Tyr-Tubulin
 Direct binding of hRTP801 to Tyr-tubulin was assessed using ultra-pure brain tubulin (Cytoskeleton Inc., cat# TL238). Pull-down experiments using various GST-fused RTP801 baits were done essentially as described above except the fact that the beads with immobilized GST-RTP801 baits were incubated with purified tubulin under stringent conditions. Binding of Tyr-tubulin was assessed using specific anti-Tyr-tubulin antibodies. As shown herein, purified Tyr-tubulin hound to GST-FLAG-hRTP801 as well as to the hRTP801 "C" and "N" fragments but not to free GST. Thus, hRTP801 binds Tyr-tubulin directly. Results (FIG. 29) suggest that hRTP801 has preference for Tyr-tubulin as compared with detyrosinated tubulin (Glu-tubulin). This was determined by probing the hRTP80'-bound purified tubulin with either Tyr-tubulin or Glu-tubulin antibodies.

Development of an In Vitro Bioassay for hRTP801-Tyr-Tubulin Interaction
 Of the many possible screening assays discussed herein, the two following assays were tested:
 a. GST-hRTP801 was immobilized on an ELISA plate, incubated with purified tubulin and, following washes, bound Tyr-tubulin was detected using anti-Tyr-tubulin antibodies.
 b. Purified tubulin was immobilized on an ELISA plate, incubated with purified GST-hRTP801 baits or with free GST. Following washes, bound GST-hRTP801 was detected using anti-GST antibodies.

Figure 30:
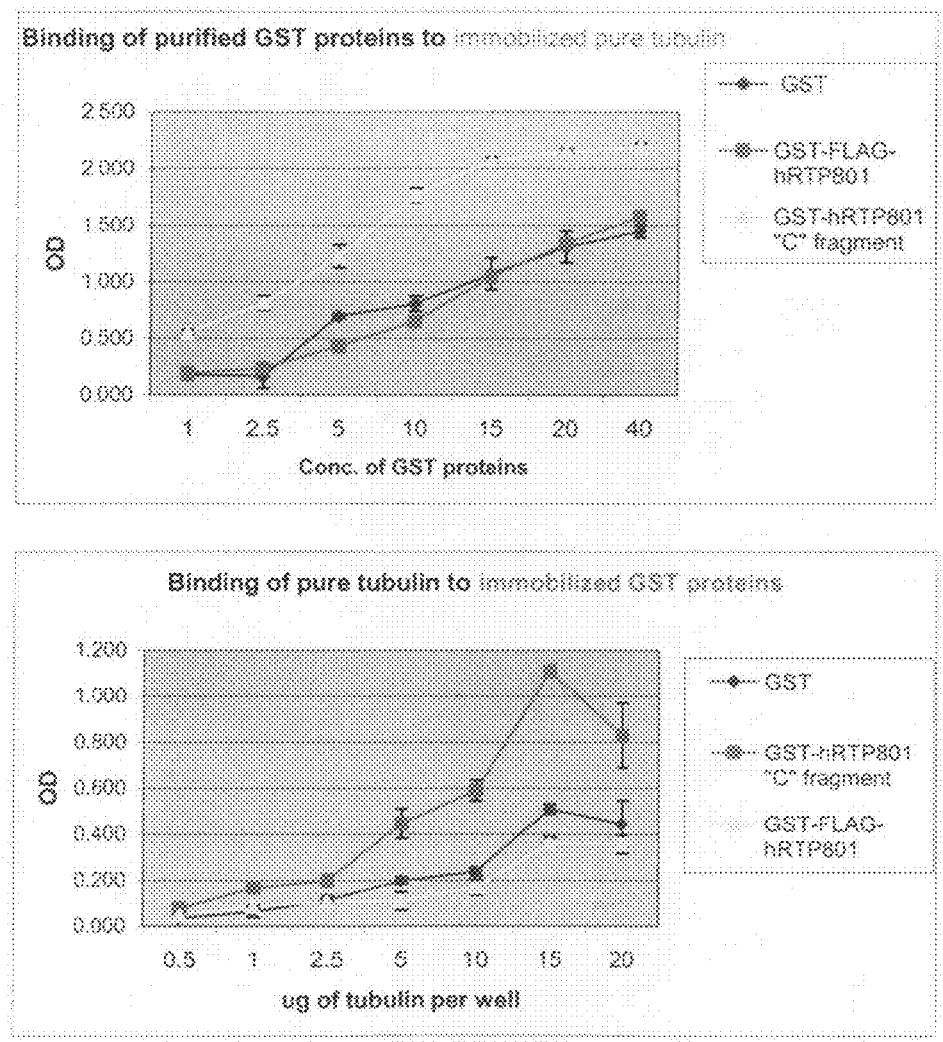
FIG. 30 presents the results of co-immunoprecipitation in a 96-well format.

Preliminary results (FIG. 30). In the 96-well format experiment, the GST-FLAG-hRTP801 bait did not bind tubulin above control levels (free GST). In contrast, GST-hRTP801 "C" fragment displayed saturating binding curves in both assay types.

An alternative assay may involve usage FRETWorks S Tag assay kit according to the principles described for RTP801-TSC2 interaction set-up. However, in the case of tubulin-RTP801 interaction, the plates will be coated with purified tubulin and binding of S-tagged RTP801 will be assessed by monitoring RNase S activity.

TSC2-Tyr-Alpha Tubulin Interactions
Background
 As discussed above, TSC2 null cells are defective in their cytoskeleton organization and microtubule-dependent transport (Jiang and Yeung). The inventors of the present invention were the first to discover physical association between the TSC1/TSC2 complex and tubulin.

Figure 31:
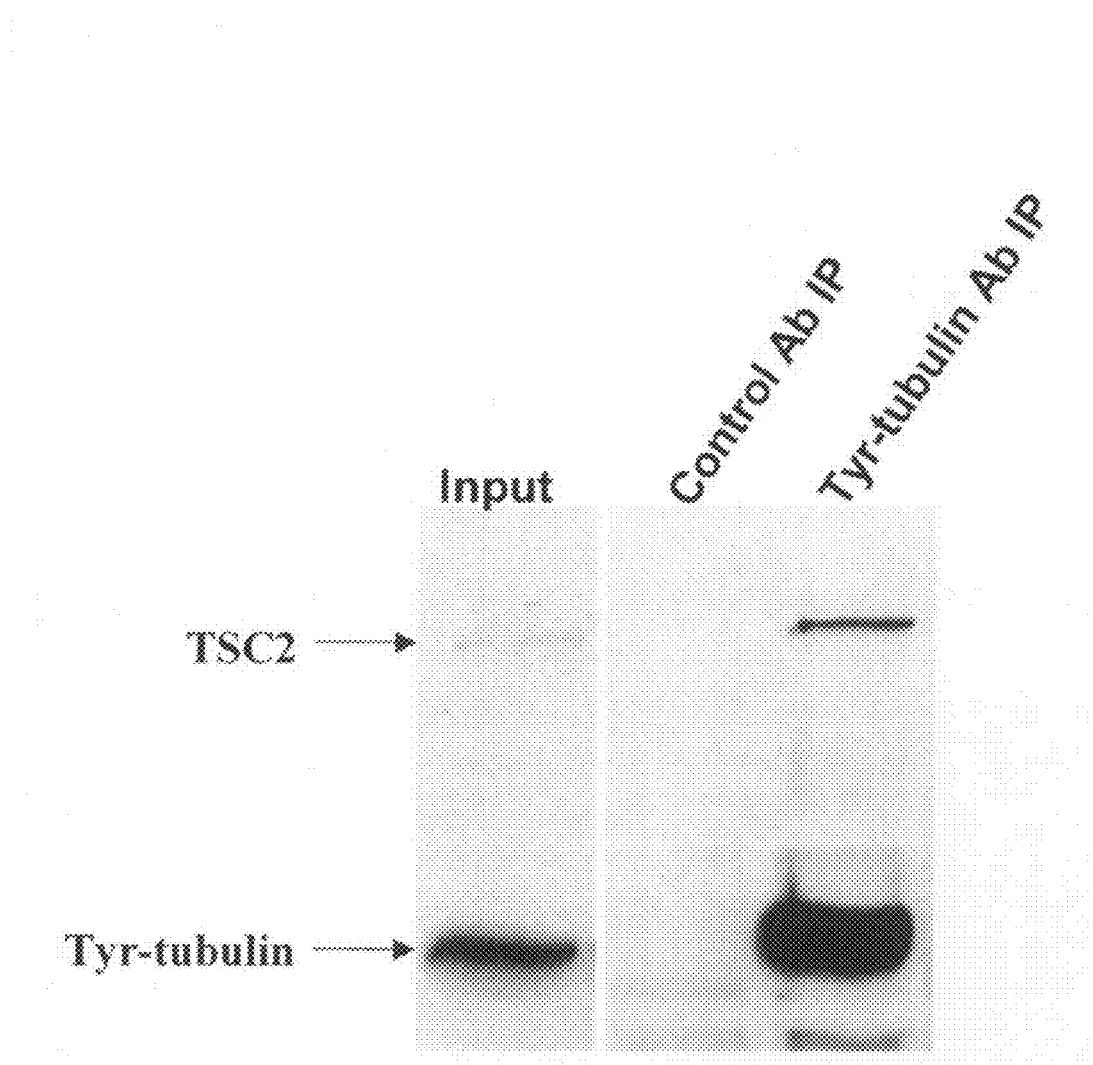
FIG. 31 shows that endogenous TSC2 co-immunoprecipitated with endogenous Tyr-alpha-tubulin.

Results
 Endogenous TSC2 co-immunoprecipitated with endogenous Tyr-alpha-tubulin (FIG. 31). Briefly, 293T cells were treated with $CoCl_2$ as described above; post nuclear supernatant was prepared and used for IP with either control antibodies or anti-Tyr-tubulin antibodies. Co-immunoprecipitated proteins were identified using either anti-Tyr tubulin or anti-TSC2 antibodies. As evident. TSC2 was specifically co-immunoprecipitated with Tyr-alpha tubulin. Thus, the inventors of the present invention have demonstrated association of TSC2 with tubulin.

Figure 32:
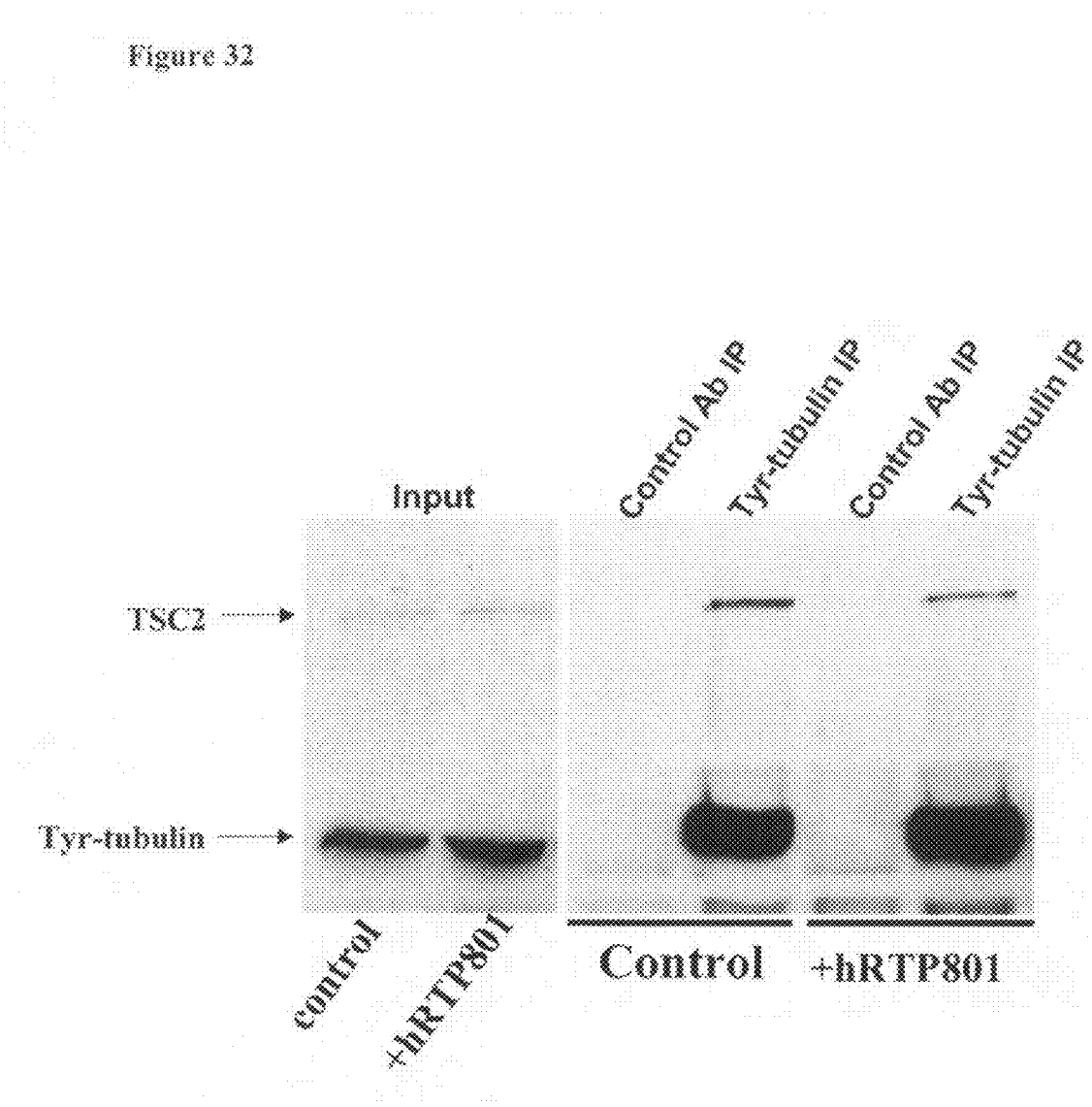
FIG. 32 demonstrates that co-immunoprecipitation of endogenous TSC2 with tubulin was significantly reduced in the presence of overexpressed exogenous RTP801.

Interplay Between hRTP801, TSC2 and Tyr-tubulin Complexes
 As Tyr-tubulin, TSC2 and RTP801 may interact with each other in a pair-wise manner, the inventors of the present invention examined whether hRTP801, TSC2 and Tyr-tubulin can affect the binding of each pair to the third binding partner. As shown in FIG. 32, co-IP of endogenous TSC2 with tubulin (conditions of experiment are as described for FIG. 31 except that exogenous hRTP801 was over-expressed for 48 hrs. prior to IP in part of cells) was significantly reduced in the presence of overexpressed exogenous hRTP801. As both tubulin and hRTP801 were probably in high excess over TSC2, it is likely that hRTP801 and tubulin competed for the binding on TSC2. Likewise, FIG. 16 shows reduced tubulin binding to GST-hRTP801 when TSC2 is bound (in HA-TSC2 overexpressing cells). Therefore, without being bound by theory there are separate mutually exclusive complexes of hRTP801-Tyr-tubulin, hRTP801-TSC2 and TSC2-Tyr-tubulin.

RTP801 Self Association
 Data obtained by the inventors of the present invention from bacterial two-hybrid system, suggests that hRTP801 forms homodimers (see example 5). A screening assay may also be based upon inhibition of RTP801 function by abolishing homodimerization.

REFERENCES

Brugarolas J, Lei K, Hurley R L, Manning B D, Reiling J H, Hafen E, Witters L A, Ellisen L W, Kaelin W G Jr. Regulation of mTOR function in response to hypoxia by REDD1 and the TSC1/TSC2 tumor suppressor complex. Genes Dev. 2004 Dec. 1; 18(23):2893-904

Ellisen L W. Growth control under stress: mTOR regulation through the REDD1-TSC pathway. Cell Cycle. 2005 November; 4(11):1500-02

Sofer A, Lei K, Johannessen C M, Ellisen L W. Regulation of mTOR and cell growth in response to energy stress by REDD1. Mol Cell Biol. 2005 July; 25(14):5834-45.

Zhang Y, Gao X, Saucedo L J, Ru B. Edgar B A, Pan D. Rheb is a direct target of the tuberous sclerosis tumor suppressor proteins. Nat Cell Biol. 2003 June; 5(6):578-81.

Tee A R, Manning B D, Roux P P, Cantley L C, Blenis J. Tuberous sclerosis complex gene products, Tuberin and Hamartin, control mTOR signaling by acting as a GTPase-activating protein complex toward Rheb. Curr Biol. 2003 Aug. 5; 13(15):1259-68.

Cai S L, Tee A R, Short J D, Bergeron J M, Kim J, Shen J, Guo R, Johnson C L, Kiguchi K, Walker C L. Activity of TSC2 is inhibited by AKT-mediated phosphorylation and membrane partitioning. J. Cell Biol. 2006 Apr. 24; 173(2):279-89.

Li Y, Inoki K, Vikis H, Guan K L. Measurements of TSC2 GAP Activity Toward Rheb. Methods Enzymol. 2005; 407: 46-54.

Choi J H, Adames N R, Chan T F, Zeng C, Cooper J A, Zheng X F. TOR signaling regulates microtubule structure and function. Curr Biol. 2000 Jul. 13; 10(14):861-4.

Jiang X, Yeung R S. Regulation of microtubule-dependent protein transport by the TSC2/mammalian target of rapamycin pathway. Cancer Res. 2006 May 15; 66(10):5258-69.

Gau C L, Kato-Stankiewicz J, Jiang C, Miyamoto S, Guo L, Tamanoi F. Farnesyltransferase inhibitors reverse altered growth and distribution of actin filaments in Tsc-deficient cells via inhibition of both rapamycin-sensitive and -insensitive pathways. Mol Cancer Ther. 2005 June; 4(6):918-26.

Sarbassov D D, Ali S M, Sengupta S, Sheen J H, Hsu P P, Bagley A F, Markhard A L, Sabatini D M. Prolonged rapamycin treatment inhibits mTORC2 assembly and Akt/PKB. Mol. Cell. 2006 Apr. 21; 22(2):159-68.

Bulinski J C, Gundersen G G. Stabilization of post-translational modification of microtubules during cellular morphogenesis. Bioessays. 1991 June; 13(6):285-93. Review.

Peris L, Thery M. Faure J, Saoudi Y, Lafanechere L, Chilton J K, Gordon-Weeks P, Galjart N, Bornens M, Wordeman L, Wehland J, Andrieux A, Job D. Tubulin tyrosination is a major factor affecting the recruitment of CAP-Gly proteins at microtubule plus ends. J. Cell Biol. 2006 Sep. 11; 174 (6):839-49.

Honore S. Pasquier E, Braguer D. Understanding microtubule dynamics for improved cancer therapy. Cell Mol Life Sci. 2005 December; 62(24)3039-56. Review.

Liu H, Derek C. Radisky D C, Nelson C M, Zhang H, Fata J E, Roth R A, Bissell M. Mechanism of Akt1 inhibition of breast cancer cell invasion reveals a protumorigenic role for TSC2. Proc Natl Acad Sci USA, 2006 Mar. 14; 103(11): 4134-9.

Birukova A A, Birukov K G, Smurova K, Adyshev D, Kaibuchi K, Alieva I, Garcia J G, Venin A D. Novel role of microtubules in thrombin-induced endothelial barrier dysfunction. FASEB J. 2004 December; 18(15):1879-90.

---

What is claimed is:

1. A process for determining whether a test compound modulates the binding of an RTP801 polypeptide to a second polypeptide comprising the following steps:
(a) separately contacting the RTP801 polypeptide (SEQ ID NO:2 or a fragment thereof) with the second polypeptide, which is selected from the group consisting of a TSC1 polypeptide (SEQ ID NO:4 or a fragment thereof), a TSC2 polypeptide (SEQ ID NO:6 or a fragment thereof) and an alpha-tubulin polypeptide (SEQ ID NO:8 or a fragment thereof), both in the presence and in the absence of the test compound; and
(b) determining the amount of complex formed between the RTP801 polypeptide or fragment thereof and the second polypeptide in the presence and in the absence of the test compound,
wherein a difference in the amounts determined indicates that the test compound modulates the binding of the RTP801 polypeptide to the second polypeptide.

2. The process of claim 1, wherein the RTP801 polypeptide or fragment thereof or the second polypeptide or both are substantially purified.

3. The process of claim 1, wherein the RTP801 polypeptide or fragment thereof comprises a tag.

4. The process of claim 1, wherein the second polypeptide comprises a second tag.

5. The process of claim 1, wherein the RTP801 polypeptide comprises a first tag and the second polypeptide comprises a second tag.

6. The process of claim 1, wherein one of the RTP801 polypeptide or fragment thereof or the second polypeptide is attached to a solid support.

7. The process of claim 1, wherein the RTP801 polypeptide or fragment thereof or the second polypeptide is expressed in a cell.

8. The process of claim 1, wherein the fragment of the RTP801 polypeptide consists of amino acids 1-88 of SEQ ID NO:2.

9. The process of claim 1, wherein the fragment of the RTP801 polypeptide consists of amino acids 89-232 of SEQ ID NO:2.

10. The process of claim 1, wherein the fragment of the RTP801 polypeptide consists of amino acids 1-161 of SEQ ID NO:2.

11. The process of claim 1, wherein the fragment of the RTP801 polypeptide consists of amino acids 1-195 of SEQ ID NO:2.

12. The process of claim 1, wherein the fragment of the RTP801 polypeptide consists of amino acids 161-232 of SEQ ID NO: b 2.

13. The process of claim 1, wherein the fragment of the RTP801 polypeptide consists of amino acids 161-195 of SEQ ID NO:2.

14. A process for determining whether a test compound modulates the binding of an RTP801 polypeptide to a second polypeptide comprising the following steps:
(a) separately contacting a cell which expresses the RTP801 polypeptide (SEQ ID NO:2 or a fragment thereof) with a second polypeptide, which is selected from the group consisting of TSC1 polypeptide (SEQ ID NO; 4 or a fragment thereof), a TSC2 polypeptide (SEQ ID NO:6 or a fragment thereof) and an alpha-tubulin polypeptide (SEQ ID NO:8 or a fragment thereof), both in the presence and in the absence of the test compound; and
(b) determining the amount of complex formed between the RTP801 polypeptide or fragment thereof and the second polypeptide in the presence and in the absence of the test compound,
wherein a difference in the amounts determined indicates that that the test compound modulates the binding of the RTP801 polypeptide to the second polypeptide.

15. The process of claim 14, wherein a lysate is prepared from the cell expressing the RTP801 polypeptide or fragment thereof after step (a) and the determination in step (b) is performed on the lysate.

16. The process of claim 14, wherein the RTP801 polypeptide or fragment thereof comprises a tag.

17. The process of claim 14, wherein the second polypeptide comprises a tag.

18. The process of claim 14, wherein the RTP801 polypeptide or fragment thereof comprises a first tag and the second polypeptide comprises a second tag.

* * * * *

SEQUENCE LISTING

```
<160> NUMBER OF SEQ ID NOS: 8

<210> SEQ ID NO 1
<211> LENGTH: 1782
<212> TYPE: DNA
<213> ORGANISM: Homo sapiens

<400> SEQUENCE: 1
tttggccctc gaggccaaga attcggcacg aggggggggag gtgcgagcgt ggacctggga      60
cgggtctggg cggctctcgg tggttggcac gggttcgcac acccattcaa gcggcaggac     120
gcacttgtct tagcagttct cgctgaccgc gctagctgcg gcttctacgc tccggcactc     180
tgagttcatc agcaaacgcc ctggcgtctg tcctcaccat gcctagcctt tgggaccgct     240
tctcgtcgtc gtccacctcc tcttcgccct cgtccttgcc ccgaactccc accccagatc     300
ggccgccgcg ctcagcctgg gggtcggcga cccggggagga ggggtttgac cgctccacga     360
gcctggagag ctcggactgc gagtccctgg acagcagcaa cagtggcttc gggccggagg     420
aagacacggc ttacctggat ggggtgtcgt tgcccgactt cgagctgctc agtgaccctg     480
aggatgaaca cttgtgtgcc aacctgatgc agctgctgca ggagagcctg gcccaggcgc     540
ggctgggctc tcgacgccct gcgcgcctgc tgatgcctag ccagttggta agccaggtgg     600
gcaaagaact actgcgcctg gcctacagcg agccgtgcgg cctgcggggg gcgctgctgg     660
acgtctgcgt ggagcagggc aagagctgcc acagcgtggg ccagctggca ctcgacccca     720
gcctggtgcc caccttccag ctgaccctcg tgctgcgcct ggactcacga ctctggccca     780
```

```
-continued agatccaggg gctgtttagc tccgccaact ctcccttcct ccctggcttc agccagtccc    840
tgacgctgag cactggcttc cgagtcatca agaagaagct gtacagctcg aacagctgc    900 tcattgagga gtgttgaact tcaacctgag ggggccgaca gtgccctcca agacagagac    960
gactgaactt tgggggtgga gactagaggc aggagctgag ggactgattc ctgtggttgg   1020
aaaactgagg cagccaccta aggtggaggt gggggaatag tgtttcccag gaagctcatt   1080
gagttgtgtg cgggtggctg tgcattgggg acacataccc ctcagtactg tagcatgaaa   1140
caaaggctta ggggccaaca aggcttccag ctggatgtgt gtgtagcatg taccttatta   1200
tttttgttac tgacagttaa cagtggtgtg acatccagag agcagctggg ctgctcccgc   1260
cccagcccgg cccagggtga aggaagaggc acgtgctcct cagagcagcc ggagggaggg   1320
gggaggtcgg aggtcgtgga ggtggtttgt gtatcttact ggtctgaagg gaccaagtgt   1380
gtttgttgtt tgttttgtat cttgtttttc tgatcggagc atcactactg acctgttgta   1440
ggcagctatc ttacagacgc atgaatgtaa gagtaggaag gggtgggtgt cagggatcac   1500
ttgggatctt tgacacttga aaaattacac ctggcagctg cgtttaagcc ttcccccatc   1560
gtgtactgca gagttgagct ggcagggag gggctgagag ggtgggggct ggaacccctc   1620
cccgggagga gtgccatctg ggtcttccat ctagaactgt ttacatgaag ataagatact   1680
cactgttcat gaatcacttt gatgttcaag tattaagacc tatgcaatat ttttacttt   1740 tctaataaac atgtttgtta aaacaaaaaa aaaaaaaaa aa                      1782

<210> SEQ ID NO 2
<211> LENGTH: 232
<212> TYPE: PRT
<213> ORGANISM: Homo sapiens

<400> SEQUENCE: 2

Met Pro Ser Leu Trp Asp Arg Phe Ser Ser Ser Thr Ser Ser
1               5                   10                  15

Pro Ser Ser Leu Pro Arg Thr Pro Thr Pro Asp Arg Pro Arg Ser
            20                  25                  30

Ala Trp Gly Ser Ala Thr Arg Glu Glu Gly Phe Asp Arg Ser Thr Ser
        35                  40                  45

Leu Glu Ser Ser Asp Cys Glu Ser Leu Asp Ser Asn Ser Gly Phe
    50                  55                  60

Gly Pro Glu Glu Asp Thr Ala Tyr Leu Asp Gly Val Ser Leu Pro Asp
65                  70                  75                  80

Phe Glu Leu Leu Ser Asp Pro Glu Asp Glu His Leu Cys Ala Asn Leu
                85                  90                  95

Met Gln Leu Leu Gln Glu Ser Leu Ala Gln Ala Arg Leu Gly Ser Arg
            100                 105                 110

Arg Pro Ala Arg Leu Leu Met Pro Ser Gln Leu Val Ser Gln Val Gly
        115                 120                 125

Lys Glu Leu Leu Arg Leu Ala Tyr Ser Glu Pro Cys Gly Leu Arg Gly
    130                 135                 140

Ala Leu Leu Asp Val Cys Val Glu Gln Gly Lys Ser Cys His Ser Val
145                 150                 155                 160

Gly Gln Leu Ala Leu Asp Pro Ser Leu Val Pro Thr Phe Gln Leu Thr
                165                 170                 175

Leu Val Leu Arg Leu Asp Ser Arg Leu Trp Pro Lys Ile Gln Gly Leu
            180                 185                 190

Phe Ser Ala Asn Ser Pro Phe Leu Pro Gly Phe Ser Gln Ser Leu
        195                 200                 205
```

Thr Leu Ser Thr Gly Phe Arg Val Ile Lys Lys Lys Leu Tyr Ser Ser
    210                 215                 220

Glu Gln Leu Leu Ile Glu Glu Cys
225                 230

<210> SEQ ID NO 3
<211> LENGTH: 3495
<212> TYPE: DNA
<213> ORGANISM: Homo sapiens

<400> SEQUENCE: 3

| | | | | | |
|---|---|---|---|---|---|
| atggcccaac | aagcaaatgt | cggggagctt | cttgccatgc | tggactcccc | catgctgggt | 60 |
| gtgcgggacg | acgtgacagc | tgtctttaaa | gagaacctca | attctgaccg | tggccctatg | 120 |
| cttgtaaaca | ccttggtgga | ttattacctg | gaaaccagct | ctcagccggc | attgcacatc | 180 |
| ctgaccacct | tgcaagagcc | acatgacaag | cacctcttgg | acaggattaa | cgaatatgtg | 240 |
| ggcaaagccg | ccactcgttt | atccatcctc | tcgttactgg | gtcatgtcat | aagactgcag | 300 |
| ccatcttgga | agcataagct | ctctcaagca | cctcttttgc | cttctttact | aaaatgtctc | 360 |
| aagatggaca | ctgacgtcgt | tgtcctcaca | acaggcgtct | tggtgttgat | aaccatgcta | 420 |
| ccaatgattc | cacagtctgg | gaaacagcat | cttcttgatt | tctttgacat | ttttggccgt | 480 |
| ctgtcatcat | ggtgcctgaa | gaaaccaggc | acgtggcgg | aagtctatct | cgtccatctc | 540 |
| catgccagtg | tgtacgcact | ctttcatcgc | ctttatggaa | tgtacccttg | caacttcgtc | 600 |
| tccttttgc | gttctcatta | cagtatgaaa | gaaaacctgg | agactttttga | agaagtggtc | 660 |
| aagccaatga | tggagcatgt | gcgaattcat | ccggaattag | tgactggatc | caaggaccat | 720 |
| gaactggacc | tcgaaggtg | gaagagatta | gaaactcatg | atgttgtgat | cgagtgtgcc | 780 |
| aaaatctctc | tggatcccac | agaagcctca | tatgaagatg | ctattctgt | gtctcaccaa | 840 |
| atctcagccc | gctttcctca | tcgttcagcc | gatgtcacca | ccagccctta | tgctgacaca | 900 |
| cagaatagct | atgggtgtgc | tacttctacc | ccttactcca | cgtctcggct | gatgttgtta | 960 |
| aatatgccag | gcagctacc | tcagactctg | agttccccat | cgacacggct | gataactgaa | 1020 |
| ccaccacaag | ctactctttg | gagcccatct | atggtttgtg | gtatgaccac | tcctccaact | 1080 |
| tctcctggaa | atgtcccacc | tgatctgtca | caccttaca | gtaaagtctt | tggtacaact | 1140 |
| gcaggtggaa | aaggaactcc | tctgggaacc | ccagcaacct | ctcctcctcc | agccccactc | 1200 |
| tgtcattcgg | atgactacgt | gcacatttca | ctcccccagg | ccacagtcac | accccccagg | 1260 |
| aaggaagaga | gaatggattc | tgcaagacca | tgtctacaca | gacaacacca | tcttctgaat | 1320 |
| gacagaggat | cagaagagcc | acctggcagc | aaaggttctg | tcactctaag | tgatcttcca | 1380 |
| gggtttttag | gtgatctggc | ctctgaagaa | gatagtattg | aaaaagataa | agaagaagct | 1440 |
| gcaatatcta | gagaactttc | tgagatcacc | acagcagagg | cagagcctgt | ggttcctcga | 1500 |
| ggaggctttg | actctcccctt | ttaccgagac | agtctcccag | ttctcagcg | gaagacccac | 1560 |
| tcggcagcct | ccagttctca | gggcgccagc | gtgaaccctg | agcctttaca | ctcctccctg | 1620 |
| gacaagcttg | ggcctgacac | accaaagcaa | gcctttactc | ccatagacct | gccctgcggc | 1680 |
| agtgctgatg | aaagccctgc | gggagacagg | gaatgccaga | cttctttgga | gaccagtatc | 1740 |
| ttcactccca | gtccttgtaa | aattccacct | ccgacgagag | tgggctttgg | aagcgggcag | 1800 |
| cctccccgt | atgatcatct | ttttgaggtg | gcattgccaa | agacagccca | tcattttgtc | 1860 |
| atcaggaaga | ctgaggagct | gttaaagaaa | gcaaaggaa | acacagagga | agatggtgtg | 1920 |
| ccctctacct | ccccaatgga | agtgctggac | agactgatac | agcagggagc | agacgcgcac | 1980 |

```
agcaaggagc tgaacaagtt gcctttaccc agcaagtctg tcgactggac ccactttgga    2040
ggctctcctc cttcagatga gatccgcacc ctccgagacc agttgctttt actgcacaac    2100
cagttactct atgagcgttt taagaggcag cagcatgccc tccggaacag gcggctcctc    2160
cgcaaggtga tcaaagcagc agctctggag gaacataatg ctgccatgaa agatcagttg    2220
aagttacaag agaaggacat ccagatgtgg aaggttagtc tgcagaaaga acaagctaga    2280
tacaatcagc tccaggagca gcgtgacact atggtaacca agctccacag ccagatcaga    2340
cagctgcagc atgaccgaga ggaattctac aaccagagcc aggaattaca gacgaagctg    2400
gaggactgca ggaacatgat tgcggagctg cggatagaac tgaagaaggc caacaacaag    2460
gtgtgtcaca ctgagctgct gctcagtcag gtttcccaaa agctctcaaa cagtgagtcg    2520
gtccagcagc agatggagtt cttgaacagg cagctgttgg ttcttgggga ggtcaacgag    2580
ctctatttgg aacaactgca gaacaagcac tcagatacca caaggaagt agaaatgatg    2640 aaagccgcct atcggaaaga gctagaaaaa acagaagcc atgttctcca gcagactcag    2700
aggcttgata cctcccaaaa acggattttg gaactggaat ctcacctggc caagaaagac    2760
caccttcttt tggaacagaa gaaatatcta gaggatgtca actccaggc aagaggacag    2820 ctgcaggccg cagagagcag gtatgaggct cagaaaagga taacccaggt gtttgaattg    2880
gagatcttag atttatatgg caggttggag aaagatggcc tcctgaaaaa acttgaagaa    2940
gaaaaagcag aagcagctga agcagcagaa gaaaggcttg actgttgtaa tgacgggtgc    3000
tcagattcca tggtagggca caatgaagag gcatctggcc acaacggtga gaccaagacc    3060
cccaggccca gcagcgcccg ggcagtagt ggaagcagag gtggtggagg cagcagcagc    3120
agcagcagcg agctttctac cccagagaaa cccccacacc agagggcagg cccattcagc    3180
agtcggtggg agacgactat gggagaagcg tctgccagca tccccaccac tgtgggctca    3240
cttcccagtt caaaaagctt cctgggtatg aaggctcgag agttatttcg taataagagc    3300
gagagccagt gtgatgagga cggcatgacc agtagccttt ctgagagcct aaagacagaa    3360
ctgggcaaag acttgggtgt ggaagccaag attcccctga acctagatgg ccctcacccg    3420 tctccccga ccccggacag tgttggacag ctacatatca tggactacaa tgagactcat    3480
catgaacaca gctaa                                                     3495
```

<210> SEQ ID NO 4
<211> LENGTH: 1164
<212> TYPE: PRT
<213> ORGANISM: Homo sapiens

<400> SEQUENCE: 4

```
Met Ala Gln Gln Ala Asn Val Gly Glu Leu Leu Ala Met Leu Asp Ser
1               5                   10                  15

Pro Met Leu Gly Val Arg Asp Asp Val Thr Ala Val Phe Lys Glu Asn
                20                  25                  30

Leu Asn Ser Asp Arg Gly Pro Met Leu Val Asn Thr Leu Val Asp Tyr
            35                  40                  45

Tyr Leu Glu Thr Ser Ser Gln Pro Ala Leu His Ile Leu Thr Thr Leu
        50                  55                  60

Gln Glu Pro His Asp Lys His Leu Leu Asp Arg Ile Asn Glu Tyr Val
65                  70                  75                  80

Gly Lys Ala Ala Thr Arg Leu Ser Ile Leu Ser Leu Leu Gly His Val
                85                  90                  95

Ile Arg Leu Gln Pro Ser Trp Lys His Lys Leu Ser Gln Ala Pro Leu
```

```
                  100             105                 110
Leu Pro Ser Leu Leu Lys Cys Leu Lys Met Asp Thr Asp Val Val Val
            115                 120                 125
Leu Thr Thr Gly Val Leu Val Leu Ile Thr Met Leu Pro Met Ile Pro
            130                 135                 140
Gln Ser Gly Lys Gln His Leu Leu Asp Phe Phe Asp Ile Phe Gly Arg
145                 150                 155                 160
Leu Ser Ser Trp Cys Leu Lys Lys Pro Gly His Val Ala Glu Val Tyr
                165                 170                 175
Leu Val His Leu His Ala Ser Val Tyr Ala Leu Phe His Arg Leu Tyr
            180                 185                 190
Gly Met Tyr Pro Cys Asn Phe Val Ser Phe Leu Arg Ser His Tyr Ser
            195                 200                 205
Met Lys Glu Asn Leu Glu Thr Phe Glu Glu Val Val Lys Pro Met Met
        210                 215                 220
Glu His Val Arg Ile His Pro Glu Leu Val Thr Gly Ser Lys Asp His
225                 230                 235                 240
Glu Leu Asp Pro Arg Arg Trp Lys Arg Leu Glu Thr His Asp Val Val
                245                 250                 255
Ile Glu Cys Ala Lys Ile Ser Leu Asp Pro Thr Glu Ala Ser Tyr Glu
            260                 265                 270
Asp Gly Tyr Ser Val Ser His Gln Ile Ser Ala Arg Phe Pro His Arg
            275                 280                 285
Ser Ala Asp Val Thr Thr Ser Pro Tyr Ala Asp Thr Gln Asn Ser Tyr
        290                 295                 300
Gly Cys Ala Thr Ser Thr Pro Tyr Ser Thr Ser Arg Leu Met Leu Leu
305                 310                 315                 320
Asn Met Pro Gly Gln Leu Pro Gln Thr Leu Ser Ser Pro Ser Thr Arg
                325                 330                 335
Leu Ile Thr Glu Pro Pro Gln Ala Thr Leu Trp Ser Pro Ser Met Val
            340                 345                 350
Cys Gly Met Thr Thr Pro Pro Thr Ser Pro Gly Asn Val Pro Pro Asp
            355                 360                 365
Leu Ser His Pro Tyr Ser Lys Val Phe Gly Thr Thr Ala Gly Gly Lys
        370                 375                 380
Gly Thr Pro Leu Gly Thr Pro Ala Thr Ser Pro Pro Ala Pro Leu
385                 390                 395                 400
Cys His Ser Asp Asp Tyr Val His Ile Ser Leu Pro Gln Ala Thr Val
                405                 410                 415
Thr Pro Pro Arg Lys Glu Glu Arg Met Asp Ser Ala Arg Pro Cys Leu
            420                 425                 430
His Arg Gln His His Leu Leu Asn Asp Arg Gly Ser Glu Glu Pro Pro
            435                 440                 445
Gly Ser Lys Gly Ser Val Thr Leu Ser Asp Leu Pro Gly Phe Leu Gly
        450                 455                 460
Asp Leu Ala Ser Glu Glu Asp Ser Ile Glu Lys Asp Lys Glu Glu Ala
465                 470                 475                 480
Ala Ile Ser Arg Glu Leu Ser Glu Ile Thr Thr Ala Glu Ala Glu Pro
                485                 490                 495
Val Val Pro Arg Gly Gly Phe Asp Ser Pro Phe Tyr Arg Asp Ser Leu
            500                 505                 510
Pro Gly Ser Gln Arg Lys Thr His Ser Ala Ala Ser Ser Ser Gln Gly
            515                 520                 525
```

-continued

```
Ala Ser Val Asn Pro Glu Pro Leu His Ser Ser Leu Asp Lys Leu Gly
    530                 535                 540

Pro Asp Thr Pro Lys Gln Ala Phe Thr Pro Ile Asp Leu Pro Cys Gly
545                 550                 555                 560

Ser Ala Asp Glu Ser Pro Ala Gly Asp Arg Glu Cys Gln Thr Ser Leu
                565                 570                 575

Glu Thr Ser Ile Phe Thr Pro Ser Pro Cys Lys Ile Pro Pro Pro Thr
                580                 585                 590

Arg Val Gly Phe Gly Ser Gly Gln Pro Pro Tyr Asp His Leu Phe
            595                 600                 605

Glu Val Ala Leu Pro Lys Thr Ala His His Phe Val Ile Arg Lys Thr
610                 615                 620

Glu Glu Leu Leu Lys Lys Ala Lys Gly Asn Thr Glu Glu Asp Gly Val
625                 630                 635                 640

Pro Ser Thr Ser Pro Met Glu Val Leu Asp Arg Leu Ile Gln Gln Gly
                645                 650                 655

Ala Asp Ala His Ser Lys Glu Leu Asn Lys Leu Pro Leu Pro Ser Lys
                660                 665                 670

Ser Val Asp Trp Thr His Phe Gly Gly Ser Pro Pro Ser Asp Glu Ile
                675                 680                 685

Arg Thr Leu Arg Asp Gln Leu Leu Leu His Asn Gln Leu Leu Tyr
    690                 695                 700

Glu Arg Phe Lys Arg Gln Gln His Ala Leu Arg Asn Arg Arg Leu Leu
705                 710                 715                 720

Arg Lys Val Ile Lys Ala Ala Leu Glu Glu His Asn Ala Ala Met
                725                 730                 735

Lys Asp Gln Leu Lys Leu Gln Glu Lys Asp Ile Gln Met Trp Lys Val
                740                 745                 750

Ser Leu Gln Lys Glu Gln Ala Arg Tyr Asn Gln Leu Gln Glu Gln Arg
                755                 760                 765

Asp Thr Met Val Thr Lys Leu His Ser Gln Ile Arg Gln Leu Gln His
    770                 775                 780

Asp Arg Glu Glu Phe Tyr Asn Gln Ser Gln Glu Leu Gln Thr Lys Leu
785                 790                 795                 800

Glu Asp Cys Arg Asn Met Ile Ala Glu Leu Arg Ile Glu Leu Lys Lys
                805                 810                 815

Ala Asn Asn Lys Val Cys His Thr Glu Leu Leu Ser Gln Val Ser
                820                 825                 830

Gln Lys Leu Ser Asn Ser Glu Ser Val Gln Gln Met Glu Phe Leu
                835                 840                 845

Asn Arg Gln Leu Leu Val Leu Gly Glu Val Asn Glu Leu Tyr Leu Glu
    850                 855                 860

Gln Leu Gln Asn Lys His Ser Asp Thr Thr Lys Glu Val Glu Met Met
865                 870                 875                 880

Lys Ala Ala Tyr Arg Lys Glu Leu Glu Lys Asn Arg Ser His Val Leu
                885                 890                 895

Gln Gln Thr Gln Arg Leu Asp Thr Ser Gln Lys Arg Ile Leu Glu Leu
                900                 905                 910

Glu Ser His Leu Ala Lys Lys Asp His Leu Leu Leu Glu Gln Lys Lys
                915                 920                 925

Tyr Leu Glu Asp Val Lys Leu Gln Ala Arg Gly Gln Leu Gln Ala Ala
    930                 935                 940

Glu Ser Arg Tyr Glu Ala Gln Lys Arg Ile Thr Gln Val Phe Glu Leu
945                 950                 955                 960
```

```
Glu Ile Leu Asp Leu Tyr Gly Arg Leu Glu Lys Asp Gly Leu Leu Lys
            965                 970                 975
Lys Leu Glu Glu Glu Lys Ala Glu Ala Ala Glu Ala Ala Glu Glu Arg
            980                 985                 990
Leu Asp Cys Cys Asn Asp Gly Cys  Ser Asp Ser Met Val  Gly His Asn
            995                 1000                1005
Glu Glu  Ala Ser Gly His Asn  Gly Glu Thr Lys Thr  Pro Arg Pro
    1010                1015                1020
Ser Ser  Ala Arg Gly Ser Ser  Gly Ser Arg Gly Gly  Gly Gly Ser
    1025                1030                1035
Ser Ser  Ser Ser Ser Glu Leu  Ser Thr Pro Glu Lys  Pro Pro His
    1040                1045                1050
Gln Arg  Ala Gly Pro Phe Ser  Ser Arg Trp Glu Thr  Thr Met Gly
    1055                1060                1065
Glu Ala  Ser Ala Ser Ile Pro  Thr Thr Val Gly Ser  Leu Pro Ser
    1070                1075                1080
Ser Lys  Ser Phe Leu Gly Met  Lys Ala Arg Glu Leu  Phe Arg Asn
    1085                1090                1095
Lys Ser  Glu Ser Gln Cys Asp  Glu Asp Gly Met Thr  Ser Ser Leu
    1100                1105                1110
Ser Glu  Ser Leu Lys Thr Glu  Leu Gly Lys Asp Leu  Gly Val Glu
    1115                1120                1125
Ala Lys  Ile Pro Leu Asn Leu  Asp Gly Pro His Pro  Ser Pro Pro
    1130                1135                1140
Thr Pro  Asp Ser Val Gly Gln  Leu His Ile Met Asp  Tyr Asn Glu
    1145                1150                1155
Thr His  His Glu His Ser
    1160

<210> SEQ ID NO 5
<211> LENGTH: 5424
<212> TYPE: DNA
<213> ORGANISM: Homo sapiens

<400> SEQUENCE: 5
atggccaaac caacaagcaa agattcaggc ttgaaggaga agtttaagat tctgttggga      60
ctgggaacac cgaggccaaa tcccaggtct gcagagggta acagacgga gtttatcatc     120
accgcggaaa tactgagaga actgagcatg gaatgtggcc tcaacaatcg catccggatg     180
ataggcaga tttgtgaagt cgcaaaaacc aagaaatttg aagagcacgc agtggaagca     240
ctctggaagg cggtcgcgga tctgttgcag ccggagcgga cgctggaggc ccggcacgcg     300
gtgctggctc tgctgaaggc catcgtgcag gggcagggcg agcgtttggg ggtcctcaga     360
gccctcttct ttaaggtcat caaggattac ccttccaacg aagaccttca cgaaaggctg     420
gaggttttca aggccctcac agacaatggg agacacatca cctacttgga ggaagagctg     480
gctgactttg tcctgcagtg gatggatgtt ggcttgtcct cggaattcct tctggtgctg     540
gtgaacttgg tcaaattcaa tagctgttac ctcgacgagt acatcgcaag gatggttcag     600
atgatctgtc tgctgtgcgt ccggaccgcg tcctctgtgg acatagaggt ctccctgcag     660
gtgctggacg ccgtggtctg ctacaactgc ctgccggctg agagcctccc gctgttcatc     720
gttaccctct gtcgcaccat caacgtcaag gagctctgcg agccttgctg gaagctgatg     780
cggaaccttcc ttggcaccca cctgggccac agcgccatct acaacatgtg ccacctcatg     840
gaggacagag cctacatgga ggacgcgccc ctgctgagag agccgtgttt ttgtgggc      900
```

```
atggctctct ggggagccca ccggctctat tctctcagga actcgccgac atctgtgttt   960
ccatcatttt accaggccat ggcatgtccg aacgaggtgg tgtcctatga gatcgtcctg  1020
tccatcacca ggctcatcaa gaagtatagg aaggagctcc aggtggtggc gtgggacatt  1080
ctgctgaaca tcatcgaacg gctccttcaa cagctccaga ccttggacag cccggagctc  1140
aggaccatcg tccatgacct gttgaccacg gtggaggagc tgtgtgacca gaacgagttc  1200
cacgggtctc aggagagata ctttgaactg gtggagagat gtgcggacca gaggcctgag  1260
tcctccctcc tgaacctgat ctcctataga gcgcagtcca tccacccggc caaggacggc  1320
tggattcaga acctgcaggc gctgatggag agattcttca ggagcgagtc ccgaggcgcc  1380
gtgcgcatca aggtgctgga cgtgctgtcc tttgtgctgc tcatcaacag gcagttctat  1440
gaggaggagc tgattaactc agtggtcatc tcgcagctct cccacatccc cgaggataaa  1500
gaccaccagg tccgaaagct ggccacccag ttgctggtgg acctggcaga gggctgccac  1560
acacaccact tcaacagcct gctggacatc atcgagaagg tgatggcccg ctccctctcc  1620
ccacccccgg agctggaaga aagggatgtg ccgcatact cggcctcctt ggaggatgtg  1680
aagacagccg tcctggggct tctggtcatc cttcagacca agctgtacac cctgcctgca  1740
agccacgcca cgcgtgtgta tgagatgctg gtcagccaca ttcagctcca ctacaagcac  1800
agctacccc tgccaatcgc gagcagcatc cggctgcagg cctttgactt cctgtttctg  1860
ctgcgggccg actcactgca ccgcctgggc ctgcccaaca aggatggagt cgtgcggttc  1920
agccctact cgtctgcga ctacatggag ccagagagag gctctgagaa aagaccagc  1980
ggcccccttt ctcctcccac agggcctcct ggcccggcgc ctgcaggccc cgccgtgcgg  2040
ctggggtccg tgccctactc cctgctcttc cgcgtcctgc tgcagtgctt gaagcaggag  2100
tctgactgga aggtgctgaa gctggttctg ggcaggctgc ctgagtccct gcgctataaa  2160
gtgctcatct ttacttcccc ttgcagtgtg gaccagctgt gctctgctct ctgctccatg  2220
cttttcaggcc caaagacact ggagcggctc cgaggcgccc cagaaggctt ctccagaact  2280
gacttgcacc tggccgtggt tccagtgctg acagcattaa tctcttacca taactacctg  2340
gacaaaacca acagcgcga tggtctac tgcctggagc agggcctcat ccaccgctgt  2400
gccagacagt gcgtcgtggc cttgtccatc tgcagcgtgg agatgcctga catcatcatc  2460
aaggcgctgc ctgttctggt ggtgaagctc acgcacatct cagccacagc cagcatggcc  2520
gtcccactgc tggagttcct gtccactctg gccaggctgc cgcacctcta caggaacttt  2580
gccgcggagc agtatgccag tgtgttcgcc atctccctgc cgtacaccaa cccctccaag  2640
tttaatcagt acatcgtgtg tctggcccat cacgtcatag ccatgtggtt catcaggtgc  2700
cgcctgccct tccggaagga ttttgtccct ttcatcacta agggcctgcg gtccaatgtc  2760
ctcttgtctt ttgatgacac ccccgagaag gacagcttca gggcccggag tactagtctc  2820
aacgagagac ccaagagtct gaggatagcc agacccccca acaaggctt gaataactct  2880
ccacccgtga agaattcaa ggagagctct gcagccgagg ccttccggtg ccgcagcatc  2940
agtgtgtctg aacatgtggt ccgcagcagg atacagacgt ccctcaccag tgccagcttg  3000
gggtctgcag atgagaactc cgtggcccag gctgacgata gcctgaaaaa cctccacctg  3060
gagctcacgg aaacctgtct ggacatgatg gctcgatacg tcttctccaa cttcacggct  3120
gtcccgaaga ggtctcctgt gggcgagttc ctcctagcgg gtggcaggac caaaacctgg  3180
ctggttggga caagcttgt cactgtgacg acaagcgtgg gaaccgggac ccggtcgtta  3240
ctaggcctgg actcggggga gctgcagtcc ggcccggagt cgagctccag ccccggggtg  3300
```

```
catgtgagac agaccaagga ggcgccggcc aagctggagt cccaggctgg gcagcaggtg      3360
tcccgtgggg cccgggatcg ggtccgttcc atgtcggggg ccatggtct tcgagttggc      3420 gccctggacg tgccggcctc ccagttcctg ggcagtgcca cttctccagg accacggact      3480
gcaccagccg cgaaacctga gaaggcctca gctggcaccc gggttcctgt gcaggagaag      3540
acgaacctgg cggcctatgt gcccctgcta cccagggct gggcggagat cctggtccgg      3600
aggcccacag ggaacaccag ctggctgatg agcctggaga acccgctcag ccctttctcc      3660
tcggacatca caacatgcc cctgcaggag ctgtctaacg ccctcatggc ggctgagcgc      3720
ttcaaggagc accgggacac agccctgtac aagtcactgt cggtgccggc agccagcacg      3780
gccaaacccc ctcctctgcc tcgctccaac acagtggcct ctttctcctc cctgtaccag      3840
tccagctgcc aaggacagct gcacaggagc gtttcctggg cagactccgc cgtggtcatg      3900
gaggagggaa gtccgggcga ggttcctgtg ctggtggagc ccccagggtt ggaggacgtt      3960
gaggcagcgc taggcatgga caggcgcacg gatgcctaca gcaggtcgtc ctcagtctcc      4020
agccaggagg agaagtcgct ccacgcggag gagctggttg gcaggggcat ccccatcgag      4080
cgagtcgtct cctcggaggg tggccggccc tctgtgacc tctccttcca gccctcgcag      4140
cccctgagca gtccagctc ctctcccgag ctgcagactc tgcaggacat cctcggggac      4200
cctggggaca aggccgacgt gggccggctg agccctgagg ttaaggcccg gtcacagtca      4260
gggaccctgg acggggaaag tgctgcctgg tcggcctcgg gcgaagacag tcggggccag      4320
cccgagggtc ccttgccttc cagctccccc cgctcgccca gtggcctccg gccccgaggt      4380
tacaccatct ccgactcggc cccatcacgc aggggcaaga gagtagagag ggacgcctta      4440
aagagcagag ccacagcctc caatgcagag aaagtgccag gcatcaaccc cagtttcgtg      4500
ttcctgcagc tctaccattc cccttctt ggcgacgagt caaacaagcc aatcctgctg      4560
cccaatgagt cacagtcctt tgagcggtcg gtgcagctcc tcgaccagat cccatcatac      4620
gacacccaca agatcgccgt cctgtatgtt ggagaaggcc agagcaacag cgagctcgcc      4680
atcctgtcca atgagcatgg ctcctacagg tacacggagt tcctgacggg cctgggccgg      4740
ctcatcgagc tgaaggactg ccagccggac aaggtgtacc tgggaggcct ggacgtgtgt      4800
ggtgaggacg gccagttcac ctactgctgg cacgatgaca tcatgcaagc cgtcttccac      4860
atcgccaccc tgatgcccac caaggacgtg gacaagcacc gctgcgacaa gaagcgccac      4920
ctgggcaacg actttgtgtc cattgtctac aatgactccg gtgaggactt caagcttggc      4980
accatcaagg gccagttcaa cttttgtccac gtgatcgtca cccgctgga ctacgagtgc      5040 aacctggtgt ccctgcagtg caggaaagac atggagggcc ttgtggacac cagcgtggcc      5100
aagatcgtgt ctgaccgcaa cctgcccttc gtggcccgcc agatggccct gcacgcaaat      5160
atggcctcac aggtgcatca tagccgctcc aaccccaccg atatctaccc ctccaagtgg      5220
attgcccggc tccgccacat caagcggctc cgccagcgga tctgcgagga agccgcctac      5280
tccaacccca gcctacctct ggtgcaccct ccgtcccata gcaaagcccc tgcacagact      5340
ccagccgagc ccacacctgg ctatgaggtg ggccagcgga gcgcctcat ctcctcggtg      5400 gaggacttca ccgagtttgt gtga                                            5424
```

<210> SEQ ID NO 6
<211> LENGTH: 1807
<212> TYPE: PRT
<213> ORGANISM: Homo sapiens

<400> SEQUENCE: 6

```
Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
            20                  25                  30

Gly Lys Gln Thr Glu Phe Ile Ile Thr Ala Glu Ile Leu Arg Glu Leu
        35                  40                  45

Ser Met Glu Cys Gly Leu Asn Asn Arg Ile Arg Met Ile Gly Gln Ile
    50                  55                  60

Cys Glu Val Ala Lys Thr Lys Lys Phe Glu Glu His Ala Val Glu Ala
65              70                  75                  80

Leu Trp Lys Ala Val Ala Asp Leu Leu Gln Pro Glu Arg Thr Leu Glu
                85                  90                  95

Ala Arg His Ala Val Leu Ala Leu Leu Lys Ala Ile Val Gln Gly Gln
            100                 105                 110

Gly Glu Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145             150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Arg Met Val Gln Met Ile Cys Leu Leu Cys Val Arg
        195                 200                 205

Thr Ala Ser Ser Val Asp Ile Glu Val Ser Leu Gln Val Leu Asp Ala
210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys His Leu Met Glu Asp Arg Ala Tyr Met Glu Asp
        275                 280                 285

Ala Pro Leu Leu Arg Gly Ala Val Phe Phe Val Gly Met Ala Leu Trp
290                 295                 300

Gly Ala His Arg Leu Tyr Ser Leu Arg Asn Ser Pro Thr Ser Val Phe
305                 310                 315                 320

Pro Ser Phe Tyr Gln Ala Met Ala Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Val Val Ala Trp Asp Ile Leu Leu Asn Ile Ile Glu Arg Leu
        355                 360                 365

Leu Gln Gln Leu Gln Thr Leu Asp Ser Pro Glu Leu Arg Thr Ile Val
    370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
                405                 410                 415

Gln Arg Pro Glu Ser Ser Leu Leu Asn Leu Ile Ser Tyr Arg Ala Gln
```

-continued

```
                420             425             430
Ser Ile His Pro Ala Lys Asp Gly Trp Ile Gln Asn Leu Gln Ala Leu
            435                 440                 445
Met Glu Arg Phe Phe Arg Ser Glu Ser Arg Gly Ala Val Arg Ile Lys
    450                 455                 460
Val Leu Asp Val Leu Ser Phe Val Leu Ile Asn Arg Gln Phe Tyr
465                 470                 475                 480
Glu Glu Glu Leu Ile Asn Ser Val Val Ile Ser Gln Leu Ser His Ile
                485                 490                 495
Pro Glu Asp Lys Asp His Gln Val Arg Lys Leu Ala Thr Gln Leu Leu
            500                 505                 510
Val Asp Leu Ala Glu Gly Cys His Thr His His Phe Asn Ser Leu Leu
            515                 520                 525
Asp Ile Ile Glu Lys Val Met Ala Arg Ser Leu Ser Pro Pro Glu
            530                 535                 540
Leu Glu Glu Arg Asp Val Ala Ala Tyr Ser Ala Ser Leu Glu Asp Val
545                 550                 555                 560
Lys Thr Ala Val Leu Gly Leu Leu Val Ile Leu Gln Thr Lys Leu Tyr
                565                 570                 575
Thr Leu Pro Ala Ser His Ala Thr Arg Val Tyr Glu Met Leu Val Ser
            580                 585                 590
His Ile Gln Leu His Tyr Lys His Ser Tyr Thr Leu Pro Ile Ala Ser
                595                 600                 605
Ser Ile Arg Leu Gln Ala Phe Asp Phe Leu Phe Leu Leu Arg Ala Asp
            610                 615                 620
Ser Leu His Arg Leu Gly Leu Pro Asn Lys Asp Gly Val Val Arg Phe
625                 630                 635                 640
Ser Pro Tyr Cys Val Cys Asp Tyr Met Glu Pro Glu Arg Gly Ser Glu
                645                 650                 655
Lys Lys Thr Ser Gly Pro Leu Ser Pro Pro Thr Gly Pro Gly Pro
            660                 665                 670
Ala Pro Ala Gly Pro Ala Val Arg Leu Gly Ser Val Pro Tyr Ser Leu
            675                 680                 685
Leu Phe Arg Val Leu Leu Gln Cys Leu Lys Gln Glu Ser Asp Trp Lys
            690                 695                 700
Val Leu Lys Leu Val Leu Gly Arg Leu Pro Glu Ser Leu Arg Tyr Lys
705                 710                 715                 720
Val Leu Ile Phe Thr Ser Pro Cys Ser Val Asp Gln Leu Cys Ser Ala
                725                 730                 735
Leu Cys Ser Met Leu Ser Gly Pro Lys Thr Leu Glu Arg Leu Arg Gly
            740                 745                 750
Ala Pro Glu Gly Phe Ser Arg Thr Asp Leu His Leu Ala Val Val Pro
            755                 760                 765
Val Leu Thr Ala Leu Ile Ser Tyr His Asn Tyr Leu Asp Lys Thr Lys
            770                 775                 780
Gln Arg Glu Met Val Tyr Cys Leu Glu Gln Gly Leu Ile His Arg Cys
785                 790                 795                 800
Ala Arg Gln Cys Val Val Ala Leu Ser Ile Cys Ser Val Glu Met Pro
                805                 810                 815
Asp Ile Ile Ile Lys Ala Leu Pro Val Leu Val Lys Leu Thr His
            820                 825                 830
Ile Ser Ala Thr Ala Ser Met Ala Val Pro Leu Leu Glu Phe Leu Ser
            835                 840                 845
```

-continued

Thr Leu Ala Arg Leu Pro His Leu Tyr Arg Asn Phe Ala Glu Gln
850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
            885                 890                 895

Phe Ile Arg Cys Arg Leu Pro Phe Arg Lys Asp Phe Val Pro Phe Ile
            900                 905                 910

Thr Lys Gly Leu Arg Ser Asn Val Leu Leu Ser Phe Asp Asp Thr Pro
            915                 920                 925

Glu Lys Asp Ser Phe Arg Ala Arg Ser Thr Ser Leu Asn Glu Arg Pro
            930                 935                 940

Lys Ser Leu Arg Ile Ala Arg Pro Pro Lys Gln Gly Leu Asn Asn Ser
945                 950                 955                 960

Pro Pro Val Lys Glu Phe Lys Glu Ser Ala Ala Glu Ala Phe Arg
                965                 970                 975

Cys Arg Ser Ile Ser Val Ser Glu His Val Val Arg Ser Arg Ile Gln
            980                 985                 990

Thr Ser Leu Thr Ser Ala Ser Leu Gly Ser Ala Asp Glu Asn Ser Val
            995                 1000                1005

Ala Gln Ala Asp Asp Ser Leu Lys Asn Leu His Leu Glu Leu Thr
    1010                1015                1020

Glu Thr Cys Leu Asp Met Met Ala Arg Tyr Val Phe Ser Asn Phe
    1025                1030                1035

Thr Ala Val Pro Lys Arg Ser Pro Val Gly Glu Phe Leu Leu Ala
    1040                1045                1050

Gly Gly Arg Thr Lys Thr Trp Leu Val Gly Asn Lys Leu Val Thr
    1055                1060                1065

Val Thr Thr Ser Val Gly Thr Gly Thr Arg Ser Leu Leu Gly Leu
    1070                1075                1080

Asp Ser Gly Glu Leu Gln Ser Gly Pro Glu Ser Ser Ser Pro
    1085                1090                1095

Gly Val His Val Arg Gln Thr Lys Glu Ala Pro Ala Lys Leu Glu
    1100                1105                1110

Ser Gln Ala Gly Gln Gln Val Ser Arg Gly Ala Arg Asp Arg Val
    1115                1120                1125

Arg Ser Met Ser Gly Gly His Gly Leu Arg Val Gly Ala Leu Asp
    1130                1135                1140

Val Pro Ala Ser Gln Phe Leu Gly Ser Ala Thr Ser Pro Gly Pro
    1145                1150                1155

Arg Thr Ala Pro Ala Ala Lys Pro Glu Lys Ala Ser Ala Gly Thr
    1160                1165                1170

Arg Val Pro Val Gln Glu Lys Thr Asn Leu Ala Ala Tyr Val Pro
    1175                1180                1185

Leu Leu Thr Gln Gly Trp Ala Glu Ile Leu Val Arg Arg Pro Thr
    1190                1195                1200

Gly Asn Thr Ser Trp Leu Met Ser Leu Glu Asn Pro Leu Ser Pro
    1205                1210                1215

Phe Ser Ser Asp Ile Asn Asn Met Pro Leu Gln Glu Leu Ser Asn
    1220                1225                1230

Ala Leu Met Ala Ala Glu Arg Phe Lys Glu His Arg Asp Thr Ala
    1235                1240                1245

Leu Tyr Lys Ser Leu Ser Val Pro Ala Ala Ser Thr Ala Lys Pro
    1250                1255                1260

```
Pro Pro Leu Pro Arg Ser Asn Thr Val Ala Ser Phe Ser Ser Leu
    1265                1270                1275

Tyr Gln Ser Ser Cys Gln Gly Gln Leu His Arg Ser Val Ser Trp
    1280                1285                1290

Ala Asp Ser Ala Val Val Met Glu Glu Gly Ser Pro Gly Glu Val
    1295                1300                1305

Pro Val Leu Val Glu Pro Pro Gly Leu Glu Asp Val Glu Ala Ala
    1310                1315                1320

Leu Gly Met Asp Arg Arg Thr Asp Ala Tyr Ser Arg Ser Ser Ser
    1325                1330                1335

Val Ser Ser Gln Glu Glu Lys Ser Leu His Ala Glu Glu Leu Val
    1340                1345                1350

Gly Arg Gly Ile Pro Ile Glu Arg Val Val Ser Glu Gly Gly
    1355                1360                1365

Arg Pro Ser Val Asp Leu Ser Phe Gln Pro Ser Gln Pro Leu Ser
    1370                1375                1380

Lys Ser Ser Ser Pro Glu Leu Gln Thr Leu Gln Asp Ile Leu
    1385                1390                1395

Gly Asp Pro Gly Asp Lys Ala Asp Val Gly Arg Leu Ser Pro Glu
    1400                1405                1410

Val Lys Ala Arg Ser Gln Ser Gly Thr Leu Asp Gly Glu Ser Ala
    1415                1420                1425

Ala Trp Ser Ala Ser Gly Glu Asp Ser Arg Gly Gln Pro Glu Gly
    1430                1435                1440

Pro Leu Pro Ser Ser Ser Pro Arg Ser Pro Ser Gly Leu Arg Pro
    1445                1450                1455

Arg Gly Tyr Thr Ile Ser Asp Ser Ala Pro Ser Arg Arg Gly Lys
    1460                1465                1470

Arg Val Glu Arg Asp Ala Leu Lys Ser Arg Ala Thr Ala Ser Asn
    1475                1480                1485

Ala Glu Lys Val Pro Gly Ile Asn Pro Ser Phe Val Phe Leu Gln
    1490                1495                1500

Leu Tyr His Ser Pro Phe Phe Gly Asp Glu Ser Asn Lys Pro Ile
    1505                1510                1515

Leu Leu Pro Asn Glu Ser Gln Ser Phe Glu Arg Ser Val Gln Leu
    1520                1525                1530

Leu Asp Gln Ile Pro Ser Tyr Asp Thr His Lys Ile Ala Val Leu
    1535                1540                1545

Tyr Val Gly Glu Gly Gln Ser Asn Ser Glu Leu Ala Ile Leu Ser
    1550                1555                1560

Asn Glu His Gly Ser Tyr Arg Tyr Thr Glu Phe Leu Thr Gly Leu
    1565                1570                1575

Gly Arg Leu Ile Glu Leu Lys Asp Cys Gln Pro Asp Lys Val Tyr
    1580                1585                1590

Leu Gly Gly Leu Asp Val Cys Gly Glu Asp Gly Gln Phe Thr Tyr
    1595                1600                1605

Cys Trp His Asp Asp Ile Met Gln Ala Val Phe His Ile Ala Thr
    1610                1615                1620

Leu Met Pro Thr Lys Asp Val Asp Lys His Arg Cys Asp Lys Lys
    1625                1630                1635

Arg His Leu Gly Asn Asp Phe Val Ser Ile Val Tyr Asn Asp Ser
    1640                1645                1650

Gly Glu Asp Phe Lys Leu Gly Thr Ile Lys Gly Gln Phe Asn Phe
```

-continued

```
                      1655                1660                1665

Val His  Val Ile Val Thr Pro Leu Asp Tyr Glu Cys  Asn Leu Val
         1670                1675                1680

Ser Leu  Gln Cys Arg Lys Asp Met Glu Gly Leu Val  Asp Thr Ser
         1685                1690                1695

Val Ala  Lys Ile Val Ser Asp Arg Asn Leu Pro Phe  Val Ala Arg
         1700                1705                1710

Gln Met  Ala Leu His Ala Asn Met Ala Ser Gln Val  His His Ser
         1715                1720                1725

Arg Ser  Asn Pro Thr Asp Ile Tyr Pro Ser Lys Trp  Ile Ala Arg
         1730                1735                1740

Leu Arg  His Ile Lys Arg Leu Arg Gln Arg Ile Cys  Glu Glu Ala
         1745                1750                1755

Ala Tyr  Ser Asn Pro Ser Leu Pro Leu Val His Pro  Pro Ser His
         1760                1765                1770

Ser Lys  Ala Pro Ala Gln Thr Pro Ala Glu Pro Thr  Pro Gly Tyr
         1775                1780                1785

Glu Val  Gly Gln Arg Lys Arg Leu Ile Ser Ser Val  Glu Asp Phe
         1790                1795                1800

Thr Glu  Phe Val
         1805
```

<210> SEQ ID NO 7
<211> LENGTH: 1356
<212> TYPE: DNA
<213> ORGANISM: Homo sapiens

<400> SEQUENCE: 7

```
atgcgtgagt gcatctccat ccacgttggc caggctggtg tccagattgg caatgcctgc      60
tgggagctct actgcctgga acacggcatc cagcccgatg ccagatgcca agtgacaag     120
accattgggg aggagatga ctccttcaac accttcttca gtgagacggg cgctggcaag     180
cacgtccccc gggctgtgtt tgtagacttg aacccacag tcattgatga agttcgcact     240
ggcacctacc gccagctctt ccaccctgag cagctcatca caggcaagga agatgctgcc     300
aataactatg cccgagggca ctacaccatt ggcaaggaga tcattgacct tgtgttggac     360
cgaattcgca agctggctga ccagtgcacc ggtcttcagg gcttcttggt tttccacagc     420
tttggtgggg aactggttc tgggttcacc tccctgctca tggaacgtct ctcagttgat     480
tatggcaaga gtccaagct ggagttctcc atttacccag cacccaggt ttccacagct     540
gtagttgagc cctacaactc catcctcacc acccacacca cctggagca ctctgattgt     600
gccttcatgg tagacaatga ggccatctat gacatctgtc gtagaaacct cgatatcgag     660
cgcccaacct acactaacct taaccgcctt attagccaga ttgtgtcctc catcactgct     720
tccctgagat ttgatggagc cctgaatgtt gacctgacag aattccagac caacctggtg     780
ccctacccc gcatccactt ccctctggcc acatatgccc tgtcatctc tgctgagaaa     840
gcctaccatg aacagctttc gtagcagag atcaccaatg cttgctttga gccagccaac     900
cagatggtga atgtgacccc tcgccatggt aaatacatgg cttgctgcct gttgtaccgt     960
ggtgacgtgg ttcccaaaga tgtcaatgct gccattgcca ccatcaaaac caagcgcagc    1020
atccagtttg tggattggtg ccccactggc ttcaaggttg gcatcaacta ccagcctccc    1080
actgtggtgc ctggtggaga cctggccaag gtacagagag ctgtgtgcat gctgagcaac    1140
accacagcca ttgctgaggc ctgggctcgc ctggaccaca gttttgacct gatgtatgcc    1200
```

-continued

```
aagcgtgcct tgttcactg gtacgtgggt gaggggatgg aggaaggcga gttttcagag   1260
gcccgtgaag atatggctgc ccttgagaag gattatgagg aggttggtgt ggattctgtt   1320
gaaggagagg gtgaggaaga aggagaggaa tactaa                             1356
```

<210> SEQ ID NO 8
<211> LENGTH: 451
<212> TYPE: PRT
<213> ORGANISM: Homo sapiens

<400> SEQUENCE: 8

```
Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Glu Ile Thr Asn Ala Cys Phe Glu Pro Ala Asn Gln Met Val Lys
    290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Ser Ile Gln Phe Val Asp Trp Cys Pro Thr Gly Phe Lys
            340                 345                 350
```

-continued

```
Val Gly Ile Asn Tyr Gln Pro Pro Thr Val Val Pro Gly Gly Asp Leu
        355                 360                 365

Ala Lys Val Gln Arg Ala Val Cys Met Leu Ser Asn Thr Thr Ala Ile
    370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
            405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Glu Gly
        435                 440                 445

Glu Glu Tyr
    450
```